US012680128B2

(12) United States Patent (10) Patent No.: US 12,680,128 B2
Kohli et al. (45) Date of Patent: Jul. 14, 2026

(54) COMPOSITIONS AND METHODS FOR DNA CYTOSINE CARBOXYMETHYLATION

(71) Applicant: THE TRUSTEES OF THE UNIVERSITY OF PENNSYLVANIA, Philadelphia, PA (US)

(72) Inventors: Rahul Kohli, Penn Valley, PA (US); Tong Wang, Philadelphia, PA (US); Emily Schutsky, Waltham, MA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 797 days.

(21) Appl. No.: 17/999,260

(22) PCT Filed: May 19, 2021

(86) PCT No.: PCT/US2021/033169
§ 371 (c)(1),
(2) Date: Nov. 18, 2022

(87) PCT Pub. No.: WO2021/236778
PCT Pub. Date: Nov. 25, 2021

(65) Prior Publication Data
US 2023/0183793 A1 Jun. 15, 2023

Related U.S. Application Data

(60) Provisional application No. 63/027,254, filed on May 19, 2020.

(51) Int. Cl.
| | |
|---|---|
| *C12Q 1/6858* | (2018.01) |
| *C12N 9/10* | (2006.01) |
| *C12Q 1/48* | (2006.01) |
| *C12Q 1/6806* | (2018.01) |

(52) U.S. Cl.
CPC ......... *C12Q 1/6858* (2013.01); *C12N 9/1007* (2013.01); *C12Y 201/01037* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 11,286,493 B2 * | 3/2022 | Jacobsen ............ | C12N 15/8216 |
| 2012/0244549 A1 * | 9/2012 | Lowery .............. | G01N 33/6815 |
| | | | 435/7.1 |
| 2019/0185919 A1 | 6/2019 | Vaisvila et al. | |

OTHER PUBLICATIONS

International Search Report and Written Opinion dated Dec. 3, 2021 issued in corresponding International Patent Application No. PCT/US2021/033169.

Dankers, A domino biochemical reaction for Modification of biological nucleophiles with Methyltransferases. Dissertation. RWTH Aachen University, 2019 [online]. (Retrieved on Aug. 12, 2021). Retrieved from the internet: <URL: https://publications.rwth-aachen.de/record/76.
Kim et al. Determinants of the CmoB carboxymethyl transferase utilized for selective tRNA wobble modification. May 19, 2015, vol. 43, No. 9, pp. 4602-4613.
Krueger, A. T., and Kool, E. T. "Redesigning the architecture of the base pair: toward biochemical and biological function of new genetic sets." Chemistry & biology 16.3 (2009): 242-248.
Malyshev, D. A., et al. "A semi-synthetic organism with an expanded genetic alphabet." Nature 509.7500 (2014): 385-388.
Mehta, A. P., et al. "Replacement of 2'-deoxycytidine by 2'-deoxycytidine analogues in the *E. coli* genome." Journal of the American Chemical Society 138.43 (2016): 14230-14233.
Nabel, C. S., et al. (2012) The curious chemical biology of cytosine: Deamination, methylation, and oxidation as modulators of genomic potential. ACS Chem. Biol. 7, 20-30.
Sanchez-Romero, M. A., and Casadesus, J. "The bacterial epigenome." Nature Reviews Microbiology 18.1 (2020): 7-20.
Iyer, L. M., et al. "Natural history of eukaryotic DNA methylation systems." Prog Mol Biol Transl Sci 101: 25-104. (2011).
Wojciechowski, M., et al. "CpG underrepresentation and the bacterial CpG-specific DNA methyltransferase M. Mpel." Proceedings of the National Academy of Sciences 110.1 (2013): 105-110.
Zhang, X. and Bruice, T. C. "The mechanism of M. Hhal DNA C5 cytosine methyltransferase enzyme: a quantum mechanics/molecular mechanics approach." Proceedings of the National Academy of Sciences 103.16 (2006): 6148-6153.
Jurkowski, T. P. and Jeltsch, A. "On the evolutionary origin of eukaryotic DNA methyltransferases and Dnmt2." PloS one 6.11 (2011): e28104.
Lukinavicius, G., et al. (2012) Engineering the DNA cytosine-5 methyltransferase reaction for sequence-specific labeling of DNA. Nucleic Acids Res. 40, 11594-11602.
Liu, M. Y., et al. (2016) Quantification of oxidized 5-methylcytosine bases and TET enzyme activity. Methods Enzymol. 573, 365-385.
Kim, J, et al. "Structure-guided discovery of the metabolite carboxy-SAM that modulates tRNA function." Nature 498.7452 (2013): 123-126.
Baba, T., et al. "Construction of *Escherichia coli* K-12 in-frame, single-gene knockout mutants: the Keio collection." Molecular systems biology 2.1 (2006): 2006-0008.
Kitagawa, M., et al. "Complete set of ORF clones of *Escherichia coli* ASKA library (A Complete S et of *E. coli* K-12 ORF A Archive): Unique Resources for Biological Research." DNA research 12.5 (2005): 291-299.
Serebryakova, M., et al. "A Trojan-horse peptide-carboxymethyl-cytidine antibiotic from Bacillus amyloliquefaciens." Journal of the American Chemical Society 138.48 (2016): 15690-15698.
Nabel, C. S., et al. "DNA Methyltransferases Demonstrate Reduced Activity against Arabinosylcytosine: Implications for Epigenetic Instability in Acute Myeloid Leukemia." Biochemistry 56.16 (2017): 2166-2169.

(Continued)

*Primary Examiner* — Manjunath N Rao
*Assistant Examiner* — Jae W Lee
(74) *Attorney, Agent, or Firm* — Howson & Howson, LLP; Kathleen D. Rigaut; Richard F. Kane

(57) ABSTRACT

Compositions and methods for carboxymethylation of cytosine containing DNA and applications thereof for direct sequencing of 5mC are disclosed.

22 Claims, 30 Drawing Sheets

Specification includes a Sequence Listing.

(56)       References Cited

OTHER PUBLICATIONS

Dalhoff, C., et al. (2006) Direct transfer of extended groups from synthetic cofactors by DNA methyltransferases. Nat. Chem. Biol. 2, 31-32.

Xue, J-H., et al. "A vitamin-C-derived DNA modification catalysed by an algal TET homologue." Nature 569.7757 (2019): 581-585.

Zhang, Y., et al. "A semisynthetic organism engineered for the stable expansion of the genetic alphabet." Proceedings of the National Academy of Sciences 114.6 (2017): 1317-1322.

Zhang, Y, et al. "A semi-synthetic organism that stores and retrieves increased genetic information." Nature 551.7682 (2017): 644-647.

Chin, J. W. "Expanding and reprogramming the genetic code of cells and animals." Annual review of biochemistry 83 (2014): 379-408.

Schutsky, E. K., et al. (2018) Nondestructive, base-resolution sequencing of 5-hydroxymethylcytosine using a DNA deaminase. Nat. Biotech. e-pub ahead of print, doi: 10.1038/nbt.4204.

Kubiak, J. M., et al. "A small-molecule inducible synthetic circuit for control of the SOS gene network without DNA damage." ACS Synthetic Biology 6.11 (2017): 2067-2076.

Engler, C., et al. "A one pot, one step, precision cloning method with high throughput capability." PloS one 3.11 (2008): e3647.

Denizio, J. E., et al. "Selectivity and promiscuity in TET-mediated oxidation of 5-methylcytosine in DNA and RNA." Biochemistry 58.5 (2018): 411-421.

Dang, L., et al. "Cancer-associated IDH1 mutations produce 2-hydroxyglutarate." Nature 462.7274 (2009): 739-744.

Xu, Q., et al. "IDH1/2 mutants inhibit TET-promoted oxidation of RNA 5mC to 5hmC." PLoS One 11.8 (2016): e0161261.

Bestor, T. H., and Bourc'his, D. (2004) Transposon silencing and imprint establishment in mammalian germ cells. Cold Spring Harb. Symp. Quant. Biol. 69, 381-387.

Jaenisch, R., and Bird, A. (2003) Epigenetic regulation of gene expression: How the genome integrates intrinsic and environmental signals. Nat. Genet. 33 Suppl, 245-254.

Klose, R. J., and Bird, A. P. (2006) Genomic DNA methylation: The mark and its mediators. Trends Biochem. Sci. 31, 89-97.

Schubeler, D. (2015) Function and information content of DNA methylation. Nature. 517, 321-326.

Varley, K. E., et al. (2013) Dynamic DNA methylation across diverse human cell lines and tissues. Genome Res. 23, 555-567.

Tahiliani, M., et al. (2009) Conversion of 5-methylcytosine to 5-hydroxymethylcytosine in mammalian DNA by MLL partner TET1. Science. 324, 930-935.

Ito, S., et al. (2011) Tet proteins can convert 5-methylcytosine to 5-formylcytosine and 5-carboxylcytosine. Science. 333, 1300-1303.

He, Y. F., et al. (2011) Tet-mediated formation of 5-carboxylcytosine and its excision by TDG in mammalian DNA. Science. 333, 1303-1307.

Pfaffeneder, T., et al. (2011) The discovery of 5-formylcytosine in embryonic stem cell DNA. Angew. Chem. Int. Ed Engl. 50, 7008-7012.

Kohli, R. M., and Zhang, Y. (2013) TET enzymes, TDG and the dynamics of DNA demethylation. Nature. 502, 472-479.

Wagner, M., et al. (2015) Age-dependent levels of 5-methyl-, 5-hydroxymethyl-, and 5-formylcytosine in human and mouse brain tissues. Angew. Chem. Int. Ed Engl. 54, 12511-12514.

Bachman, M., et al. (2015) 5-formylcytosine can be a stable DNA modification in mammals. Nat. Chem. Biol. 11, 555-557.

Booth, M. J., et al. (2015) Chemical methods for decoding cytosine modifications in DNA. Chem. Rev. 115, 2240-2254.

Song, C. X., Yi, C., and He, C. (2012) Mapping recently identified nucleotide variants in the genome and transcriptome. Nat. Biotechnol. 30, 1107-1116.

Wu, H., and Zhang, Y. (2015) Charting oxidized methylcytosines at base resolution. Nat. Struct. Mol. Biol. 22, 656-661.

Darst, R. P., et al. (2010) Bisulfite sequencing of DNA. Curr. Protoc. Mol. Biol. Chapter 7, Unit 7.9.1-17.

Huang, Y., et al. (2010) The behaviour of 5-hydroxymethylcytosine in bisulfite sequencing. PLoS One. 5, e8888.

Yu, M., et al. (2012) Base-resolution analysis of 5-hydroxymethylcytosine in the mammalian genome. Cell. 149, 1368-1380.

Yu, M., et al. (2012) Tet-assisted bisulfite sequencing of 5-hydroxymethylcytosine. Nat. Protoc. 7, 2159-2170.

Booth, M. J., et al. (2012) Quantitative sequencing of 5-methylcytosine and 5-hydroxymethylcytosine at single-base resolution. Science. 336, 934-937.

Shoemaker, R., et al. (2010) Allele-specific methylation is prevalent and is contributed by CpG-SNPs in the human genome. Genome Res. 20, 883-889.

Yue, X., et al. (2016) Control of Foxp3 stability through modulation of TET activity. J. Exp. Med. 213, 377-397.

Schreiber, J., et al. (2013) Error rates for nanopore discrimination among cytosine, methylcytosine, and hydroxymethylcytosine along individual DNA strands. Proc. Natl. Acad. Sci. U. S. A. 110, 18910-18915.

Simpson, J. T., et al. (2017) Detecting DNA cytosine methylation using nanopore sequencing. Nat. Methods. 14, 407-410.

Hoijer, I., et al. (2018) Detailed analysis of HTT repeat elements in human blood using targeted amplification-free long-read sequencing. Hum. Mutat. 39, 1262-1272.

Tsai, Y., et al. (2017) Amplification-free, CRISPR-Cas9 targeted enrichment and SMRT sequencing of repeat-expansion disease causative genomic regions. BioRx. 203919; doi: https://doi.org/10.1101/203919.

Samorodnitsky, E., et al. (2015) Comparison of custom capture for targeted next-generation DNA sequencing. J. Mol. Diagn. 17, 64-75.

Tanaka, K., and Okamoto, A. (2007) Degradation of DNA by bisulfite treatment. Bioorg. Med. Chem. Lett. 17, 1912-1915.

Grunau, C., et al. (2001) Bisulfite genomic sequencing: Systematic investigation of critical experimental parameters. Nucleic Acids Res. 29, E65-5.

Patterson, K., et al. (2011) DNA methylation: Bisulphite modification and analysis. J. Vis. Exp. (56). pii: 3170. doi, 10.3791/3170.

Warnecke, P. M., et al. (2002) Identification and resolution of artifacts in bisulfite sequencing. Methods. 27, 101-107.

Meissner, A., et al. (2005) Reduced representation bisulfite sequencing for comparative high-resolution DNA methylation analysis. Nucleic Acids Res. 33, 5868-5877.

Gu, H., et al. (2011) Preparation of reduced representation bisulfite sequencing libraries for genome-scale DNA methylation profiling. Nat. Protoc. 6, 468-481.

Wescoe, Z. L., et al. (2014) Nanopores discriminate among five C5-cytosine variants in DNA. J. Am. Chem. Soc. 136, 16582-16587.

Li, W. et al. (2013) Single-molecule detection of 5-hydroxymethylcytosine in DNA through chemical modification and nanopore analysis. Angew. Chem. Int. Ed Engl. 52, 4350-4355.

Wanunu, M., et al. (2011) Discrimination of methylcytosine from hydroxymethylcytosine in DNA molecules. J. Am. Chem. Soc. 133, 486-492.

Wallace, E. V., et al. (2010) Identification of epigenetic DNA modifications with a protein nanopore. Chem. Commun. (Camb). 46, 8195-8197.

Laszlo, A. H., et al. (2013) Detection and mapping of 5-methylcytosine and 5- hydroxymethylcytosine with nanopore MspA. Proc. Natl. Acad. Sci. U. S. A. 110, 18904-18909.

Chavez, L., et al. (2014) Simultaneous sequencing of oxidized methylcytosines produced by TET/JBP dioxygenases in coprinopsis cinerea. Proc. Natl. Acad. Sci. U. S. A. 111, E5149-58.

Flusberg, B. A., et al. (2010) Direct detection of DNA methylation during single-molecule, real-time sequencing. Nat. Methods. 7, 461-465.

Nabel, C. S., et al. (2012) AID/APOBEC deaminases disfavor modified cytosines implicated in DNA demethylation. Nat. Chem. Biol. 8, 751-758.

Schutsky, E. K., et al. (2017) APOBEC3A efficiently deaminates methylated, but not TET-oxidized, cytosine bases in DNA. Nucleic Acids Res. 45, 7655-7665.

(56) References Cited

OTHER PUBLICATIONS

Shi, K., et al. (2017) Structural basis for targeted DNA cytosine deamination and mutagenesis by APOBEC3A and APOBEC3B. Nat. Struct. Mol. Biol. 24, 131-139.

Kouno, T., et al. (2017) Crystal structure of APOBEC3A bound to single-stranded DNA reveals structural basis for cytidine deamination and specificity. Nat. Commun. 8, 15024.

Siriwardena, S. U., et al. (2016) Functions and malfunctions of mammalian DNA- cytosine deaminases. Chem. Rev. 116, 12688-12710.

Beale, R. C., et al. (2004) Comparison of the differential context-dependence of DNA deamination by APOBEC enzymes: Correlation with mutation spectra in vivo. J. Mol. Biol. 337, 585-596.

Liu, M. Y., et al. (2017) Mutations along a TET2 active site scaffold stall oxidation at 5-hydroxymethylcytosine. Nat. Chem. Biol. 13, 181-187.

Crawford, D. J., et al. (2016) Tet2 catalyzes stepwise 5-methylcytosine oxidation by an iterative and de novo mechanism. J. Am. Chem. Soc. 138, 730-733.

Bryson, A. L., et al. (2015) Covalent modification of bacteriophage T4 DNA inhibits CRISPR-Cas9. MBio. 6, e00648-15.

Kizaki, S., and Sugiyama, H. (2014) CGmCGCG is a versatile substrate with which to evaluate tet protein activity. Org. Biomol. Chem. 12, 104-107.

Fu, L., et al. (2014) Tet-mediated formation of 5-hydroxymethylcytosine in RNA. J. Am. Chem. Soc. 136, 11582-11585.

Wang, H., et al. (2013) One-step generation of mice carrying mutations in multiple genes by CRISPR/cas-mediated genome engineering. Cell. 153, 910-918.

Lu, F., et al. (2014) Role of tet proteins in enhancer activity and telomere elongation. Genes Dev. 28, 2103-2119.

Wu, H., et al. (2014) Single-base resolution analysis of active DNA demethylation using methylase-assisted bisulfite sequencing. Nat. Biotechnol. 32, 1231-1240.

Smallwood, S. A., et al. (2014) Single-cell genome-wide bisulfite sequencing for assessing epigenetic heterogeneity. Nat. Methods. 11, 817-820.

Luo, C., et al. (2017) Single-cell methylomes identify neuronal subtypes and regulatory elements in mammalian cortex. Science. 357, 600- 604.

Mulqueen, R. M., et al. (2018) Highly scalable generation of DNA methylation profiles in single cells. Nat. Biotechnol. 36, 428-431.

Kelsey, G., et al. (2017) Single-cell epigenomics: Recording the past and predicting the future. Science. 358, 69-75.

Gawad, C., et al. (2016) Single-cell genome sequencing: Current state of the science. Nat. Rev. Genet. 17, 175-188.

Lister, R., et al. (2013) Global epigenomic reconfiguration during mammalian brain development. Science. 341, 1237905.

Kriacionis, S., and Heintz, N. (2009) The nuclear DNA base 5-hydroxymethylcytosine is present in purkinje neurons and the brain. Science. 324, 929-930.

Angermueller, C., et al. (2016) Parallel single-cell sequencing links transcriptional and epigenetic heterogeneity. Nat. Methods. 13, 229-232.

Cholewa-Waclaw, J., Bird, et al. (2016) The role of epigenetic mechanisms in the regulation of gene expression in the nervous system. J. Neurosci. 36, 11427-11434.

Hu, P., et al. (2017) Dissecting cell-type composition and activity-dependent transcriptional state in mammalian brains by massively parallel single-nucleus RNA-seq. Mol. Cell. 68, 1006-1015.e7.

Fisher, S., et al. (2011) A scalable, fully automated process for construction of sequence-ready human exome targeted capture libraries. Genome Biol. 12, R1-2011-12-1-r1. Epub Jan. 4, 2011.

Dunham, J. P., and Friesen, M. L. (2013) A cost-effective method for high-throughput construction of illumina sequencing libraries. Cold Spring Harb Protoc. 2013, 820-834.

Picelli, S., et al. (2013) Smart- seq2 for sensitive full-length transcriptome profiling in single cells. Nat. Methods. 10, 1096-1098.

Schutsky, E. K., et al. (2017) Mechanisms for targeted, purposeful mutation revealed in an APOBEC-DNA complex. Nat. Struct. Mol. Biol. 24, 97-98.

Wu, H., et al. (2016) Base-resolution profiling of active DNA demethylation using MAB- seq and caMAB-seq. Nat. Protoc. 11, 1081-1100.

Kriukiene, E.,et al. (2013) DNA unmethylome profiling by covalent capture of CpG sites. Nat. Commun. 4, 2190.

Liutkeviciute, Z., et al. (2011) Methyltransferase-directed derivatization of 5-hydroxymethylcytosine in DNA. Angew. Chem. Int. Ed Engl. 50, 2090-2093.

Dalhoff, C., et al. (2006) Synthesis of S-adenosyl-L-methionine analogs and their use for sequence-specific transalkylation of DNA by methyltransferases. Nat. Protoc. 1, 1879-1886.

Kohli, R. M., et al. (2009) A portable hotspot recognition loop transfers sequence preferences from APOBEC family members to activation-induced cytidine deaminase. J. Biol. Chem. 284, 22898-22904.

Gajula, K. S., et al. (2014) High-throughput mutagenesis reveals functional determinants for DNA targeting by activation-induced deaminase. Nucleic Acids Res. 42, 9964-9975.

Masevicius V., et al. (2016) Synthesis of S-adenosyl-L-methionine analogs with extended transferable groups for methyltransferase-directed labeling of DNA and RNA. Curr. Protoc. Nucleic Acid Chem. 64, 1.36.1-13.

Beaulaurier, J., et al. (2015) Single molecule-level detection and long read-based phasing of epigenetic variations in bacterial methylomes. Nat. Commun. 6, 7438.

Eckhardt, F., et al. (2006) DNA methylation profiling of human chromosomes 6, 20 and 22. Nat. Genet. 38, 1378-1385.

* cited by examiner

| M.Mpel | Preference CxSAM/SAM |
|--------|----------------------|
| WT | <0.01 |
| N374K | 1.27 |

```
Dcm:    425-VSDTQAYRQFGNSVVV-440
M.MpeI:  363-ISENKMIYIAGNSIPV-378
```

Motif X

| Base | Chemical | | Enzymatic | |
| --- | --- | --- | --- | --- |
| | BS-Seq | TAB Seq | ACE-Seq | DM-Seq |
| C | | | | |
| 5mC | | | | |
| 5hmC | | | | |

= C    = 5mC    = 5hmC    = T

FIG. 15A ssDNA.5'   3'

PDB:5SWW steric blockage
to bulky C5 substituents

FIG. 16A

SEQUENCE LISTING

```
<160> NUMBER OF SEQ ID NOS: 91

<210> SEQ ID NO 1
<211> LENGTH: 397
<212> TYPE: PRT
<213> ORGANISM: Artificial Sequence
<220> FEATURE:
<223> OTHER INFORMATION: M.MpeI N374K - No His tag

<400> SEQUENCE: 1

Met Asn Ser Asn Lys Asp Lys Ile Lys Val Ile Lys Val Phe Glu Ala
1               5                   10                  15

Phe Ala Gly Ile Gly Ser Gln Phe Lys Ala Leu Lys Asn Ile Ala Arg
                20                  25                  30

Ser Lys Asn Trp Glu Ile Gln His Ser Gly Met Val Glu Trp Phe Val
            35                  40                  45

Asp Ala Ile Val Ser Tyr Val Ala Ile His Ser Lys Asn Phe Asn Pro
        50                  55                  60

Lys Ile Glu Arg Leu Asp Arg Asp Ile Leu Ser Ile Ser Asn Asp Ser
65                  70                  75                  80

Lys Met Pro Ile Ser Glu Tyr Gly Ile Lys Lys Ile Asn Asn Thr Ile
                85                  90                  95

Lys Ala Ser Tyr Leu Asn Tyr Ala Lys Lys His Phe Asn Asn Leu Phe
                100                 105                 110

Asp Ile Lys Lys Val Asn Lys Asp Asn Phe Pro Lys Asn Ile Asp Ile
            115                 120                 125

Phe Thr Tyr Ser Phe Pro Cys Gln Asp Leu Ser Val Gln Gly Leu Gln
        130                 135                 140

Lys Gly Ile Asp Lys Glu Leu Asn Thr Arg Ser Gly Leu Leu Trp Glu
145                 150                 155                 160

Ile Glu Arg Ile Leu Glu Glu Ile Lys Asn Ser Phe Ser Lys Glu Glu
                165                 170                 175

Met Pro Lys Tyr Leu Leu Met Glu Asn Val Lys Asn Leu Leu Ser His
            180                 185                 190

Lys Asn Lys Lys Asn Tyr Asn Thr Trp Leu Lys Gln Leu Glu Lys Phe
        195                 200                 205

Gly Tyr Lys Ser Lys Thr Tyr Leu Leu Asn Ser Lys Asn Phe Asp Asn
    210                 215                 220

Cys Gln Asn Arg Glu Arg Val Phe Cys Leu Ser Ile Arg Asp Asp Tyr
225                 230                 235                 240

Leu Glu Lys Thr Gly Phe Lys Phe Lys Glu Leu Glu Lys Val Lys Asn
            245                 250                 255
```

```
Pro Pro Lys Lys Ile Lys Asp Ile Leu Val Asp Ser Ser Asn Tyr Lys
        260             265             270

Tyr Leu Asn Leu Asn Lys Tyr Glu Thr Thr Thr Phe Arg Glu Thr Lys
        275             280             285

Ser Asn Ile Ile Ser Arg Pro Leu Lys Asn Tyr Thr Thr Phe Asn Ser
    290             295             300

Glu Asn Tyr Val Tyr Asn Ile Asn Gly Ile Gly Pro Thr Leu Thr Ala
305             310             315             320

Ser Gly Ala Asn Ser Arg Ile Lys Ile Glu Thr Gln Gln Gly Val Arg
            325             330             335

Tyr Leu Thr Pro Leu Glu Cys Phe Lys Tyr Met Gln Phe Asp Val Asn
            340             345             350

Asp Phe Lys Lys Val Gln Ser Thr Asn Leu Ile Ser Glu Asn Lys Met
        355             360             365

Ile Tyr Ile Ala Gly Lys Ser Ile Pro Val Lys Ile Leu Glu Ala Ile
        370             375             380

Phe Asn Thr Leu Glu Phe Val Asn Asn Glu Glu Leu Glu
385             390             395
```

```
<210> SEQ ID NO 2
<211> LENGTH: 403
<212> TYPE: PRT
<213> ORGANISM: Artificial Sequence
<220> FEATURE:
<223> OTHER INFORMATION: M.MpeI N374K with His tag

<400> SEQUENCE: 2

Met Asn Ser Asn Lys Asp Lys Ile Lys Val Ile Lys Val Phe Glu Ala
1               5               10              15

Phe Ala Gly Ile Gly Ser Gln Phe Lys Ala Leu Lys Asn Ile Ala Arg
            20              25              30

Ser Lys Asn Trp Glu Ile Gln His Ser Gly Met Val Glu Trp Phe Val
        35              40              45

Asp Ala Ile Val Ser Tyr Val Ala Ile His Ser Lys Asn Phe Asn Pro
    50              55              60

Lys Ile Glu Arg Leu Asp Arg Asp Ile Leu Ser Ile Ser Asn Asp Ser
65              70              75              80

Lys Met Pro Ile Ser Glu Tyr Gly Ile Lys Lys Ile Asn Asn Thr Ile
            85              90              95

Lys Ala Ser Tyr Leu Asn Tyr Ala Lys Lys His Phe Asn Asn Leu Phe
            100             105             110

Asp Ile Lys Lys Val Asn Lys Asp Asn Phe Pro Lys Asn Ile Asp Ile
        115             120             125

Phe Thr Tyr Ser Phe Pro Cys Gln Asp Leu Ser Val Gln Gly Leu Gln
        130             135             140

Lys Gly Ile Asp Lys Glu Leu Asn Thr Arg Ser Gly Leu Leu Trp Glu
145             150             155             160

Ile Glu Arg Ile Leu Glu Glu Ile Lys Asn Ser Phe Ser Lys Glu Glu
            165             170             175

Met Pro Lys Tyr Leu Leu Met Glu Asn Val Lys Asn Leu Leu Ser His
            180             185             190

Lys Asn Lys Lys Asn Tyr Asn Thr Trp Leu Lys Gln Leu Glu Lys Phe
        195             200             205

Gly Tyr Lys Ser Lys Thr Tyr Leu Leu Asn Ser Lys Asn Phe Asp Asn
        210             215             220
```

```
Cys Gln Asn Arg Glu Arg Val Phe Cys Leu Ser Ile Arg Asp Asp Tyr
225                 230                 235                 240

Leu Glu Lys Thr Gly Phe Lys Phe Lys Glu Leu Glu Lys Val Lys Asn
                245                 250                 255

Pro Pro Lys Lys Ile Lys Asp Ile Leu Val Asp Ser Ser Asn Tyr Lys
                260                 265                 270

Tyr Leu Asn Leu Asn Lys Tyr Glu Thr Thr Thr Phe Arg Glu Thr Lys
                275                 280                 285

Ser Asn Ile Ile Ser Arg Pro Leu Lys Asn Tyr Thr Thr Phe Asn Ser
        290                 295                 300

Glu Asn Tyr Val Tyr Asn Ile Asn Gly Ile Gly Pro Thr Leu Thr Ala
305                 310                 315                 320

Ser Gly Ala Asn Ser Arg Ile Lys Ile Glu Thr Gln Gln Gly Val Arg
                325                 330                 335

Tyr Leu Thr Pro Leu Glu Cys Phe Lys Tyr Met Gln Phe Asp Val Asn
                340                 345                 350

Asp Phe Lys Lys Val Gln Ser Thr Asn Leu Ile Ser Glu Asn Lys Met
                355                 360                 365

Ile Tyr Ile Ala Gly Lys Ser Ile Pro Val Lys Ile Leu Glu Ala Ile
        370                 375                 380

Phe Asn Thr Leu Glu Phe Val Asn Asn Glu Glu Leu Glu His His His
385                 390                 395                 400

His His His
```

<210> SEQ ID NO 3
<211> LENGTH: 472
<212> TYPE: PRT
<213> ORGANISM: Artificial Sequence
<220> FEATURE:
<223> OTHER INFORMATION: Dcm N436K - no His tag

<400> SEQUENCE: 3

```
Met Gln Glu Asn Ile Ser Val Thr Asp Ser Tyr Ser Thr Gly Asn Ala
1                 5                   10                  15

Ala Gln Ala Met Leu Glu Lys Leu Leu Gln Ile Tyr Asp Val Lys Thr
                20                  25                  30

Leu Val Ala Gln Leu Asn Gly Val Gly Glu Asn His Trp Ser Ala Ala
        35                  40                  45

Ile Leu Lys Arg Ala Leu Ala Asn Asp Ser Ala Trp His Arg Leu Ser
        50                  55                  60

Glu Lys Glu Phe Ala His Leu Gln Thr Leu Leu Pro Lys Pro Pro Ala
65                  70                  75                  80

His His Pro His Tyr Ala Phe Arg Phe Ile Asp Leu Phe Ala Gly Ile
                85                  90                  95

Gly Gly Ile Arg Arg Gly Phe Glu Ser Ile Gly Gly Gln Cys Val Phe
                100                 105                 110

Thr Ser Glu Trp Asn Lys His Ala Val Arg Thr Tyr Lys Ala Asn His
                115                 120                 125

Tyr Cys Asp Pro Ala Thr His His Phe Asn Glu Asp Ile Arg Asp Ile
        130                 135                 140

Thr Leu Ser His Lys Glu Gly Val Ser Asp Glu Ala Ala Ala Glu His
145                 150                 155                 160

Ile Arg Gln His Ile Pro Glu His Asp Val Leu Leu Ala Gly Phe Pro
                165                 170                 175
```

-continued

```
Cys Gln Pro Phe Ser Leu Ala Gly Val Ser Lys Lys Asn Ser Leu Gly
            180                 185                 190

Arg Ala His Gly Phe Ala Cys Asp Thr Gln Gly Thr Leu Phe Phe Asp
            195                 200                 205

Val Val Arg Ile Ile Asp Ala Arg Arg Pro Ala Met Phe Val Leu Glu
            210                 215                 220

Asn Val Lys Asn Leu Lys Ser His Asp Gln Gly Lys Thr Phe Arg Ile
225                 230                 235                 240

Ile Met Gln Thr Leu Asp Glu Leu Gly Tyr Asp Val Ala Asp Ala Glu
                245                 250                 255

Asp Asn Gly Pro Asp Asp Pro Lys Ile Ile Asp Gly Lys His Phe Leu
            260                 265                 270

Pro Gln His Arg Glu Arg Ile Val Leu Val Gly Phe Arg Arg Asp Leu
            275                 280                 285

Asn Leu Lys Ala Asp Phe Thr Leu Arg Asp Ile Ser Glu Cys Phe Pro
            290                 295                 300

Ala Gln Arg Val Thr Leu Ala Gln Leu Leu Asp Pro Met Val Glu Ala
305                 310                 315                 320

Lys Tyr Ile Leu Thr Pro Val Leu Trp Lys Tyr Leu Tyr Arg Tyr Ala
                325                 330                 335

Lys Lys His Gln Ala Arg Gly Asn Gly Phe Gly Tyr Gly Met Val Tyr
            340                 345                 350

Pro Asn Asn Pro Gln Ser Val Thr Arg Thr Leu Ser Ala Arg Tyr Tyr
            355                 360                 365

Lys Asp Gly Ala Glu Ile Leu Ile Asp Arg Gly Trp Asp Met Ala Thr
            370                 375                 380

Gly Glu Lys Asp Phe Asp Asp Pro Leu Asn Gln Gln His Arg Pro Arg
385                 390                 395                 400

Arg Leu Thr Pro Arg Glu Cys Ala Arg Leu Met Gly Phe Glu Ala Pro
                405                 410                 415

Gly Glu Ala Lys Phe Arg Ile Pro Val Ser Asp Thr Gln Ala Tyr Arg
            420                 425                 430

Gln Phe Gly Lys Ser Val Val Val Pro Val Phe Ala Ala Val Ala Lys
            435                 440                 445

Leu Leu Glu Pro Lys Ile Lys Gln Ala Val Ala Leu Arg Gln Gln Glu
            450                 455                 460

Ala Gln His Gly Arg Arg Ser Arg
465                 470
```

```
<210> SEQ ID NO 4
<211> LENGTH: 478
<212> TYPE: PRT
<213> ORGANISM: Artificial Sequence
<220> FEATURE:
<223> OTHER INFORMATION: Dcm N436K with His tag

<400> SEQUENCE: 4
```

```
Met Gln Glu Asn Ile Ser Val Thr Asp Ser Tyr Ser Thr Gly Asn Ala
1               5                   10                  15

Ala Gln Ala Met Leu Glu Lys Leu Leu Gln Ile Tyr Asp Val Lys Thr
            20                  25                  30

Leu Val Ala Gln Leu Asn Gly Val Gly Glu Asn His Trp Ser Ala Ala
            35                  40                  45

Ile Leu Lys Arg Ala Leu Ala Asn Asp Ser Ala Trp His Arg Leu Ser
        50                  55                  60
```

-continued

```
Glu Lys Glu Phe Ala His Leu Gln Thr Leu Leu Pro Lys Pro Pro Ala
65              70              75              80

His His Pro His Tyr Ala Phe Arg Phe Ile Asp Leu Phe Ala Gly Ile
                85              90              95

Gly Gly Ile Arg Arg Gly Phe Glu Ser Ile Gly Gly Gln Cys Val Phe
            100             105             110

Thr Ser Glu Trp Asn Lys His Ala Val Arg Thr Tyr Lys Ala Asn His
        115             120             125

Tyr Cys Asp Pro Ala Thr His His Phe Asn Glu Asp Ile Arg Asp Ile
    130             135             140

Thr Leu Ser His Lys Glu Gly Val Ser Asp Glu Ala Ala Ala Glu His
145             150             155             160

Ile Arg Gln His Ile Pro Glu His Asp Val Leu Leu Ala Gly Phe Pro
                165             170             175

Cys Gln Pro Phe Ser Leu Ala Gly Val Ser Lys Lys Asn Ser Leu Gly
            180             185             190

Arg Ala His Gly Phe Ala Cys Asp Thr Gln Gly Thr Leu Phe Phe Asp
            195             200             205

Val Val Arg Ile Ile Asp Ala Arg Arg Pro Ala Met Phe Val Leu Glu
    210             215             220

Asn Val Lys Asn Leu Lys Ser His Asp Gln Gly Lys Thr Phe Arg Ile
225             230             235             240

Ile Met Gln Thr Leu Asp Glu Leu Gly Tyr Asp Val Ala Asp Ala Glu
                245             250             255

Asp Asn Gly Pro Asp Asp Pro Lys Ile Ile Asp Gly Lys His Phe Leu
            260             265             270

Pro Gln His Arg Glu Arg Ile Val Leu Val Gly Phe Arg Arg Asp Leu
            275             280             285

Asn Leu Lys Ala Asp Phe Thr Leu Arg Asp Ile Ser Glu Cys Phe Pro
    290             295             300

Ala Gln Arg Val Thr Leu Ala Gln Leu Leu Asp Pro Met Val Glu Ala
305             310             315             320

Lys Tyr Ile Leu Thr Pro Val Leu Trp Lys Tyr Leu Tyr Arg Tyr Ala
                325             330             335

Lys Lys His Gln Ala Arg Gly Asn Gly Phe Gly Tyr Gly Met Val Tyr
            340             345             350

Pro Asn Asn Pro Gln Ser Val Thr Arg Thr Leu Ser Ala Arg Tyr Tyr
            355             360             365

Lys Asp Gly Ala Glu Ile Leu Ile Asp Arg Gly Trp Asp Met Ala Thr
    370             375             380

Gly Glu Lys Asp Phe Asp Asp Pro Leu Asn Gln Gln His Arg Pro Arg
385             390             395             400

Arg Leu Thr Pro Arg Glu Cys Ala Arg Leu Met Gly Phe Glu Ala Pro
                405             410             415

Gly Glu Ala Lys Phe Arg Ile Pro Val Ser Asp Thr Gln Ala Tyr Arg
            420             425             430

Gln Phe Gly Lys Ser Val Val Val Pro Val Phe Ala Ala Val Ala Lys
            435             440             445

Leu Leu Glu Pro Lys Ile Lys Gln Ala Val Ala Leu Arg Gln Gln Glu
    450             455             460

Ala Gln His Gly Arg Arg Ser Arg His His His His His
465             470             475
```

```
<210> SEQ ID NO 5
<211> LENGTH: 100
<212> TYPE: DNA
<213> ORGANISM: Artificial Sequence
<220> FEATURE:
<223> OTHER INFORMATION: ss DNA spike in control for troubleshooting
<220> FEATURE:
<221> NAME/KEY: modified_base
<222> LOCATION: (45)..(45)
<223> OTHER INFORMATION: m5c
<220> FEATURE:
<221> NAME/KEY: modified_base
<222> LOCATION: (69)..(69)
<223> OTHER INFORMATION: m5c

<400> SEQUENCE: 5
tagtgttgat atgggttatg aatgaagtaa ggacgttgaa tagtcgagcc gtaggcgctg      60
tcgtaggacg agtgttaagg tatatgagta gatgattgat                          100

<210> SEQ ID NO 6
<211> LENGTH: 24
<212> TYPE: DNA
<213> ORGANISM: Artificial Sequence
<220> FEATURE:
<223> OTHER INFORMATION: 202mer F

<400> SEQUENCE: 6
ttgatatggg ttatgaatga agta                                            24

<210> SEQ ID NO 7
<211> LENGTH: 25
<212> TYPE: DNA
<213> ORGANISM: Artificial Sequence
<220> FEATURE:
<223> OTHER INFORMATION: 202mer R

<400> SEQUENCE: 7
tcatctactc atatacctta acact                                           25

<210> SEQ ID NO 8
<211> LENGTH: 202
<212> TYPE: DNA
<213> ORGANISM: Artificial Sequence
<220> FEATURE:
<223> OTHER INFORMATION: 202mer

<400> SEQUENCE: 8
ttgatatggg ttatgaatga agtagtcgat ctttcatcat attctagatc cctctgaaaa      60
aatcttccga gtttgctagg cagtgataca taactctttt ccaataattg gggaagtcat     120
tcaaatctat aataggtttc agatttaatt ctgactgtag ctgctgaaac gttgcggagt     180
gttaaggtat atgagtagat ga                                             202

<210> SEQ ID NO 9
<211> LENGTH: 17
<212> TYPE: DNA
<213> ORGANISM: Artificial Sequence
<220> FEATURE:
<223> OTHER INFORMATION: Lambda Amplicon F

<400> SEQUENCE: 9
gaaaaatggg tggatgg                                                    17

<210> SEQ ID NO 10
<211> LENGTH: 15
<212> TYPE: DNA
```

<213> ORGANISM: Artificial Sequence
<220> FEATURE:
<223> OTHER INFORMATION: Lambda Amplicon R

<400> SEQUENCE: 10
caccatcctc ttcct                                                                        15

<210> SEQ ID NO 11
<211> LENGTH: 16
<212> TYPE: PRT
<213> ORGANISM: Artificial Sequence
<220> FEATURE:
<223> OTHER INFORMATION: Dcm codon

<400> SEQUENCE: 11

Val Ser Asp Thr Gln Ala Tyr Arg Gln Phe Gly Asn Ser Val Val Val
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: M.Mpel Codon

<400> SEQUENCE: 12

Ile Ser Glu Asn Lys Met Ile Tyr Ile Ala Gly Asn Ser Ile Pro Val
1               5                   10                  15

<210> SEQ ID NO 13
<211> LENGTH: 29
<212> TYPE: PRT
<213> ORGANISM: Artificial Sequence
<220> FEATURE:
<223> OTHER INFORMATION: DNMT1 H. sapiens

<400> SEQUENCE: 13

Asn Ile Leu Asp Lys His Arg Gln Val Gly Asn Ala Val Pro Pro Pro
1               5                   10                  15

Leu Ala Lys Ala Ile Gly Leu Glu Ile Lys Leu Cys Met
            20                  25

<210> SEQ ID NO 14
<211> LENGTH: 29
<212> TYPE: PRT
<213> ORGANISM: Artificial Sequence
<220> FEATURE:
<223> OTHER INFORMATION: ORF86 R. pipens herpes virus

<400> SEQUENCE: 14

Ala Leu Leu Asp Val Tyr Lys Gln Val Gly Asn Ala Val Pro Pro Pro
1               5                   10                  15

Met Ala Arg Ala Ile Gly Leu Arg Ile Ala Ser Ala Leu
            20                  25

<210> SEQ ID NO 15
<211> LENGTH: 29
<212> TYPE: PRT
<213> ORGANISM: Artificial Sequence
<220> FEATURE:
<223> OTHER INFORMATION: Dmnt1 D. rerio

<400> SEQUENCE: 15

Asn Val Leu Asp Lys His Arg Gln Val Gly Asn Ala Val Pro Pro Pro
1               5                   10                  15

Leu Ser Glu Thr Ile Gly Leu Glu Val Lys Lys Cys Val
                20                  25

<210> SEQ ID NO 16
<211> LENGTH: 29
<212> TYPE: PRT
<213> ORGANISM: Artificial Sequence
<220> FEATURE:
<223> OTHER INFORMATION: zf(cxxc)-5 C. intestinalis

<400> SEQUENCE: 16

Ser Ile Leu Asp Lys His Arg Glu Val Gly Asn Ala Val Pro Pro Pro
1               5                   10                  15

Met Ser Lys Ala Ile Gly Leu Gln Ile Lys Lys Ser Leu
                20                  25

<210> SEQ ID NO 17
<211> LENGTH: 29
<212> TYPE: PRT
<213> ORGANISM: Artificial Sequence
<220> FEATURE:
<223> OTHER INFORMATION: Dnmt1 P.lividus

<400> SEQUENCE: 17

Ser Ile Leu Asp Lys His Arg Gln Ile Gly Asn Ala Val Pro Pro Pro
1               5                   10                  15

Met Ala Ala Ala Ile Gly Met Glu Ile Lys Val Cys Leu
                20                  25

<210> SEQ ID NO 18
<211> LENGTH: 29
<212> TYPE: PRT
<213> ORGANISM: Artificial Sequence
<220> FEATURE:
<223> OTHER INFORMATION: At4g08990 A.thaliana

<400> SEQUENCE: 18

Thr Thr Lys His Lys His Arg Gln Ile Gly Asn Ala Val Pro Pro Pro
1               5                   10                  15

Leu Ala Phe Ala Leu Gly Arg Lys Leu Lys Glu Ala Leu
                20                  25

<210> SEQ ID NO 19
<211> LENGTH: 29
<212> TYPE: PRT
<213> ORGANISM: Artificial Sequence
<220> FEATURE:
<223> OTHER INFORMATION: OsMET1-1 O.sativa

<400> SEQUENCE: 19

Asn Ile Gln Asn Lys His Arg Gln Ile Gly Asn Ala Val Pro Pro Pro
1               5                   10                  15

Leu Ala Tyr Ala Leu Gly Arg Lys Leu Lys Gln Ala Ile
                20                  25

<210> SEQ ID NO 20
<211> LENGTH: 29
<212> TYPE: PRT
<213> ORGANISM: Artificial Sequence
<220> FEATURE:
<223> OTHER INFORMATION: Dmt1 C. reinhardtii

<400> SEQUENCE: 20

Ser Val Ala Asp Cys Tyr Lys Gln Val Gly Asn Ala Val Pro Pro Pro
1               5                   10                  15

Leu Ala Leu Ala Leu Gly Leu Gln Leu Ser Gln Ala Leu
            20                      25

<210> SEQ ID NO 21
<211> LENGTH: 29
<212> TYPE: PRT
<213> ORGANISM: Artificial Sequence
<220> FEATURE:
<223> OTHER INFORMATION: Masc2 A.immersus

<400> SEQUENCE: 21

Gly Val Lys Lys Trp His Arg Asn Ile Gly Asn Ala Val Pro Val Pro
1               5                   10                  15

Leu Gly Glu Gln Ile Gly Arg Cys Ile Gly Tyr Ser Val
            20                      25

<210> SEQ ID NO 22
<211> LENGTH: 29
<212> TYPE: PRT
<213> ORGANISM: Artificial Sequence
<220> FEATURE:
<223> OTHER INFORMATION: Dim2 N.crassa

<400> SEQUENCE: 22

Arg Thr Thr Asp Gln Trp Lys Leu Val Gly Asn Ser Val Ser Arg His
1               5                   10                  15

Met Ala Leu Ala Ile Gly Leu Lys Phe Arg Glu Ala Trp
            20                      25

<210> SEQ ID NO 23
<211> LENGTH: 29
<212> TYPE: PRT
<213> ORGANISM: Artificial Sequence
<220> FEATURE:
<223> OTHER INFORMATION: CMT1 A.thaliana

<400> SEQUENCE: 23

Thr Ile Lys Glu Lys Tyr Ile Gln Val Gly Asn Ala Val Ala Val Pro
1               5                   10                  15

Val Gly Val Ala Leu Gly Tyr Ala Phe Gly Met Ala Ser
            20                      25

<210> SEQ ID NO 24
<211> LENGTH: 29
<212> TYPE: PRT
<213> ORGANISM: Artificial Sequence
<220> FEATURE:
<223> OTHER INFORMATION: Zmet5 Z.mays

<400> SEQUENCE: 24

Pro Ile Lys Glu Lys Tyr Ile Gln Val Gly Asn Ala Val Ala Val Pro
1               5                   10                  15

Val Ala Arg Ala Leu Gly Tyr Cys Leu Gly Gln Ala Tyr
            20                      25

<210> SEQ ID NO 25
<211> LENGTH: 29
<212> TYPE: PRT
<213> ORGANISM: Artificial Sequence
<220> FEATURE:
<223> OTHER INFORMATION: CMT3 A.thaliana

<400> SEQUENCE: 25

Pro Pro Lys Gln Lys Tyr Ile Gln Val Gly Asn Ala Val Ala Val Pro

```
1               5               10              15

Val Ala Lys Ala Leu Gly Tyr Ala Leu Gly Thr Ala Phe
            20              25

<210> SEQ ID NO 26
<211> LENGTH: 29
<212> TYPE: PRT
<213> ORGANISM: Artificial Sequence
<220> FEATURE:
<223> OTHER INFORMATION: CMT2 A.thaliana

<400> SEQUENCE: 26

Thr Ile Lys Glu Arg Tyr Cys Gln Ile Gly Asn Ala Val Ala Val Ser
1               5               10              15

Val Ser Arg Ala Leu Gly Tyr Ser Leu Gly Met Ala Phe
            20              25

<210> SEQ ID NO 27
<211> LENGTH: 27
<212> TYPE: PRT
<213> ORGANISM: Artificial Sequence
<220> FEATURE:
<223> OTHER INFORMATION: Masc1-related N.crassa

<400> SEQUENCE: 27

Asn Tyr Ile Lys Lys Gln Ile Gly Asn Ala Phe Pro Pro Ile Phe Val
1               5               10              15

Lys Leu Leu Tyr Lys His Leu Val Glu Cys Leu
            20              25

<210> SEQ ID NO 28
<211> LENGTH: 27
<212> TYPE: PRT
<213> ORGANISM: Artificial Sequence
<220> FEATURE:
<223> OTHER INFORMATION: rid N.tetrasperma

<400> SEQUENCE: 28

Ser Tyr Ile Lys Lys Gln Ile Gly Asn Ala Phe Pro Pro Ile Phe Val
1               5               10              15

Lys Leu Leu Tyr Lys His Leu Val Glu Cys Leu
            20              25

<210> SEQ ID NO 29
<211> LENGTH: 29
<212> TYPE: PRT
<213> ORGANISM: Artificial Sequence
<220> FEATURE:
<223> OTHER INFORMATION: Masc1 A.immersus

<400> SEQUENCE: 29

Thr Leu Thr Asp Lys Arg Arg Ile Ile Gly Asn Ala Val Pro Pro Pro
1               5               10              15

Leu Ser Ala Ala Ile Met Ser Thr Leu Arg Gln Trp Met
            20              25

<210> SEQ ID NO 30
<211> LENGTH: 28
<212> TYPE: PRT
<213> ORGANISM: Artificial Sequence
<220> FEATURE:
<223> OTHER INFORMATION: DmtA A.fumigatus

<400> SEQUENCE: 30
```

```
Ala Arg Glu Val Arg Arg Gln Ile Gly Asn Ala Val Pro Pro Ala Leu
1               5                   10                  15

Ser Lys Ala Ile Tyr Arg Glu Ile Ile Lys Ser Leu
            20                  25

<210> SEQ ID NO 31
<211> LENGTH: 29
<212> TYPE: PRT
<213> ORGANISM: Artificial Sequence
<220> FEATURE:
<223> OTHER INFORMATION: Dnmt2_P.berghei

<400> SEQUENCE: 31

Thr Asn Lys Gln Lys Tyr Lys Leu Ile Gly Asn Ser Val Asn Val Thr
1               5                   10                  15

Val Ile Ser Leu Ile Phe Gln Thr Tyr Asn Val Phe Lys
            20                  25

<210> SEQ ID NO 32
<211> LENGTH: 29
<212> TYPE: PRT
<213> ORGANISM: Artificial Sequence
<220> FEATURE:
<223> OTHER INFORMATION: CAD51016 P.falciparum

<400> SEQUENCE: 32

Thr Asp Arg Gln Lys Tyr Lys Leu Ile Gly Asn Ser Val Asn Val Ile
1               5                   10                  15

Val Ile Ser Tyr Ile Phe His Val His Asn Ile Phe Glu
            20                  25

<210> SEQ ID NO 33
<211> LENGTH: 28
<212> TYPE: PRT
<213> ORGANISM: Artificial Sequence
<220> FEATURE:
<223> OTHER INFORMATION: dDnmt2 D.melanogaster

<400> SEQUENCE: 33

Thr Asn Arg Gln Lys Tyr Arg Leu Leu Gly Asn Ser Ile Asn Val Lys
1               5                   10                  15

Val Val Gly Glu Leu Ile Lys Leu Leu Thr Ile Lys
            20                  25

<210> SEQ ID NO 34
<211> LENGTH: 29
<212> TYPE: PRT
<213> ORGANISM: Artificial Sequence
<220> FEATURE:
<223> OTHER INFORMATION: Pmt1 C.parvum

<400> SEQUENCE: 34

Asp Leu Lys Lys Gln Tyr Ser Leu Ile Gly Asn Ser Ile Ser Ile His
1               5                   10                  15

Ile Val Thr Ile Leu Leu His Phe Met Leu Glu Leu Leu
            20                  25

<210> SEQ ID NO 35
<211> LENGTH: 29
<212> TYPE: PRT
<213> ORGANISM: Artificial Sequence
<220> FEATURE:
<223> OTHER INFORMATION: OsJ_02581 O.sativa

<400> SEQUENCE: 35
```

Ser Leu Arg Gln Gln Tyr Ala Met Leu Gly Asn Ser Leu Ser Val Ala
1               5                   10                  15

Val Val Gly Pro Leu Leu Arg Tyr Leu Phe Ala Glu Thr
            20                  25

<210> SEQ ID NO 36
<211> LENGTH: 29
<212> TYPE: PRT
<213> ORGANISM: Artificial Sequence
<220> FEATURE:
<223> OTHER INFORMATION: pmt1 S.pombe

<400> SEQUENCE: 36

Thr Glu Lys Cys Met Tyr Arg Leu Leu Gly Asn Ser Ile Asn Val Lys
1               5                   10                  15

Val Val Ser Tyr Leu Ile Ser Leu Leu Leu Glu Pro Leu
            20                  25

<210> SEQ ID NO 37
<211> LENGTH: 29
<212> TYPE: PRT
<213> ORGANISM: Artificial Sequence
<220> FEATURE:
<223> OTHER INFORMATION: Dnmt2-like C.intestinalis

<400> SEQUENCE: 37

Thr Arg Lys Gln Lys Tyr Lys Leu Leu Gly Asn Ser Leu Asn Val Tyr
1               5                   10                  15

Val Val Ser Cys Leu Leu Lys Leu Leu Ile Thr Asp Thr
            20                  25

<210> SEQ ID NO 38
<211> LENGTH: 29
<212> TYPE: PRT
<213> ORGANISM: Artificial Sequence
<220> FEATURE:
<223> OTHER INFORMATION: Dnmt2-like P.patens

<400> SEQUENCE: 38

Ser Leu Lys Gln Arg Tyr Ala Leu Leu Gly Asn Ser Leu Ser Val Ala
1               5                   10                  15

Val Val Gly Val Leu Leu Arg Tyr Leu Phe Ser Glu Pro
            20                  25

<210> SEQ ID NO 39
<211> LENGTH: 29
<212> TYPE: PRT
<213> ORGANISM: Artificial Sequence
<220> FEATURE:
<223> OTHER INFORMATION: Dnmt2 A.mellifera

<400> SEQUENCE: 39

Thr Asp Lys Gln Lys Tyr Arg Leu Leu Gly Asn Ser Ile Asn Val Tyr
1               5                   10                  15

Val Val Ser Arg Leu Ile Phe Leu Leu Tyr Thr Glu Arg
            20                  25

<210> SEQ ID NO 40
<211> LENGTH: 28
<212> TYPE: PRT
<213> ORGANISM: Artificial Sequence
<220> FEATURE:
<223> OTHER INFORMATION: BmDnmt2 B.mori

```
<400> SEQUENCE: 40

Thr Arg Lys Gln Cys Tyr Arg Leu Leu Gly Asn Ser Val Asn Val Lys
1               5                   10                  15

Val Ile Ser Glu Leu Leu Gln Ile Leu Phe Asp Glu
            20                  25

<210> SEQ ID NO 41
<211> LENGTH: 27
<212> TYPE: PRT
<213> ORGANISM: Artificial Sequence
<220> FEATURE:
<223> OTHER INFORMATION: DNMT2 H.sapiens

<400> SEQUENCE: 41

Thr Val Lys Gln Arg Tyr Arg Leu Leu Gly Asn Ser Leu Asn Val His
1               5                   10                  15

Val Val Ala Lys Leu Ile Lys Ile Leu Tyr Glu
            20                  25

<210> SEQ ID NO 42
<211> LENGTH: 29
<212> TYPE: PRT
<213> ORGANISM: Artificial Sequence
<220> FEATURE:
<223> OTHER INFORMATION: Dnmt2 M.musculus

<400> SEQUENCE: 42

Thr Val Lys Gln Arg Tyr Arg Leu Leu Gly Asn Ser Leu Asn Val His
1               5                   10                  15

Val Val Ala Lys Leu Leu Thr Val Leu Cys Glu Gly Phe
            20                  25

<210> SEQ ID NO 43
<211> LENGTH: 28
<212> TYPE: PRT
<213> ORGANISM: Artificial Sequence
<220> FEATURE:
<223> OTHER INFORMATION: Dnmt2 D.rerio

<400> SEQUENCE: 43

Ser Phe Lys Gln Gln Tyr Arg Val Leu Gly Asn Ser Leu Asn Val His
1               5                   10                  15

Val Val Ser His Leu Ile Arg Leu Met Leu Ser Lys
            20                  25

<210> SEQ ID NO 44
<211> LENGTH: 28
<212> TYPE: PRT
<213> ORGANISM: Artificial Sequence
<220> FEATURE:
<223> OTHER INFORMATION: Dnmt2 A.thaliana

<400> SEQUENCE: 44

Ser Leu Arg Gln Arg Tyr Ala Met Leu Gly Asn Ser Leu Ser Val Ala
1               5                   10                  15

Val Val Ala Pro Leu Leu Arg Tyr Leu Phe Asp Ser
            20                  25

<210> SEQ ID NO 45
<211> LENGTH: 29
<212> TYPE: PRT
<213> ORGANISM: Artificial Sequence
<220> FEATURE:
<223> OTHER INFORMATION: Dnmt2-like G.sulfurreducens
```

<400> SEQUENCE: 45

Pro Leu Arg Lys Arg Trp Gln Leu Val Gly Asn Ser Leu Ser Val Ala
1               5                   10                  15

Ala Val Arg Glu Val Leu Arg Ala Leu Pro Leu Pro Ala
            20                  25

<210> SEQ ID NO 46
<211> LENGTH: 29
<212> TYPE: PRT
<213> ORGANISM: Artificial Sequence
<220> FEATURE:
<223> OTHER INFORMATION: Dnmt-2 P.pacificus

<400> SEQUENCE: 46

Thr Gln Lys Gln Val Tyr Arg Ala Leu Gly Asn Ser Val Asn Val Leu
1               5                   10                  15

Val Val Ser Lys Leu Leu Glu Arg Leu Leu Thr Leu Lys
            20                  25

<210> SEQ ID NO 47
<211> LENGTH: 29
<212> TYPE: PRT
<213> ORGANISM: Artificial Sequence
<220> FEATURE:
<223> OTHER INFORMATION: DnmA D.discoideum

<400> SEQUENCE: 47

Thr Thr Ile Gln Cys Tyr Arg Leu Ile Gly Asn Ser Leu Asn Val Lys
1               5                   10                  15

Ile Val Ser Glu Leu Leu Lys Val Leu Val Ser Pro Asn
            20                  25

<210> SEQ ID NO 48
<211> LENGTH: 29
<212> TYPE: PRT
<213> ORGANISM: Artificial Sequence
<220> FEATURE:
<223> OTHER INFORMATION: EhMeth E.histolytica

<400> SEQUENCE: 48

Thr Asp Lys Gln Gln Tyr Gln Cys Leu Gly Asn Ser Val Ser Cys Phe
1               5                   10                  15

Val Ile Ala Gln Leu Met Glu Tyr Leu Phe Asp Asp Leu
            20                  25

<210> SEQ ID NO 49
<211> LENGTH: 29
<212> TYPE: PRT
<213> ORGANISM: Artificial Sequence
<220> FEATURE:
<223> OTHER INFORMATION: Dnmt3 A.mellifera

<400> SEQUENCE: 49

Ser Ala Thr Lys Arg Gln Arg Leu Ile Gly Lys Ser Trp Ser Val Gln
1               5                   10                  15

Thr Leu Thr Ala Ile Phe Glu Ser Leu Cys Pro Phe Phe
            20                  25

<210> SEQ ID NO 50
<211> LENGTH: 29
<212> TYPE: PRT
<213> ORGANISM: Artificial Sequence
<220> FEATURE:

-continued

```
<223> OTHER INFORMATION: Dnmt3a C.intestinalis

<400> SEQUENCE: 50

Pro Arg Thr Gly Arg Leu Arg Ile Leu Gly Lys Ser Trp Ser Val Pro
1               5                   10                  15

Val Ile Lys His Ile Phe Ala Pro Leu Lys Asp Tyr Phe
            20                  25

<210> SEQ ID NO 51
<211> LENGTH: 29
<212> TYPE: PRT
<213> ORGANISM: Artificial Sequence
<220> FEATURE:
<223> OTHER INFORMATION: Dnmt5 D.rerio

<400> SEQUENCE: 51

Gly Arg Met Gln Arg Gln Arg Val Leu Gly Lys Ser Trp Ser Val Pro
1               5                   10                  15

Val Ile Arg His Leu Leu Ala Pro Leu Lys Asp Tyr Phe
            20                  25

<210> SEQ ID NO 52
<211> LENGTH: 29
<212> TYPE: PRT
<213> ORGANISM: Artificial Sequence
<220> FEATURE:
<223> OTHER INFORMATION: DNMT3b H.sapiens

<400> SEQUENCE: 52

Gly Arg Gly Ala Arg Gln Lys Leu Leu Gly Arg Ser Trp Ser Val Pro
1               5                   10                  15

Val Ile Arg His Leu Phe Ala Pro Leu Lys Asp Tyr Phe
            20                  25

<210> SEQ ID NO 53
<211> LENGTH: 29
<212> TYPE: PRT
<213> ORGANISM: Artificial Sequence
<220> FEATURE:
<223> OTHER INFORMATION: DNMT3a H.sapiens

<400> SEQUENCE: 53

Ser Arg Leu Ala Arg Gln Arg Leu Leu Gly Arg Ser Trp Ser Val Pro
1               5                   10                  15

Val Ile Arg His Leu Phe Ala Pro Leu Lys Glu Tyr Phe
            20                  25

<210> SEQ ID NO 54
<211> LENGTH: 29
<212> TYPE: PRT
<213> ORGANISM: Artificial Sequence
<220> FEATURE:
<223> OTHER INFORMATION: Dnmt3a M.musculus

<400> SEQUENCE: 54

Ser Arg Leu Ala Arg Gln Arg Leu Leu Gly Arg Ser Trp Ser Val Pro
1               5                   10                  15

Val Ile Arg His Leu Phe Ala Pro Leu Lys Glu Tyr Phe
            20                  25

<210> SEQ ID NO 55
<211> LENGTH: 29
<212> TYPE: PRT
<213> ORGANISM: Artificial Sequence
```

-continued

```
<220> FEATURE:
<223> OTHER INFORMATION: Dnmt3b M.musculus

<400> SEQUENCE: 55

Gly Arg Gly Ala Arg Gln Lys Leu Leu Gly Arg Ser Trp Ser Val Pro
1               5                   10                  15

Val Ile Arg His Leu Phe Ala Pro Leu Lys Asp Tyr Phe
            20                  25

<210> SEQ ID NO 56
<211> LENGTH: 29
<212> TYPE: PRT
<213> ORGANISM: Artificial Sequence
<220> FEATURE:
<223> OTHER INFORMATION: Dnmt3L M.musculus

<400> SEQUENCE: 56

Ala Gln Val Arg Ser Arg Ser Lys Leu Asp Ala Pro Lys Val Asp Leu
1               5                   10                  15

Leu Val Lys Asn Cys Leu Leu Pro Leu Arg Glu Tyr Phe
            20                  25

<210> SEQ ID NO 57
<211> LENGTH: 29
<212> TYPE: PRT
<213> ORGANISM: Artificial Sequence
<220> FEATURE:
<223> OTHER INFORMATION: DNMT3L H.sapiens

<400> SEQUENCE: 57

Ala Gln Asn Lys Gln Ser Ser Lys Leu Ala Ala Lys Trp Pro Thr Lys
1               5                   10                  15

Leu Val Lys Asn Cys Phe Leu Pro Leu Arg Glu Tyr Phe
            20                  25

<210> SEQ ID NO 58
<211> LENGTH: 29
<212> TYPE: PRT
<213> ORGANISM: Artificial Sequence
<220> FEATURE:
<223> OTHER INFORMATION: Zmet3 Z.mays

<400> SEQUENCE: 58

Ser Arg Thr Glu Arg Tyr Arg Ser Leu Gly Asn Ser Phe Gln Val Asp
1               5                   10                  15

Thr Val Ala Tyr His Leu Ser Val Leu Lys Asp Leu Phe
            20                  25

<210> SEQ ID NO 59
<211> LENGTH: 29
<212> TYPE: PRT
<213> ORGANISM: Artificial Sequence
<220> FEATURE:
<223> OTHER INFORMATION: DRM1 A.thaliana

<400> SEQUENCE: 59

Ser Thr Thr Asp Arg Tyr Lys Ser Leu Gly Asn Ser Phe Gln Val Asp
1               5                   10                  15

Thr Val Ala Tyr His Leu Ser Val Leu Lys Pro Leu Phe
            20                  25

<210> SEQ ID NO 60
<211> LENGTH: 29
<212> TYPE: PRT
```

```
<213> ORGANISM: Artificial Sequence
<220> FEATURE:
<223> OTHER INFORMATION: M.EcoKDcm

<400> SEQUENCE: 60

Ser Asp Thr Gln Ala Tyr Arg Gln Phe Gly Asn Ser Val Val Val Pro
1               5                   10                  15

Val Phe Ala Ala Val Ala Lys Leu Leu Glu Pro Lys Ile
            20                  25

<210> SEQ ID NO 61
<211> LENGTH: 29
<212> TYPE: PRT
<213> ORGANISM: Artificial Sequence
<220> FEATURE:
<223> OTHER INFORMATION: M.EcoRII

<400> SEQUENCE: 61

Ser Asp Thr Gln Ser Tyr Arg Gln Phe Gly Asn Ser Val Val Val Pro
1               5                   10                  15

Val Phe Glu Ala Val Ala Lys Leu Leu Glu Pro Tyr Ile
            20                  25

<210> SEQ ID NO 62
<211> LENGTH: 29
<212> TYPE: PRT
<213> ORGANISM: Artificial Sequence
<220> FEATURE:
<223> OTHER INFORMATION: M.SsoII

<400> SEQUENCE: 62

Ser Asp Thr Gln Ala Tyr Lys Gln Phe Gly Asn Ser Val Ala Val Pro
1               5                   10                  15

Val Ile Asn Ala Ile Ala Glu Lys Ile Ile Ser Thr Leu
            20                  25

<210> SEQ ID NO 63
<211> LENGTH: 29
<212> TYPE: PRT
<213> ORGANISM: Artificial Sequence
<220> FEATURE:
<223> OTHER INFORMATION: M.HpaII

<400> SEQUENCE: 63

Ser Asp Ala Ser Ala Tyr Lys Gln Phe Gly Asn Ser Val Ala Val Pro
1               5                   10                  15

Ala Ile Gln Ala Thr Gly Lys Lys Ile Leu Glu Lys Leu
            20                  25

<210> SEQ ID NO 64
<211> LENGTH: 29
<212> TYPE: PRT
<213> ORGANISM: Artificial Sequence
<220> FEATURE:
<223> OTHER INFORMATION: M.HhaI

<400> SEQUENCE: 64

Ser Thr Ser Gln Ala Tyr Lys Gln Phe Gly Asn Ser Val Val Ile Asn
1               5                   10                  15

Val Leu Gln Tyr Ile Ala Tyr Asn Ile Gly Ser Ser Leu
            20                  25

<210> SEQ ID NO 65
<211> LENGTH: 29
```

```
<212> TYPE: PRT
<213> ORGANISM: Artificial Sequence
<220> FEATURE:
<223> OTHER INFORMATION: M.HaeII

<400> SEQUENCE: 65

Pro Tyr Ser Gln Val Arg Lys Val Ala Gly Asn Ser Val Ser Val Pro
1               5                   10                  15

Val Ile Arg Ala Ile Ala Gly Ser Met Ile Asn Ser Leu
            20                  25

<210> SEQ ID NO 66
<211> LENGTH: 29
<212> TYPE: PRT
<213> ORGANISM: Artificial Sequence
<220> FEATURE:
<223> OTHER INFORMATION: M.MspI

<400> SEQUENCE: 66

Ser Arg Thr Gln Met Tyr Arg Gln Met Gly Asn Ser Val Val Val Pro
1               5                   10                  15

Val Val Thr Lys Ile Ala Glu Gln Ile Ser Leu Ala Leu
            20                  25

<210> SEQ ID NO 67
<211> LENGTH: 29
<212> TYPE: PRT
<213> ORGANISM: Artificial Sequence
<220> FEATURE:
<223> OTHER INFORMATION: M.Sau3AI

<400> SEQUENCE: 67

Pro Ile Lys Met Arg Tyr Phe Cys Met Gly Asn Ala Leu Val Val Pro
1               5                   10                  15

Leu Ile Thr Arg Ile Gly Asn Gln Ile Glu Lys Ile Asp
            20                  25

<210> SEQ ID NO 68
<211> LENGTH: 29
<212> TYPE: PRT
<213> ORGANISM: Artificial Sequence
<220> FEATURE:
<223> OTHER INFORMATION: M.NlaIV

<400> SEQUENCE: 68

Pro Lys Lys Asp Lys Tyr Asp Leu Leu Gly Asn Thr Val Ala Val Pro
1               5                   10                  15

Val Ile Lys Ala Val Ser Glu Arg Leu Leu His Thr Leu
            20                  25

<210> SEQ ID NO 69
<211> LENGTH: 29
<212> TYPE: PRT
<213> ORGANISM: Artificial Sequence
<220> FEATURE:
<223> OTHER INFORMATION: M.HgiEI

<400> SEQUENCE: 69

Asn Gln Ser Ala Asn Phe Arg Leu Ile Gly Asn Ser Val Ala Pro Pro
1               5                   10                  15

Val Ile Val Ala Leu Gly Lys Arg Leu Gln Cys Val Lys
            20                  25

<210> SEQ ID NO 70
```

```
<211> LENGTH: 29
<212> TYPE: PRT
<213> ORGANISM: Artificial Sequence
<220> FEATURE:
<223> OTHER INFORMATION: M.NgoAIII

<400> SEQUENCE: 70

Ala Trp Gly Glu Ala Met Arg Gln Ile Gly Asn Ala Val Pro Val Lys
1               5                   10                  15

Leu Ser Glu Ile Leu Gly Lys His Leu Met Gly Val Leu
            20                  25

<210> SEQ ID NO 71
<211> LENGTH: 29
<212> TYPE: PRT
<213> ORGANISM: Artificial Sequence
<220> FEATURE:
<223> OTHER INFORMATION: M.Hpy99III

<400> SEQUENCE: 71

Lys Glu Ser His Leu Leu Ser Gln Ala Gly Asn Ala Met Ser Val Asn
1               5                   10                  15

Val Ile Ala Ala Ile Ala Lys Gln Met Leu Lys Ala Phe
            20                  25

<210> SEQ ID NO 72
<211> LENGTH: 29
<212> TYPE: PRT
<213> ORGANISM: Artificial Sequence
<220> FEATURE:
<223> OTHER INFORMATION: M.LlaDII

<400> SEQUENCE: 72

Ser Asn Gly Arg Leu Tyr Lys Gln Ala Gly Asn Ser Val Val Val Pro
1               5                   10                  15

Val Ile Glu Arg Ile Ala Lys Asn Leu Ala Asp Thr Ile
            20                  25

<210> SEQ ID NO 73
<211> LENGTH: 29
<212> TYPE: PRT
<213> ORGANISM: Artificial Sequence
<220> FEATURE:
<223> OTHER INFORMATION: M.Phi3TI

<400> SEQUENCE: 73

Ser Asn Ser Gln Leu Tyr Lys Gln Ala Gly Asn Ser Ile Thr Val Ser
1               5                   10                  15

Val Leu Glu Ser Ile Phe Gln Glu Leu Ile His Thr Tyr
            20                  25

<210> SEQ ID NO 74
<211> LENGTH: 27
<212> TYPE: PRT
<213> ORGANISM: Artificial Sequence
<220> FEATURE:
<223> OTHER INFORMATION: M.SssI

<400> SEQUENCE: 74

Thr Glu Asn Gln Lys Ile Phe Val Cys Gly Asn Ser Ile Ser Val Glu
1               5                   10                  15

Val Leu Glu Ala Ile Ile Asp Lys Ile Gly Gly
            20                  25
```

```
<210> SEQ ID NO 75
<211> LENGTH: 29
<212> TYPE: PRT
<213> ORGANISM: Artificial Sequence
<220> FEATURE:
<223> OTHER INFORMATION: M.HgaIA

<400> SEQUENCE: 75

Pro Glu Ile Leu Ile Arg Gln Ile Ile Gly Glu Cys Ile Pro Pro Leu
1               5                   10                  15

Leu Ile Glu Asn Ile Thr Arg Glu Ile Phe Asn Glu Asn
            20                  25

<210> SEQ ID NO 76
<211> LENGTH: 27
<212> TYPE: PRT
<213> ORGANISM: Artificial Sequence
<220> FEATURE:
<223> OTHER INFORMATION: M.NmeBIA

<400> SEQUENCE: 76

Ser Glu Leu Leu Ile Arg Gln Cys Ile Gly Glu Ser Ile Pro Pro Leu
1               5                   10                  15

Leu Ile Lys Lys Ile Val Glu Arg Ile Gly Lys
            20                  25

<210> SEQ ID NO 77
<211> LENGTH: 29
<212> TYPE: PRT
<213> ORGANISM: Artificial Sequence
<220> FEATURE:
<223> OTHER INFORMATION: M.HgiDII

<400> SEQUENCE: 77

Lys Phe Lys Thr Val Ser Arg Gln Ile Gly Asn Ala Val Pro Val Ala
1               5                   10                  15

Leu Gly Arg Val Ile Ala Lys Ser Ile Lys Arg Phe Leu
            20                  25

<210> SEQ ID NO 78
<211> LENGTH: 29
<212> TYPE: PRT
<213> ORGANISM: Artificial Sequence
<220> FEATURE:
<223> OTHER INFORMATION: M.DdeI

<400> SEQUENCE: 78

Lys His Leu Ser Gln Tyr Gln Gln Ile Gly Asn Ala Val Pro Pro Leu
1               5                   10                  15

Leu Ala Gln Ala Leu Ala Glu Arg Ile Ser Trp Tyr Phe
            20                  25

<210> SEQ ID NO 79
<211> LENGTH: 29
<212> TYPE: PRT
<213> ORGANISM: Artificial Sequence
<220> FEATURE:
<223> OTHER INFORMATION: M.Alw26I

<400> SEQUENCE: 79

Asn Lys Lys Asp Val Leu Thr Gln Ile Gly Asn Ala Val Pro Cys Leu
1               5                   10                  15

Phe Ala Gln Ala Ile Gly Ser Arg Leu Lys Glu Ile Val
            20                  25
```

-continued

```
<210> SEQ ID NO 80
<211> LENGTH: 29
<212> TYPE: PRT
<213> ORGANISM: Artificial Sequence
<220> FEATURE:
<223> OTHER INFORMATION: M.BssHII

<400> SEQUENCE: 80

Ser Leu Thr Ser Thr Gln Met Gln Val Gly Asn Ala Val Pro Val Gln
1               5                   10                  15

Leu Ala Lys Ala Val Phe Glu Ala Val Leu Ile Ser Val
            20                  25

<210> SEQ ID NO 81
<211> LENGTH: 29
<212> TYPE: PRT
<213> ORGANISM: Artificial Sequence
<220> FEATURE:
<223> OTHER INFORMATION: M.NspI

<400> SEQUENCE: 81

Thr Met Lys Lys Ala Met Trp Gln Ile Gly Asn Ala Val Pro Pro Arg
1               5                   10                  15

Leu Ala Glu Cys Ile Gly Tyr Ala Leu Ile Pro Tyr Leu
            20                  25

<210> SEQ ID NO 82
<211> LENGTH: 29
<212> TYPE: PRT
<213> ORGANISM: Artificial Sequence
<220> FEATURE:
<223> OTHER INFORMATION: M.AvaVIII

<400> SEQUENCE: 82

Thr Lys Trp His Gly Phe Arg Gln Val Gly Asn Ser Val Pro Pro Leu
1               5                   10                  15

Leu Ala Lys Ala Val Ala Arg Glu Ile Ile Arg Arg Leu
            20                  25

<210> SEQ ID NO 83
<211> LENGTH: 29
<212> TYPE: PRT
<213> ORGANISM: Artificial Sequence
<220> FEATURE:
<223> OTHER INFORMATION: M.HgiDI

<400> SEQUENCE: 83

Thr Lys Ser Glu Gln Glu Gln Met Ile Gly Asn Ala Val Pro Val Asn
1               5                   10                  15

Leu Ala Phe Phe Leu Ala Thr Ser Leu Gln Ala Tyr Leu
            20                  25

<210> SEQ ID NO 84
<211> LENGTH: 29
<212> TYPE: PRT
<213> ORGANISM: Artificial Sequence
<220> FEATURE:
<223> OTHER INFORMATION: M.HaeIII

<400> SEQUENCE: 84

Ser Leu Asn Asp Gly Tyr Lys Met Ile Gly Asn Ala Val Pro Val Asn
1               5                   10                  15

Leu Ala Tyr Glu Ile Ala Lys Thr Ile Lys Ser Ala Leu
            20                  25
```

-continued

```
<210> SEQ ID NO 85
<211> LENGTH: 29
<212> TYPE: PRT
<213> ORGANISM: Artificial Sequence
<220> FEATURE:
<223> OTHER INFORMATION: M.BsuRI

<400> SEQUENCE: 85

Arg Leu Asp Lys Gln Tyr Lys Gln Ile Gly Asn Ala Val Pro Val Leu
1               5                   10                  15

Leu Ala Lys Ala Val Ala Ser Pro Ile Ala Asn Trp Ala
            20                  25

<210> SEQ ID NO 86
<211> LENGTH: 29
<212> TYPE: PRT
<213> ORGANISM: Artificial Sequence
<220> FEATURE:
<223> OTHER INFORMATION: M.MthTI

<400> SEQUENCE: 86

Asn Val Ala Asp Gly Tyr Thr Met Val Gly Asn Ala Val Pro Val Lys
1               5                   10                  15

Leu Ala Glu Glu Leu Ala Lys Lys Ile Lys Lys Asp Leu
            20                  25

<210> SEQ ID NO 87
<211> LENGTH: 29
<212> TYPE: PRT
<213> ORGANISM: Artificial Sequence
<220> FEATURE:
<223> OTHER INFORMATION: M.Phi3TII

<400> SEQUENCE: 87

Ser Leu Thr Ala Gln Tyr Arg Ile Val Gly Asn Gly Ile Ala Ser Arg
1               5                   10                  15

Val Ala Trp Tyr Ile Gly Arg Ala Val Ala Asp Gln Leu
            20                  25

<210> SEQ ID NO 88
<211> LENGTH: 29
<212> TYPE: PRT
<213> ORGANISM: Artificial Sequence
<220> FEATURE:
<223> OTHER INFORMATION: M.BsrFI

<400> SEQUENCE: 88

Pro Leu Asp Lys Met Phe Lys Met Val Ser Asn Gly Val Pro Tyr Lys
1               5                   10                  15

Leu Ala Phe Leu Leu Ala Arg Gln Ile Lys Lys Val Leu
            20                  25

<210> SEQ ID NO 89
<211> LENGTH: 29
<212> TYPE: PRT
<213> ORGANISM: Artificial Sequence
<220> FEATURE:
<223> OTHER INFORMATION: M.SinI

<400> SEQUENCE: 89

Lys Leu Leu Asp Lys Tyr Arg Gln Leu Gly Asn Ala Val Pro Ile Gly
1               5                   10                  15

Leu Gly Leu Ala Val Gly Lys Asn Ile Leu Asp His Met
```

-continued

```
          20                    25

<210> SEQ ID NO 90
<211> LENGTH: 29
<212> TYPE: PRT
<213> ORGANISM: Artificial Sequence
<220> FEATURE:
<223> OTHER INFORMATION: M.Sau96I

<400> SEQUENCE: 90

Gly Val Gly Ala Gln Tyr Arg Gln Ile Gly Asn Ala Val Pro Val Asn
1               5                   10                  15

Leu Ala Lys Tyr Ile Gly Lys Ser Leu Val His Tyr Leu
            20                  25

<210> SEQ ID NO 91
<211> LENGTH: 29
<212> TYPE: PRT
<213> ORGANISM: Artificial Sequence
<220> FEATURE:
<223> OTHER INFORMATION: M.CviAIV

<400> SEQUENCE: 91

Tyr Ala Thr Lys Cys Pro Arg Thr Leu Thr Lys Arg Val Ser Lys Met
1               5                   10                  15

Leu Ala Ala Cys Val Gly Phe Ser Glu Gly Gly Asp Lys
            20                  25
```

COMPOSITIONS AND METHODS FOR DNA CYTOSINE CARBOXYMETHYLATION

CROSS REFERENCE TO RELATED APPLICATION

This application is a § 371 of International Application No, PCT/US2021/033169, filed May 19, 2021, which claims priority to U.S. Provisional Application No. 63/027,254 filed May 19, 2020, the entire disclosure of each being incorporated herein by reference as though set forth in full.

GRANT STATEMENT

This invention was made with government support under HG009545 and HG010646 awarded by the National Institutes of Health. The government has certain rights in the invention.

INCORPORATION-BY-REFERENCE OF MATERIAL SUBMITTED IN ELECTRONIC FORM

Incorporated herein by reference in its entirety is the Sequence Listing submitted via EFS-Web as a text file named SEQLIST.txt, created on May 19, 2021 and having a size of 45,719 bytes.

FIELD OF THE INVENTION

This invention relates to the fields of molecular biology, gene sequencing, and identification of epigenetic modifications in target nucleic acids. More specifically, the invention provides enzymes that can generate a novel DNA modification and associated processes which enable differentiation of cytosine, 5-methylcytosine and 5-hydroxymethylcytosine in DNA containing CpG regions of interest.

BACKGROUND OF THE INVENTION

Several publications and patent documents are cited throughout the specification in order to describe the state of the art to which this invention pertains. Each of these citations is incorporated herein by reference as though set forth in full.

Within the natural realm, an array of different DNA modifications have been described, but the vast majority of this diversity is confined to bacteriophage genomes and their prokaryotic hosts. Modifications to all canonical nucleobases have been described in phage, and these are accessed either by rewiring of biosynthetic pathways for dNTP pools or by hypermodification after incorporation into DNA (Weigele and Raleigh, 2016). In prokaryotes, the predominant modifications are found at the N6 position of adenine and either the N4 or C5 position of cytosine. Methylation of these bases serves rudimentary immune functions, primarily as a means to distinguish self from non-self in the arms race against bacteriophages (Nabel et al., 2012; Wilson and Murray, 1991), although emerging models suggest that some modifications may impact genome regulation (Sanchez-Romero and Casadesús, 2020).

5-methylcytosine (5mC) is a genomic DNA modification that extends from prokaryotes to higher organisms. While the precise evolutionary trajectory remains to be resolved, phylogenetic evidence shows that DNA cytosine methyltransferases (MTases), the enzymes responsible for the creation of 5mC, are conserved from prokaryotic restriction-modification systems to eukaryotic gene regulatory machinery (Iyer et al., 2011). In mammals, 5mC generation is predominantly confined to cytosine-guanine (CpG) dinucleotides, and this modification provides a readable handle within the major groove of DNA for modification-sensitive DNA binding proteins to modulate gene expression (Portela and Esteller, 2010). Adding further complexity to this model, 5mC was recently discovered to be a substrate for the Ten-Eleven Translocation (TET) family enzymes, which iteratively oxidize 5mC to create 5-hydroxymethyl-, 5-formyl-, and 5-carboxylcytosine (He et al., 2011; Ito et al., 2011; Tahiliani et al., 2009). While predominantly implicated as intermediates towards 5mC erasure, the potential independent epigenetic identities of oxidized 5mC bases are the subject of numerous provocative hypotheses (Bilyard et al., 2020). Across phylogeny, there is therefore compelling evidence for a functional role for diverse DNA modifications, providing the motivation for understanding the mechanisms by which new DNA modifications can arise.

The ability to generate novel DNA modifications, either not previously reported or not occurring in nature, offers opportunities for understanding the nature and composition of genomic DNA, but also readily allows for biotechnological applications. In particular, DNA modifications that are orthogonal to nature can be used as molecular biology handles for marking distinctive parts of DNA, such as particular sequences, whether the chromatin is open or closed, whether it was generated in vivo or in vitro, or the epigenetic modification state, as discussed next.

As noted above, modifications to genomic cytosine bases, mostly in cytosine-guanine dinucleotide (CpG) contexts, are critical to development, differentiation and pluripotency. As these modifications shape gene expression, determining their location via epigenetic DNA sequencing has been critical to revealing new biology, including efforts to define complexity at the single-cell level in tissues like the brain that exhibit remarkable cellular diversity. For decades, the 'gold' standard for epigenetic sequencing has been bisulfite-based sequencing (BS-Seq) technologies, which permitted identification of 5-methylcytosine (5mC), a marker associated with silencing. Bisulfite catalyzes the chemical deamination of unmodified cytosine, which reads as a C to T transition in sequencing, but bisulfite does not readily react with 5mC. Unbeknownst to the field, however, BS-Seq was in fact confounding 5mC signals with 5-hydroxymethylcytosine (5hmC), the product of TET-mediated oxidation of 5mC. 5hmC is particularly enriched in the neuronal genome, where its levels can reach as high as 40% of that of 5mC. While approaches have since been adapted to distinguish 5mC and 5hmC, these approaches continue to rely on bisulfite and have therefore constrained epigenetic DNA profiling from achieving its potential. Most notably, chemical deamination requires harsh, destructive pH and temperature conditions, which can introduce abasic sites that inevitably fragment input DNA. Sparse genomic sampling offers a solution that can still yield insights, but significant limitations remain: the majority of the genome is unmapped in single-cell or low-input settings, and extended length reads are unable to be reliably obtained due to damage. In addition to the confounding of 5mC and 5hmC, another major challenge is that modifications are analyzed "indirectly". It is the absence of reaction with bisulfite that marks these modified bases and no sequencing-based methodology currently directly sequences 5mC alone via its conversion to another base.

SUMMARY OF THE INVENTION

In accordance with the invention, an isolated recombinant methyltransferase variant enzyme having carboxymethyltransferase activity is provided. The enzyme variant has been modified to catalyze formation of 5-carboxymethylcytosine employing CxSAM as a substrate, via replacement of the existing polar amino acid at the native active site with a positively charged amino acid which binds adjacent to carbon 5 of a target cytosine in a polynucleotide of interest. In certain embodiments, the polar amino acid is selected from Asn, Gln, Glu, and Asp and the positively charged amino acid is Lys or Arg. In another embodiment, 5hmC present in the polynucleotide is optionally glucosylated. In a particularly preferred embodiment, the methyltransferase enzyme is a variant M.MpeI having SEQ ID NO: 1 or a sequence at least 90% identical thereto. In another embodiment, the methyltransferase enzyme is a variant of M.MpeI having an N374R substitution. In yet another aspect, methyltransferase enzyme is a variant of Dcm having SEQ ID NO: 3 or a sequence at least 90% identical thereto. In other aspects, the methyltransferase of SEQ ID NO: 1 can further comprise one or more amino acid substitutions selected from a) substitution of one or both residues T300 and E305 with S, A, G, Q, D, or N; b) substitution of one or more residues A323, N306, and Y299 with a positively charged amino acid selected from K, R or H; and c) substitution of S323 with A, G, K, R or H, thereby enhancing the activity of the enzyme. Finally, the enzyme variant can be a variant shown in FIG. 11B, where the active site has been modified, thereby conferring carboxymethlytransferase activity. The invention also encompasses vectors encoding each of the recombinant methyltransferases described herein. Also within the scope of the invention are host cells comprising the vectors described above. Expression of the recombinant methyltransferase in host cells naturally containing or exposed to CxSAM enables the generation of 5-carboxymethylcytosine in the host cell genome.

In yet another aspect of the invention, a direct method for localizing 5mC modifications in the genome which accurately profiles the methylome is provided. An exemplary method entails resolving unmethylated cytosine (C), 5-methylcytosine (5mC) and 5-hydroxymethylcytosine (5hmC) in a polynucleotide sample by a) reacting a polynucleotide optionally containing C, 5mC, and/or 5hmC with a variant methyltransferase in the presence of carboxy-S-adenosyl-L-methionine (CxSAM) substrate, thereby labeling any unmodified C in said polynucleotide and rendering it resistant to deaminase action; b) contacting the polynucleotide above with a deaminase which deaminates 5mC and/or 5hmC, with minimal damage to said target polynucleotide present in said sample; and c) sequencing the deaminated polynucleotide sample, thereby identifying each of unmodified C, 5mC, and 5hmC present in said polynucleotide. In certain embodiments, the polynucleotides in the sample are fragmented or sheared prior to step a), and sequence adapters containing modified cytosines resistant to deamination, such as 5pyC, are operably linked to said sheared or fragmented polynucleotide. In other embodiments, the sample of step b) is amplified prior to the sequencing of step c). In preferred embodiments of the invention, the variant methyltransferase is a recombinant M.MpeI N374K and the deaminase enzyme is APOBEC3A. The polynucleotide sample can be from any source and in certain aspects, comprises genomic DNA, cancer cell DNA, cell free DNA or DNA in maternal circulation. The method can also optionally include methylated control polynucleotides. In other embodiments, the method can further comprise the step of comparing results obtained with those obtained using bisulfite dependent 5mC localization and ACE-seq 5hmC localization.

In a further embodiment of the invention, a kit for practicing the methods described above are provided. In one aspect, the kit comprising a variant M.MpeI methyltransferase of SEQ ID NO: 1 or SEQ ID NO: 2 or a sequence having at least 90% identity to either sequence over the active site motif, and CxSAM. In yet another aspect, the kit further comprises a cytosine deaminase enzyme which can be the deaminase enzyme, APOBEC3A. The kit of the invention can further comprise reagents and materials for cleaving or shearing DNA. In yet another approach the kit can further comprise comprising reagents for amplification of DNA.

The invention also provides a method for identifying S-adenosyl-methionine (SAM) analogs such as CxSAM which render cytosine residues present in a polynucleotide resistant to deaminase action. An exemplary method entails reacting a polynucleotide containing C, 5mC, and/or 5hmC with a variant methyltransferase in the presence of said analog substrate; contacting said polynucleotides with a deaminase and isolating polynucleotides comprising modified C residues which are resistant to deaminase action, thereby identifying said SAM analog.

BRIEF DESCRIPTION OF THE DRAWINGS

FIG. 1: Mechanism of DNA Cytosine Methyltransferases.

Figure 2B:
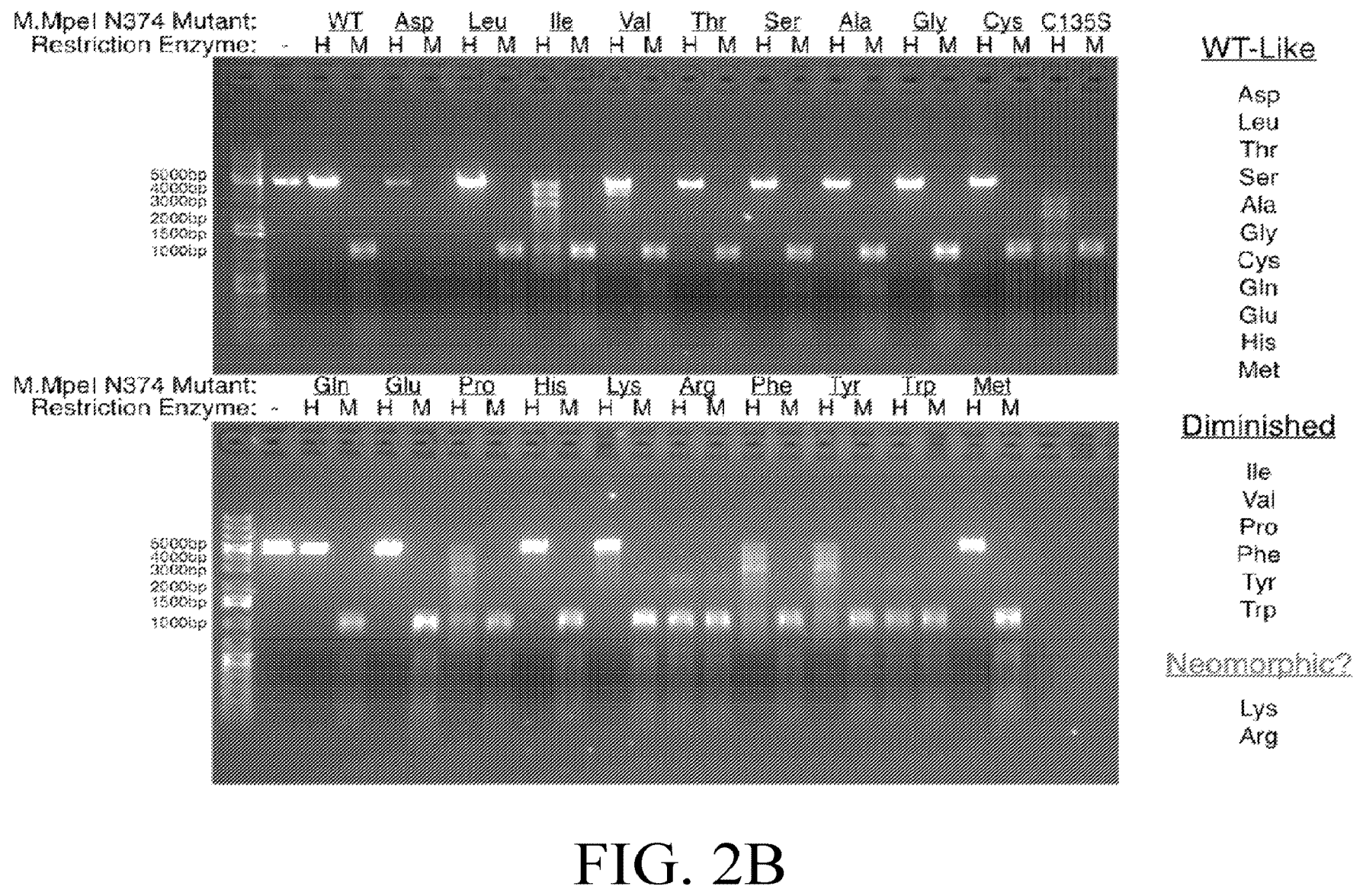

FIGS. 2A-2C: Saturation mutagenesis of M.MpeI N374X shows activity inconsistent with methylation. FIG. 2A) M.MpeI N374 may be involved in the final elimination step of cytosine methylation given its position adjacent to carbon 5 of the target cytosine. FIG. 2B) Restriction enzyme screen for methylation status of each of the M.MpeI N374X and C135S mutants. Each M.MpeI variant can potentially methylate their encoding plasmids in vivo. After plasmid isolation, the DNA is digested with HpaII ("H", modification-sensitive) and MspI ("M", methylation-insensitive). Based on this experiment, each N374X mutant is categorized into one of three categories, WT-like, diminished, or neomorphic. The red arrow shows MspI digestion bands inconsistent with methylation. FIG. 2C) Plasmid map of pMG81-M.MpeI with all HpaII/MspI (CCGG) sites visualized. The red R shows the protection event necessary to yield the newly resolved MspI resistant band. Notably, the unexpected modification could occur at any of the MspI sites shown; however, the site marked is the only easily resolvable fragment unless consecutive protection events have occurred on the same plasmid molecule.

FIG. 3A) Experimental design. Individual M.MpeI N374X constructs were transformed and maintained as separate cultures. In vivo methylation of plasmid DNA was then detected by both a restriction enzyme assay (FIG. 2) and nucleoside LC-MS/MS. Restriction enzyme recognition sites are visualized here which detect methylation (m) and an unknown modification (red R). FIG. 3B) Qualitative LC-MS/MS detection of a potential new DNA modification with distinct retention time and m/z in N374K but not WT M.MpeI plasmids. These peaks are normalized for maximal detection. FIG. 3C) In vivo synthesis of CxSAM by CmoA could provide a substrate for cytosine carboxymethylation. FIG. 3D) 5cxmC is derived exclusively from CmoA synthesis of CxSAM. Shown is the %5cxmC relative to total CpGs with each M.MpeI variant in cmoA$^+$ or ΔcmoA E. coli strains. Graphs show mean±s.d. (n=2 biological replicates). **limit of detection=0.26 fmol.

FIG. 6A) Enzyme preps used. All preps were quantified using a BSA standard curve and SDS-PAGE+Coomassie Blue staining. Normalized protein is shown here separated on a 10% SDS polyacrylamide gel and visualized with Coomassie Blue. FIG. 6) Chemical synthesis of CxSAM. Shown are traces for the LC-MS ESI+ Total Ion Current (TIC) signal with observed mass of 443.5 and HPLC purification of CxSAM showing a single UV 260 nm peak. In addition to the trace shown, HRMS was also obtained, identifying a mass of 443.1360 (mDa=−0.2, PPM=−0.5, Theoretical Mass: 443.1343).

FIGS. 7A-7D. M.MpeI N374K creates 5-carboxymethylcytosine (5cxmC) in vitro. FIG. 7A) pUC19 plasmid DNA (unmodified substrate) was incubated with excess of SAM or CxSAM and serial dilutions of M.MpeI to yield methylated or carboxymethylated DNA (modified product). The negative control lane (*) contains the highest concentration of M.MpeI enzyme with no SAM or CxSAM substrate. Challenge with the modification-sensitive restriction enzyme HpaII (CCGG) fragments only unmodified DNA, allowing for qualitative visualization of substrate vs product. M.MpeI N374K transfers both CxSAM and SAM in vitro while M.MpeI WT only transfers SAM. FIG. 7B) M.MpeI N374K quantitatively prefers CxSAM over SAM in an oligonucleotide assay shown in FIG. 8 (n=3 independent replicates). FIG. 7C) Mechanism of DNA carboxymethylation visualizing a π-system which is favorable for CxSAM electrophilicity. Catalytic residues E184 and C135 in M.MpeI are highlighted in addition to the adjacent N374K residue (blue) which could form a gain-of-function salt bridge (dashed-line) with the carboxylate (red) of CxSAM. FIG. 7D) Structural visualization of M.MpeI active site with same highlighted elements as in FIG. 7C. Cytosine is shown as 5-fluorocytosine (5flC). The image was obtained by manually overlaying CxSAM from PDB 4QNV and M.MpeI-bound SAH from PDB 4DKJ.

FIG. 8A) M.MpeI N374K was incubated with excess SAM or CxSAM and a hemimethylated CpG substrate containing a fluorophore label as shown. ESI-MS was obtained to confirm carboxymethylation of the hemimethylated substrate (expected: 8877.9, observed: 8876.7). HpaII digest was used to visualize total modification of the top strand after bottom strand exchange. FIG. 8B) Representative oligonucleotide assay gels. FIG. 8C) Enzyme dilution curve showing quantitative relative activities of M.MpeI WT and N374K towards SAM and CxSAM. Points represent mean±s.e. (n=3 independent replicates). EC$_{50}$ values were calculated, and 95% Confidence Intervals are reported in brackets.

FIG. 10A) Dcm (SEQ ID NO: 11) aligns with M.MpeI (SEQ ID NO: 12). This Dcm codon 436 can be mutated to yield a lysine. FIG. 10B) Qualitative nucleoside LC-MS/MS showing that Dcm N436K can carboxymethylate E. coli genomic DNA in vivo. These peaks are normalized for maximal detection. FIG. 10C) Quantitative 5cxmC LC-MS/MS signal in Dcm mutants. Shown is the %5cxmC relative to total CCWGGs with each Dcm variant (W=A or T, null=no plasmid). Error bars represent mean±s.d. (n=3 biological replicates). **limit of detection=0.26 fmol.

FIGS. 11A-11B. Neomorphic Dcm offers a new route to non-canonical nucleobase incorporation in the genome. Canonical nucleobases include A, C, G, and T, which are derived from native dNTP pools. FIG. 11A) Chemical synthesis and exogenous dXTPs can be delivered into E. coli for the replication of entirely unnatural base pairs in vivo. E. coli can be engineered to accept naturally-occurring nucleoside triphosphates (e.g. 5hmCTPs) by importing biosynthetic machinery derived from bacteriophages (i.e. non-native). 5-carboxymethylcytosine (5cxmC) in DNA, synthesized by a neomorphic DNA-modifying enzyme, has not been previously isolated or described. 5cxmC is thus a new, unnatural DNA base, derived from the native base cytosine and native metabolite CxSAM. Notably, this modification does not require manipulation of native dNTP pools. FIG. 11B) Multiple sequence alignment of cytosine methyltransferases across multiple phyla reveal a common motif which can be altered to confer carboxymethyltransferase activity. (SEQ ID NOs: 13-91 are shown in descending order) The figure shows a number of cytosine methyltransferases highlighting the motif of interest. Dcm is also labelled and described here as M.EcoKDcm. The arrow highlights the amino acid, which is most commonly Asn (N), within Motif X that could be putatively mutated to a K or R. Figure adapted from the following reference. (On the Evolutionary Origin of Eukaryotic DNA Methyltransferases and Dnmt2 Tomasz P. Jurkowski, Albert Jeltsch, PLoS ONE 2011, on the world wide web at doi.org/10.1371/journal.pone.0028104).

FIG. 12A) DNA cytosine modifications shape cellular fate and function. 5mC is the most prevalent cytosine modification. 5hmC has independent epigenetic identity and also serves as an intermediate in DNA demethylation. Localizing each modification at base resolution is critical to understanding function. FIG. 12B) Traditional sequencing approaches can localize 5mC+5hmC or 5hmC alone, but depend upon chemical deamination with bisulfite which is destructive. ACE-Seq is an enzymatic method for localizing 5hmC. DM-Seq is a novel method that newly allows for specific recognition of 5mC alone.

FIGS. 15A-15C. Structural rationalization for 5pyC and 5cxmC protection from deamination. FIG. 15A) Shown is the structure of APOBEC3A (PDB 5SWW) bound to ssDNA with the insert showing a "zoom in" of the active site. The target cytosine base is shown in yellow. An active site Tyr residue (purple) resides adjacent to the C5-C6 face of the base and provides a steric as well as hydrophobic gate that can potentially prevent deamination of some 5-position modified cytosine bases by A3A. FIG. 15B) Homogenously modified ssDNA substrates with all Cs replaced with the indicated modified structure were generated by LATE-PCR, purified and then treated with A3A. The deaminated products were subsequently PCR amplified and TA cloned before Sanger sequencing. Each data point shows an individual TA clone where percent C to T conversions out of total Cs are plotted on the y-axis. Both 5pyC and 5caC undetectable levels of deamination. FIG. 15C) genomic DNA was treated with M.MpeI N374K and SAM or CxSAM. Subsequent CpG modified DNA was deaminated with Bisulfite (BS) or A3A. % Cytosine calls at CpGs sites show protection of a modified cytosine from BS or A3A. By directly comparing the BS and A3A bars within the same condition, it is shown that 5mC is well transferred but not protected from deamination by A3A while 5cxmC is both transferred and protected from A3A deamination, possibly due to the size and charge of the 5-carboxymethyl substituent, which may not be accommodated by the active site Tyr's steric and hydrophobic gate.

FIGS. 16A-16B. M.MpeI N374K is a neomorphic CxMTase that is suitable for DM-Seq. pUC19 DNA is incubated with M.MpeI WT or N374K (NK) and SAM or CxSAM. Bisulfite sequencing assesses for modified cytosines. FIG. 16A) WT M.MpeI can quantitatively transfer SAM but not CxSAM. M.MpeI N374K can efficiently transfer both SAM HO %) and CxSAM (~70%) by next generation sequencing. FIG. 16B) Qualitative visualization of reads containing all modified CpGs after bisulfite conversion. The lower panel shows a zoomed in view of reads where all CpG sites are detected as modified CpGs (red).

FIG. 17A) Unmodified lambda phage genomic DNA methylated at CpG sides was used to confirm DM-Seq fidelity. Sheared genomic DNA was ligated with adaptors protected from deamination. Given the preference of the CxMTase for introducing a 5cxmC when the opposite strand contains a 5mC, the template DNA stand was copied with Klenow polymerase (exo-) using 5mdCTP in lieu of dCTP. The DNA was the treated with the N374K M.MpeI and either no SAM, normal SAM or CxSAM, followed by enzymatic deamination and library construction. FIG. 17B). At left is shown that bisulfite demonstrates CpG protection when SAM or CxSAM are used as substrates. At right is shown the fact that 5mC, generated with SAM, are deaminated by A3A, while the 5cxmC are specifically protected from deamination, highlighting the fidelity of DM-Seq in direct methylation sequencing.

DETAILED DESCRIPTION OF THE INVENTION

Figures 1, 2A:
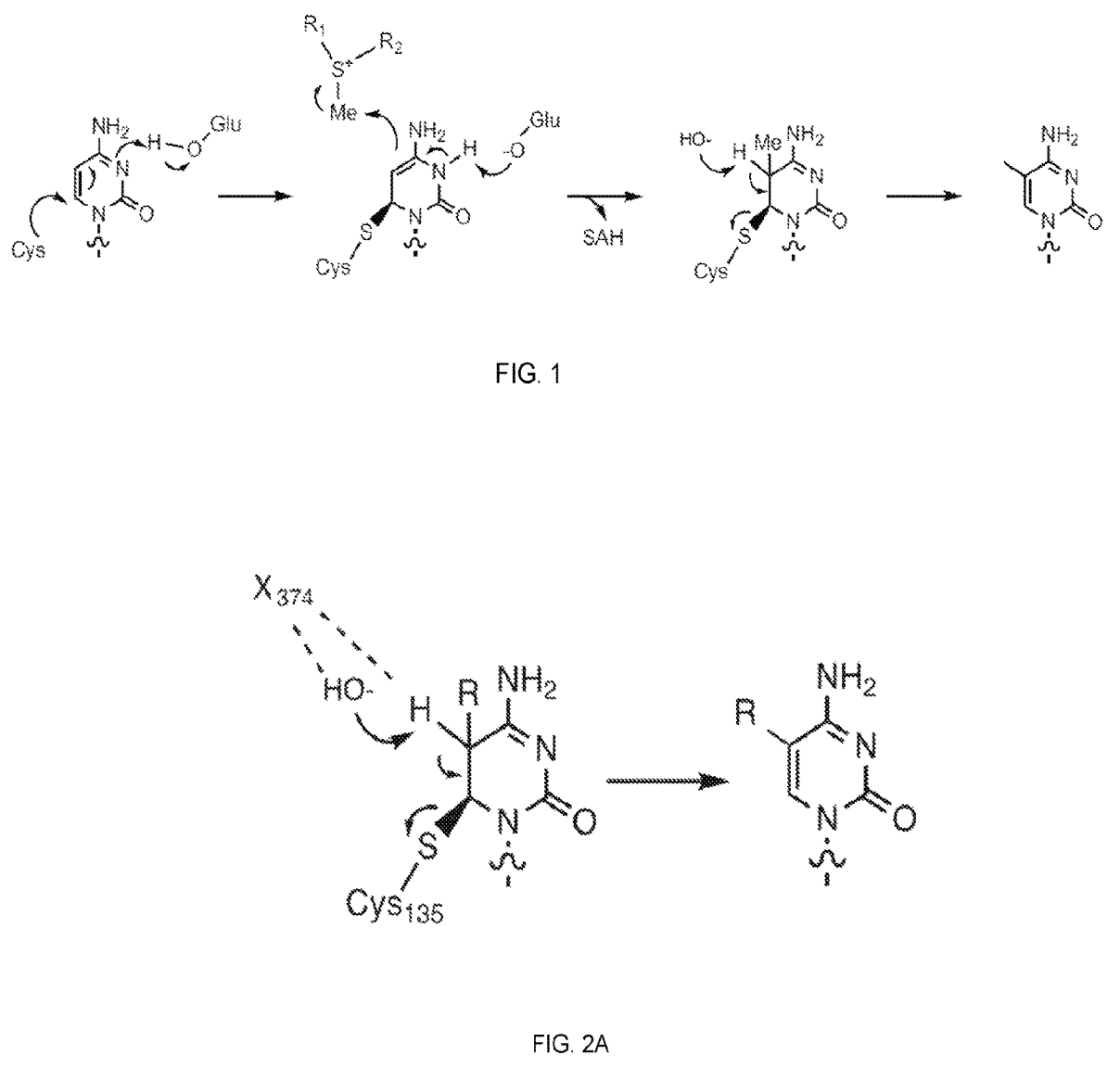
Figure 2C:
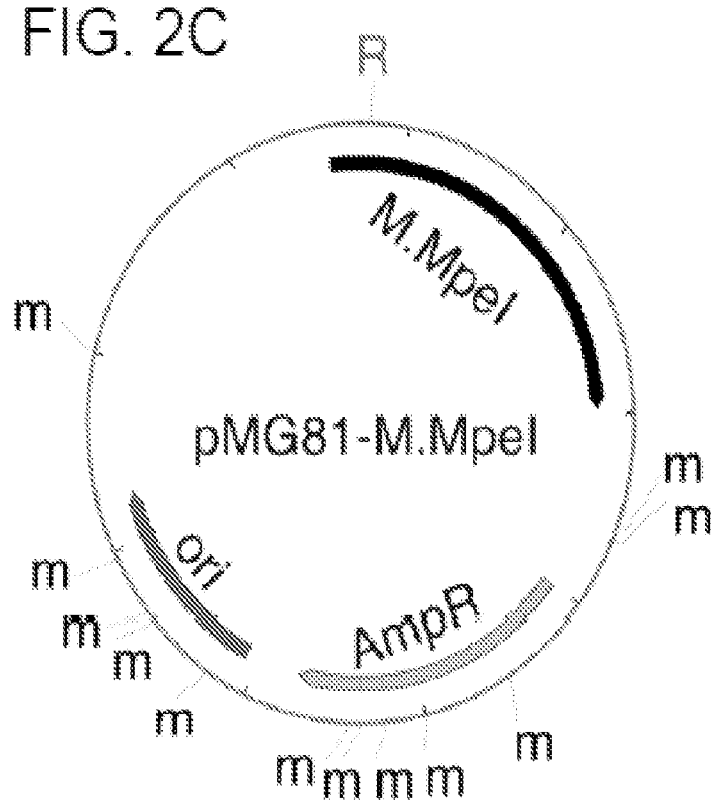

This invention reports the discovery of a neomorphic DNA modifying enzyme which takes on a new and unprecedented activity. A major subset of natural DNA cytosine methyltransferase enzymes (DNA MTases) catalyze a canonical reaction between unmodified cytosine in DNA and S-adenosyl-L-methionine (SAM), leading to the generation of 5mC in DNA and S-adenosyl-L-homocysteine (SAH) as the second product (FIG. 1). The mechanism involves formation of a covalent adduct between the enzyme and the C6 position of the cytosine ring, capture of a methyl group from SAM, and subsequent elimination and rearomatization yielding 5mC and regenerating free enzyme. These DNA cytosine MTases are found across all forms of life, with the greatest diversity of these enzymes present in bacteria. In bacteria, the MTase are typically part of a pair, with an MTase and a DNA restriction endonuclease. Most commonly, the host bacteria generates 5mC in its own genome in a specific sequence context that is also recognized by the MTase. The restriction endonuclease thus cleaves DNA in the same sequence context when it contains unmodified C, but not 5mC, thus offering a rudimentary system for protection against foreign DNA, such as that of invading bacteriophages which lack the same MTases to protect their own foreign genomes.

As noted above, in mammalian genomes, the majority of 5mC modifications occur in a CpG context. Our discovery began by examining a recently obtained crystal structure of a newly characterized bacterial CpG methyltransferase M.MpeI that is useful in the study of mammalian modifications given that it targets the same context where mammalian modifications are seen (Wojciechowski et al., PNAS, 2013). M.MpeI employs a canonical cytosine DNA methyltransferase (MTase) mechanism to make 5mC from S-Adenosyl-L-Methionine (SAM) and cytosine (FIG. 1). A focus on the active site of one CpG DNA MTase led us to discover that a conserved set of mutations in an active site Asn residue unexpectedly led to the generation of a novel and unnatural modified DNA base in vivo. Mass spectrometry, bacterial genetics, in vitro biochemical studies, and structure-guided profiling characterized the new base as 5-carboxymethylcytosine (5cxmC) which originates from car-boxy-S-adenosyl-L-methionine, providing the first example of an unnatural DNA base arising exclusively from a host's native metabolome. This result (Example 1) and associated enzyme represents the first example of a DNA cytosine carboxymethyltransferase (CxMTase), which is one embodiment of this invention.

Having made the discovery of a neomorphic CpG DNA MTase, we next determined how generally applicable this activity would be to other DNA cytosine MTases. The active site Asn residue subjected to analysis in the CpG MTase is in fact highly conserved across the DNA MTase family of interest. Using a distinctive DNA MTase that acts in a non-CpG sequence context (CCWGG), the *E. coli* Dcm MTase, analogous mutations were made in the conserved active site Asn. When expressed in *E. coli* lacking a native Dcm, these modifications resulted in the generation of 5cxmC in vivo. This result (Example 2) demonstrates the generalizability of our observations and demonstrates that any DNA C5 cytosine MTase comprising a homologous active site may into converted into a DNA CxMTases using the guidance provided herein.

Having identified and reconstituted DNA CxMTase activity in vitro, a new method was devised for discriminating between different epigenetic modifications in a bisulfite free manner. In short, for decades, bisulfite has been employed to localize 5-methylcytosine (5mC), the most important epigenetic marker in genomic DNA (gDNA). Bisulfite catalyzes the chemical conversion of unmodified cytosine (C) to uracil (U) through a process known as deamination but does not catalyze the deamination of 5mC. Thus, bisulfite treated gDNA can be sequenced to localize 5mC because the bases that were deaminated to U are read as T and those that were not deaminated are read as C. This method, however, has several limitations: 1) bisulfite is chemically destructive requiring large amounts of input DNA, 2) signals attributed to 5mC are actually a mixture of both 5mC and 5hmC, and 3) the detection of 5mC is indirect—that is one subtracts the deaminated bases and attributes them to 5mC. Subtraction increases error in detection. More recently, alternative methods have been devised for the detection of DNA cytosine modifications. A DNA deaminase-based sequencing approach uses an enzyme, rather than the chemical bisulfite, to deaminate 5mC and unmodified C, leaving protected 5hmC bases intact. This method allows for detection of 5hmC, but not 5mC or C. However, reaction of genomic DNA with a DNA CxMTase and CxSAM can convert the unmodified CpG into 5cxmC. As this modified base is protected from deamination by the novel 5cxmC base, when the resulting modified genomic DNA is treated with a DNA deaminase only 5mC bases are deaminated providing a direct readout of 5mCpGs in the genome (Example 3). Notably, third generation sequencing methods provide an alternative means to localize DNA modifications, whereby modified DNA leaves a distinct signature when analyzed by nanopore or SMRT sequencing approaches. The conversion of unmodified CpGs into 5cxmC offers an additional signal for such approaches. The inventive method thus comprises use of an engineered DNA methyltransferase enzyme with a naturally-occurring derivative of S-adenosyl-L-methionine to transform unmodified Cs with a carboxymethyl functional group, creating an enzymatically modified cytosine base in DNA molecules of interest. When treated with the appropriate deaminating enzyme, e.g., APOBEC3A, only 5mC is deaminated, allowing for localization of any 5mC by sequencing, or alternatively the modifications can be analyzed by third generation sequencing approaches even without a need for deamination.

Definitions

The terms "polynucleotide", "nucleotide", "nucleotide sequence", "nucleic acid", and "oligonucleotide" are used interchangeably in this disclosure. They refer to a polymeric form of nucleotides of any length, either deoxyribonucleotides or ribonucleotides, or analogs thereof. Suitable polynucleotides include DNA, preferably genomic DNA. The polynucleotides comprising the sample nucleotide sequence may be obtained or isolated from a sample of cells, for example, mammalian cells, preferably human cells. Suitable samples include isolated cells and tissue samples, such as biopsies.

Modified cytosine residues including 5hmC and 5mC have been detected in a range of cell types including embryonic stem cells (ESCs) and neural cells. Suitable cells also include somatic and germ-line cells which may be at any stage of development, including fully or partially differentiated cells or non-differentiated or pluripotent cells, including stem cells, such as adult or somatic stem cells, cancer stem cells, fetal stem cells or embryonic stem cells.

For example, polynucleotides comprising the sample nucleotide sequence may be obtained or isolated from neural cells, including neurons and glial cells, contractile muscle cells, smooth muscle cells, liver cells, hormone synthesizing cells, sebaceous cells, pancreatic islet cells, adrenal cortex cells, fibroblasts, keratinocytes, endothelial and urothelial cells, osteocytes, and chondrocytes.

Cells of interest include disease-associated cells, for example cancer cells, such as carcinoma, sarcoma, lymphoma, blastoma or germ line tumor cells. Other cell types include those with a genotype of a genetic disorder such as Huntington's disease, cystic fibrosis, sickle cell disease, phenylketonuria, Down syndrome or Marfan syndrome.

Methods of extracting and isolating genomic DNA and RNA from samples of cells are well-known in the art. For example, genomic DNA or RNA may be isolated using any convenient isolation technique, such as phenol/chloroform extraction and alcohol precipitation, caesium chloride density gradient centrifugation, solid-phase anion-exchange chromatography and silica gel-based techniques.

In some embodiments, whole genomic DNA and/or RNA isolated from cells may be used directly as a population of polynucleotides as described herein after isolation. In other embodiments, the isolated genomic DNA and/or RNA may be subjected to further preparation steps. The genomic DNA and/or RNA may be fragmented, for example by sonication, shearing or endonuclease digestion, to produce genomic DNA fragments. A fraction of the genomic DNA and/or RNA may be used as described herein. Suitable fractions of genomic DNA and/or RNA may be based on size or other criteria. In some embodiments, a fraction of genomic DNA and/or RNA fragments which is enriched for CpG islands (CGIs) may be used as described herein.

The term, "epigenetics," refers to the complex interactions between the genome and the environment that are involved in development and differentiation in higher organisms. The term is used to refer to heritable alterations that are not due to changes in DNA sequence. Rather, epigenetic modifications, or "tags," such as DNA methylation and histone modification, alter DNA accessibility and chromatin structure, thereby regulating patterns of gene expression. These processes are crucial to normal development and differentiation of distinct cell lineages in the adult organism. They can be modified by exogenous influences, and, as such, can contribute to or be the result of environmental alterations of phenotype or pathophenotype. Importantly, epigenetic programming has a crucial role in the regulation of pluripotency genes, which become inactivated during differentiation.

The terms "construct", "cassette", "expression cassette", "plasmid", "vector", or "expression vector" is understood to mean a recombinant nucleic acid, generally recombinant DNA, which has been generated for the purpose of the expression or propagation of a nucleotide sequence(s) of interest, or is to be used in the construction of other recombinant nucleotide sequences.

"Deamination" is the removal of an amino group from a molecule. Enzymes that catalyze this reaction are called deaminases. Deaminases include, without limitation, APOBEC1, APOBEC3A, APOBEC3B, APOBEC3C, APOBEC3DE, APOBEC3F, APOBEC3G, Activation-induced cytidine deaminase (AID), and CDA from lamprey. More broadly this deaminase family includes homologs from various species all of which are thought to catalyze similar reactions on nucleic acids as described in Krishnan et al. (Proc Natl Acad Sci USA. 2018; 115(14):E3201-E3210 and Iyer et al. (Nucleic Acids Res. 2011 December; 39(22): 9473-97).

"Methyltransferases" are a large group of enzymes that all methylate their substrates but can be split into several subclasses based on their structural features. The most common class of methyltransferases is class I, all of which contain a Rossmann fold for binding S-Adenosyl-L-methionine. A preferred methyltransferase for use in the invention is bacterial CpG methyltransferase M.MpeI of SEQ ID NO: 1 comprising an amino acid substitution, N374R and an optional his tag. Sequences having at least 90, 92, 94, 96, 97, 99 and 99% sequence identity with SEQ ID NO: 1 are also within the scope of the invention. Also included are homologous cytosine methyltransferases which can be genetically engineered to utilize CxSAM as a substrate. Such enzymes include for example Dcm or the GpC MTase such as M.CviPI. FIG. 11B lists a number of methyltransferases, but not all, which can be genetically modified at the enzyme active site to confer carboxymethyltransferase activity as described above.

In general "detecting", "determining", and "comparing" refer to standard techniques in epigenetic modification identification described in the examples and equivalent methods well known in the art. These terms apply particularly to sequencing, where DNA sequences are compared. There are a number of sequencing platforms that are commercially available and any of these may be used to determine or compare the sequences of polynucleotides.

The term "sodium bisulfite sequencing reagents" refers to prior art methods for detecting 5mC as is described in Frommer, et al., Proceedings of the National Academy of Sciences, 89.5:1827-1831 (1992).

The terms "sequence identity" or "identity" refers to a specified percentage of residues in two nucleic acid or amino acid sequences that are identical when aligned for maximum correspondence over a specified comparison window, as measured by sequence comparison algorithms or by visual inspection. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity.

The term "comparison window" refers to a segment of at least about 20 contiguous positions in which a sequence may be compared to a reference sequence of the same number of contiguous positions after the two sequences are aligned optimally. In a refinement, the comparison window is from 15 to 30 contiguous positions in which a sequence may be compared to a reference sequence of the same number of contiguous positions after the two sequences are aligned optimally. In another refinement, the comparison window is usually from about 50 to about 200 contiguous positions in which a sequence may be compared to a reference sequence of the same number of contiguous positions after the two sequences are aligned optimally.

The terms "complementarity" or "complement" refer to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 4, 5, and 6 out of 6 being 66.67%, 83.33%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 40%, 50%, 60%, 62.5%, 70%, 75%, 80%, 85%, 90%, 95%, 97%, 98%, 99%, or 100%, or percentages in between over a region of 4, 5, 6, 7, and 8 nucleotides, or refers to two nucleic acids that hybridize under stringent conditions.

A "selected phenotype" refers to any phenotype, e.g., any observable characteristic or functional effect that can be measured in an assay such as changes in cell growth, proliferation, morphology, enzyme function, signal transduction, expression patterns, downstream expression patterns, reporter gene activation, hormone release, growth factor release, neurotransmitter release, ligand binding, apoptosis, and product formation. Such assays include, e.g., transformation assays, e.g., changes in proliferation, anchorage dependence, growth factor dependence, foci formation, growth in soft agar, tumor proliferation in nude mice, and tumor vascularization in nude mice; apoptosis assays, e.g., DNA laddering and cell death, expression of genes involved in apoptosis; signal transduction assays, e.g., changes in intracellular calcium, cAMP, cGMP, IP3, changes in hormone and neurotransmitter release; receptor assays, e.g., estrogen receptor and cell growth; growth factor assays, e.g., EPO, hypoxia and erythrocyte colony forming units assays; enzyme product assays, e.g., FAD-2 induced oil desaturation; transcription assays, e.g., reporter gene assays; and protein production assays, e.g., VEGF ELISAs. A candidate gene is "associated with" a selected phenotype if modulation of gene expression of the candidate gene causes a change in the selected phenotype Kits for Practicing the Methods of the Invention In a further aspect, a kit comprising the variant M.MpeI methyltransferase of the invention and a synthetic CxSAM substrate is provided. The kit can also comprise other reagents necessary to identify the epigenetic modifications described herein. In particular, these kits can be used in a method for identifying methylated cytosine molecules in target nucleic acids in a bisulfite free manner. The kit comprises the CxSAM substrate as described above in a suitable container, in combination with a methyltransferase in a suitable container.

In yet another aspect, the kit contains the carboxymethyltransferase, synthetic CxSAM, at least one cytosine deaminase (e.g. APOBEC3A). Optionally, T4 Phage β-glucosyltransferase (T4-βGT), UDP-glucose, and a set of APOBEC resistant custom adaptors, such as those containing 5pyC, can be provided. Buffers to each of the three enzymes, carboxymethyltransferase, T4-βGT, and cytosine deaminase can be provided. Up to 4 gDNA spike-in controls will be additionally provided (T4-hmC phage DNA, a CpG methylated λ-phage DNA, dcm−/dam− pUC19 DNA, and an oligonucleotide spike-in control). A custom M.AluI generated improved λ-phage control may replace the CpG methylated λ-phage control and pUC19 DNA. This full kit is described in Example II.

The following materials and methods are provided to facilitate the practice of the present invention.

*E. coli* Strains:

ER1821 *E. coli* (New England Biolabs (NEB), F-glnV44 e14-(McrA) rfbDI? relAI? endAI spoTI? thi-I Δ(mcrC-mrr) 114::IS10) were used in all M.MpeI experiments, including cloning. This strain is deleted of all methylation-specific restriction factors which recognize CpG methylation as foreign. ER1821 ΔcmoA was created with PIvir phage transduction using the ΔcmoA strain (JW1859) from the KEIO collection and kanamycin selection. (16, 26) This new ER1821 ΔcmoA strain was validated by colony PCR. For all Dcm experiments, dcm−/dam− *E. coli* were used (NEB C2925I, ara-14 leuB6 fhuA31 lacY1 tsx78 glnV44 galK2 galT22 mcrA dcm-6 hisG4 rfbDI R(zgb210::Tn10) TetS endAl rspLI36 (StrR) dam13:: Tn9 (CamR) xylA-5 mtl-1 thi-I mcrBl hsdR2).

Cloning:

The WT M.MpeI sequence was obtained from the protein FASTA file from the PDB deposited (4DKJ) crystal structure. (9) This protein sequence notably contained Q68R and K71R as "unintended mutations", S295P for resistance to proteolysis, and a C terminal LEHHHHHH tag for purification. This protein FASTA file was then codon optimized using IDT's online tool, modified with 10 silent mutations and ordered as a GeneBlock from IDT. The gene was PCR amplified with primers containing BsaI-HF and HindIII-HF overhangs with Phusion Polymerase (NEB) and ligated using traditional cloning into a double-digested, gel purified, pMG81 plasmid, a medium copy number vector with an anhydroteteracycline promoter. (27)

The WT dcm gene was obtained by directly amplifying ER1821 gDNA with Phusion Polymerase (NEB) and primers introducing a C-terminal His tag and appropriate BsaI overhangs. This gene was then assembled using Golden-Gate cloning into a compatible pMG81 plasmid. (28)

All point mutations were obtained by performing Q5 Site Directed Mutagenesis (NEB BaseChanger). Each new construct was double-digested to confirm plasmid integrity and the gene was Sanger sequenced (GeneWiz). The final protein sequences for both M.MpeI N374K and Dcm 436K are shown below in Table 1.

| Name | Sequence (5'-3') | Description |
|---|---|---|
| M.MpeI N374K | MNSNKDKIKVIKVFEAFAGIGSQFKALK NIARSKNWEIQHSGMVEWFVDAIVSYV AIHSKNFNPKIERLDRDILSISNDSKMPIS EYGIKKINNTIKASYLNYAKKHFNNLFD IKKVNKDNFPKNIDIFTYSFPCQDLSVQ GLQKGIDKELNTRSGLLWEIERILEEIKN SFSKEEMPKYLLMENVKNLLSHKNKKN YNTWLKQLEKFGYKSKTYLLNSKNFDN CQNRERVFCLSIRDDYLEKTGFKFKELE KVKNPPKKIKDILVDSSNYKYLNLNKY ETTTFRETKSNIISRPLKNYTTFNSENYV YNINGIGPTLTASGANSRIKIETQQGVRY LTPLECFKYMQFDVNDFKKVQSTNLISE NKMIYIAGKSIPVKILEAIFNTLEFVNNE ELEHHHHHH* (SEQ ID NO: 1, lacks His tag; SEQ ID NO: 2 includes His tag) | CpG M.MpeI Carboxymethyltransferase with a C-terminal His Tag protein sequence. The mutated K residue is <u>underlined and bolded</u>. This residue can be optionally changed to an R as well. Example III additionally describes possible "second generation" mutations. |
| Dcm N436K | MQENISVTDSYSTGNAAQAMLEKLLQI YDVKTLVAQLNGVGENHWSAAILKRA LANDSAWHRLSEKEFAHLQTLLPKPPA HHPHYAFRFIDLFAGIGGIRRGFESIGGQ CVFTSEWNKHAVRTYKANHYCDPATH HFNEDIRDITLSHKEGVSDEAAAEHIRQ HIPEHDVLLAGFPCQPFSLAGVSKKNSL GRAHGFACDTQGTLFFDVVRIIDARRPA MFVLENVKNLKSHDQGKTFRIIMQTLD ELGYDVADAEDNGPDDPKIIDGKHFLP QHRERIVLVGFRRDLNLKADFTLRDISE CFPAQRVTLAQLLDPMVEAKYILTPVL WKYLYRYAKKHQARGNGFGYGMVYP NNPQSVTRTLSARYYKDGAEILIDRGW DMATGEKDFDDPLNQQHRPRRLTPREC ARLMGFEAPGEAKFRIPVSDTQAYRQF GKSVVVPVFAAVAKLLEPKIKQAVALR QQEAQHGRRSRHHHHHH* (SEQ ID NO: 3 lacks His tag; SEQ ID NO: 4 includes His tag) | CCWGG Dcm Carboxymethyltransferase with a C-terminal His Tag protein sequence. The mutated K residue is <u>underlined and bolded</u>. This residue can be optionally changed to an R as well. |

-continued

Figure 15A:
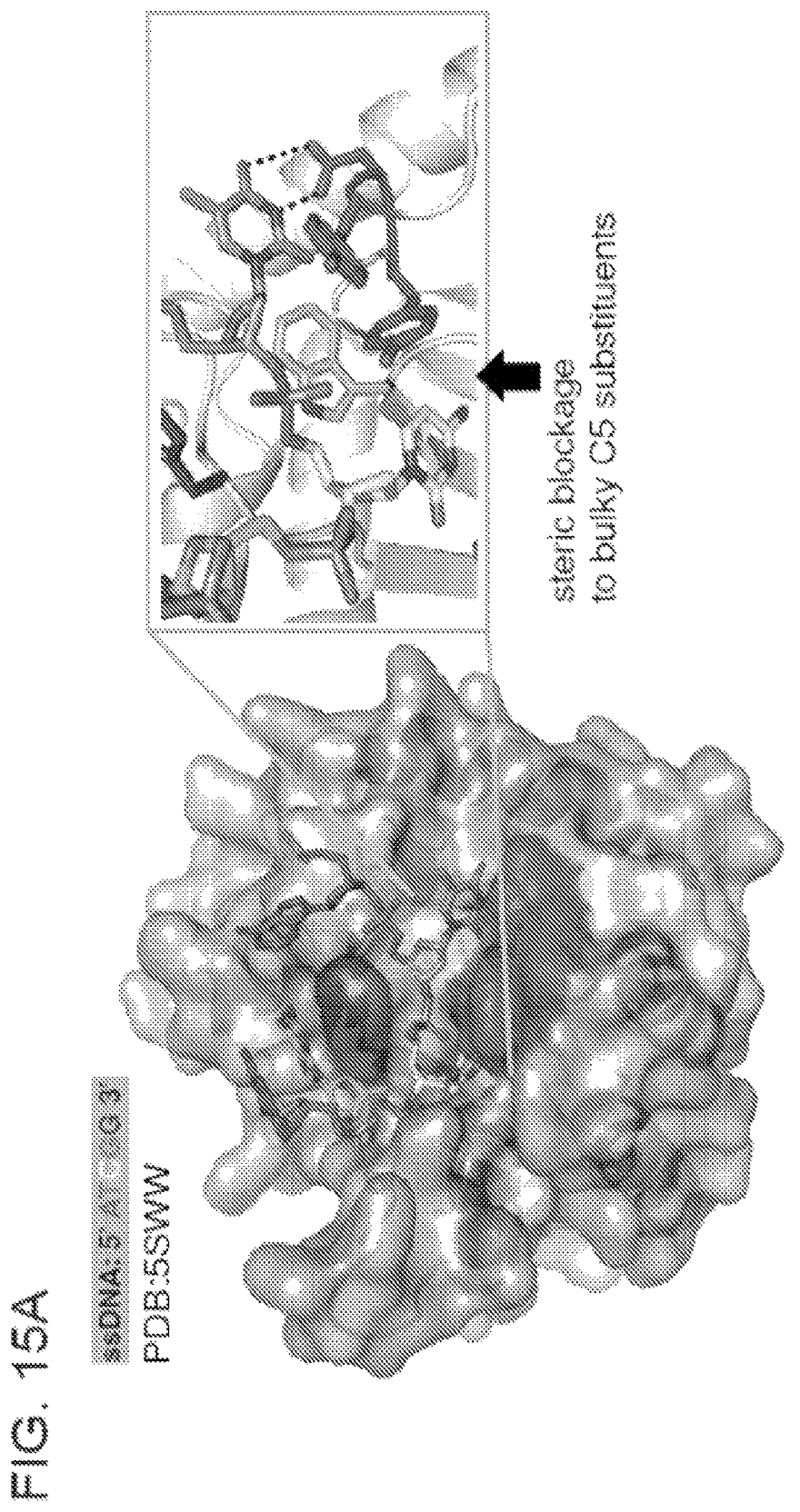
Figures 15B, 15C:
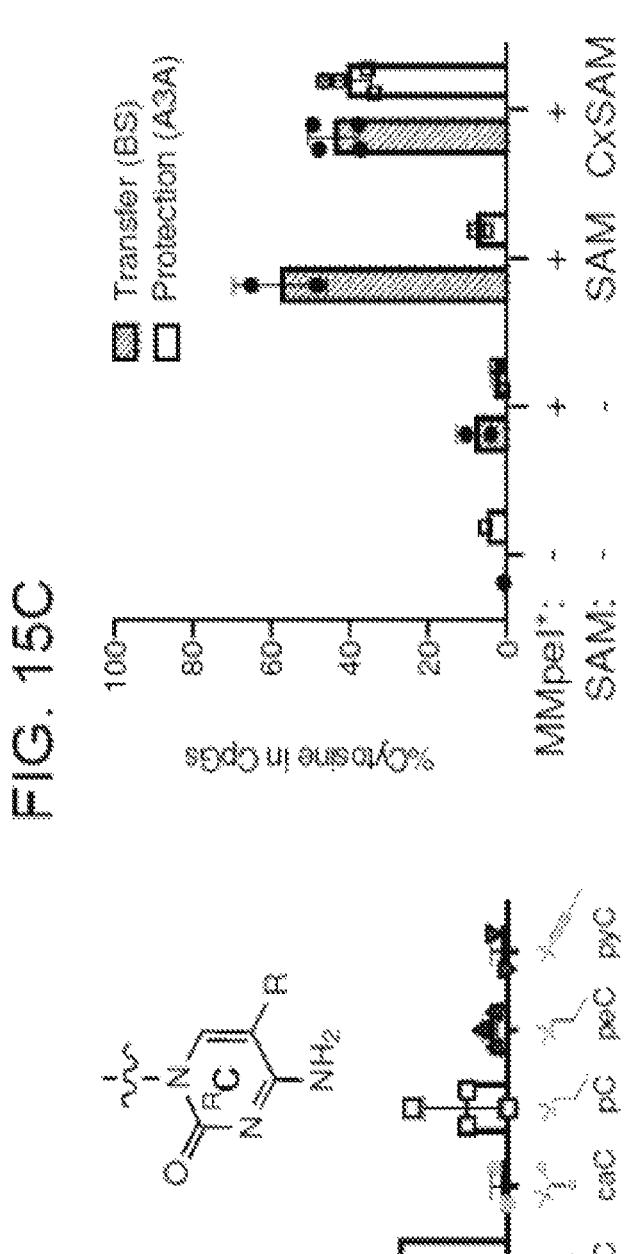

| Name | Sequence (5'-3') | Description |
|------|------------------|-------------|
| Oligonucleotide spike-in | TAGTGTTGATATGGGTTATGAATGAAG TAAGGACGTTGAATAGT/5mC/GAGCCG TAGGCGCTGTCGTAGGA/5mC/GAGTGTT AAGGTATATGAGTAGATGATTGAT (SEQ ID NO: 5) | ssDNA spike in control for troubleshooting |
| 202mer F | TTGATATGGGTTATGAATGAAGTA (SEQ ID NO: 6) | Used in FIG. 15B |
| 202mer R | TCATCTACTCATATACCTTAACACT (SEQ ID NO: 7) | Used in FIG. 15B |
| 202mer | TTGATATGGGTTATGAATGAAGTAGTC GATCTTTCATCATATTCTAGATCCCTCT GAAAAAATCTTCCGAGTTTGCTAGGCA GTGATACATAACTCTTTTCCAATAATTG GGGAAGTCATTCAAATCTATAATAGGT TTCAGATTTAATTCTGACTGTAGCTGCT GAAACGTTGCGGAGTGTTAAGGTATAT GAGTAGATGA (SEQ ID NO: 8) | Used in FIG. 15B |
| Lambda Amplicon F | (8mer-inline-barcode)gaaaaatgggtggatgg (SEQ ID NO: 9) | Used in FIG. 15C |
| Lambda Amplicon R | (8mer-inline-barcode)caccatcctcttcct (SEQ ID NO: 10) | Used in FIG. 15C |

In Vivo Methyltransferase Assays:

pMG81-MMpeI or pMG81-Dcm plasmid DNA was used to individually transform chemically competent ER1821 or dcm−/dam− cells onto separate plates. Single colonies were started in overnight cultures (3 mL LB, 100 µg/mL carbenicillin). A similar protocol was used for overexpression experiments which utilized double transformation of both pMG81-MMpeI and pCA24N-CmoA from the ASKA collection (3 mL LB, 100 µg/mL carbenicillin+25 µg/mL chloramphenicol). (17) Overnight colonies were allowed to grow at 37° C. until log phase (OD 0.4-0.7) before induction with 20 ng/mL anhydrotetracycline (ATc). In some overexpression cultures, CmoA was additionally induced with 1 mM Isopropyl β-D-1-thiogalactopyranoside (IPTG).

Cultures were left at 37° C. overnight. Plasmid extractions (Qiagen) or gDNA extractions (Qiagen DNeasy) were then performed, eluted in 10 mM Tris-Cl pH 8.0, and quantified by nanodrop.

Nucleoside LC-MS/MS:

LC-MS/MS was performed as previously described with slight modifications. (29) Briefly, >15 ng plasmid or gDNA was digested with Nucleoside Digestion Mix (NEB) in a 10 total volume for 4 hours at 37° C., and the mixture was diluted 10-fold into 0.1% formic acid with the addition of 770 fmol T-D$_3$ internal standard (ITSD) into a volume of 20 µL. Only 5 µL was injected onto the instrument. An Agilent 1200 Series HPLC equipped with a 5 µm, 2.1×250 mm Supelcosil LC-18-S analytical column (Sigma) was equilibrated to 45° C. in Buffer A (0.1% formic acid). The nucleosides were separated using a gradient of 0-10% Buffer B (0.1% formic acid, 30% (v/v) acetonitrile) over 8 min at a flow rate of 0.5 mL/min. Tandem MS/MS was performed by positive ion mode ESI on an Agilent 6460 triple-quadrupole mass spectrometer, with gas temperature of 225° C., gas flow of 12 L/min, nebulizer at 35 psi, sheath gas temperature of 300° C., sheath gas flow of 11 L/min, capillary voltage of 3,500 V, fragmentor voltage of 70 V, and delta EMV of +1,000 V. Collision energies were 10 V for all bases except for 5cxmC (25V). MRM mass transitions were (C: 228.1→112.1, T: 243.1→127.1, T-D3: 246.1→130.1, 5mC: 242.1→126.1, 5mC-D3: 245.1→129.1, 5cxmC 286.1→170.1).

The amount of total input DNA injected was first obtained using T and the T-D3 ITSD using the equations below, where A signifies area measured by the MS instrument. This number was then used to calculate a relative area in the experiments that lack a chemical standard for 5cxmC. This approach allows for accurate comparisons across conditions and is used in FIGS. 4 and 5.

$$fmol\ T = 192.5\ fmol\ T\ \frac{A_T}{A_{T-D_3}}$$

$$Relative\ 5cxmC\ (arbitrary\ units) = \frac{A_{5cxmC}}{fmol\ T}$$

A standard for 5cxmC was synthesized using an enzymatic approach. Excess M.MpeI N374K was reacted with 160 µM CxSAM and 250 nM hemimethylated substrate (see oligonucleotide assay methods) for 37° C. for 2 hrs. 1:30 of the reaction volume was then the subjected to MspI digestion. Gels were loaded with 95% Formamide and visualized by 20% TBE Acrylamide Denaturing PAGE and Typhoon imager for the FAM fluorophore (excitation at 488 nm, emission at 520 nm). Bands were quantified using ImageJ and normalized relative to the no CxSAM substrate control confirming >98% carboxymethylation. The remaining fully carboxymethylated standard was purified using an oligonucleotide spin column (Zymo). This purified standard was requantified using an oligonucleotide standard curve with the unmodified FAM oligo. Concentrated hemi-carboxymethylated oligonucleotide was then digested with Nucleoside Digestion Mix (New England Biolabs) in a 10 µL total volume for 4 hours at 37° C., and the mixture was diluted 10-fold into 0.1% formic acid. Serial dilutions were obtained down to the specified limit of detection. Denaturing PAGE confirmed the purity of the chemoenzymatically generated standard and LC-MS/MS standard curve confirmed linearity.

The slope obtained from the LC-MS/MS standard curve was used to convert the integrated area of an experimental sample to fmol 5cxmC detected.

With knowledge of the amount of T and 5cxmC injected, it was possible to calculate the total amount of 5cxmC relative to either total CpG sites (M.MpeI) or CCWGG sites (Dcm, W=A/T). For M.MpeI experiments, the amount of T injected was converted to total amount of CpGs injected by dividing by the molar ratio of Ts to CpGs in the pMG81-MMpeI plasmid=5.07. For overexpression experiments, the average molar ratio of Ts to CpGs for both the pCA24N-CmoA and pMG81-MMpeI was used=4.44.

For Dcm samples, gDNA extractions were used and not plasmid extractions. First, we obtained the complete genome assembly of K-12 MG1655, the parent strain of the dam–/dcm– E. coli strain (GenBank: U00096.3). The molar ratio (100.6) comparing total instances of T (2,284,124) to CCWGG (22,716) was used to calculate the total amount of 5cxmC relative to total CCWGG sites.

Protein Purification:

All variants were purified using a C-terminal His tag. pMG81-MMpeI or pMG81-M.MpeI-N374K plasmid DNA was used to individually transform chemically competent ER1821 cells onto separate plates. Single colonies were started in overnight cultures (10 mL LB, 100 µg/mL carbenicillin). Large scale cultures (1 L LB, 100 µg/mL ampicillin) were started in the morning and allowed to grow at 37° C. until log phase (OD~0.4-0.7) before switching the temperature to 16° C. After 20 minutes, 20 ng/mL anhydrotetracycline (ATc) was used to induce protein overexpression and cultures were left at 16° C. overnight. Cells were harvested by ultracentrifugation (8000 g, 30 min, 4° C.) before resuspending in 25 mL Buffer A (50 mM Tris Cl, pH 7.5 at 25° C., 150 mM NaCl, 25 mM Imidazole, 10% Glycerol (v/v))+1 EDTA-free Protease Inhibitor Tablet (Sigma)+10 µL RNase A (Thermo Fisher). Resuspended cells were frozen overnight at –80° C.

Cells were lysed using a sonicator and harvested (30 min at 27,000 g, 4° C.). During this time, 4 mL His Cobalt Resin (Thermo Fisher) was equilibrated with Buffer A. Soluble lysate was loaded and passed through a gravity column containing His Cobalt Resin. After loading, 25 column volumes (CV) of Buffer B (50 mM Tris Cl, pH 7.5 at 25° C., 1 M NaCl, 25 mM Imidazole, 10% Glycerol (v/v)) was passed through the column. This high salt wash was not necessary for WT M.MpeI protein. The column was then re-equilibrated with 5 CV Buffer A. Protein was eluted with sequential fractions of Buffer C (50 mM Tris Cl, pH 7.5 at 25° C., 150 mM NaCl, 150 mM Imidazole, 10% Glycerol (v/v)). Samples were dialyzed (8,000 MWCO, Thermo Fisher) overnight at 4° C. in 2 L of prechilled Dialysis Buffer (20 mM Tris HCl pH 7.5 at 25° C., 0.2 mM EDTA, 2 mM DTT, 150 mM NaCl, 10% Glycerol (v/v)). The next morning, protein was concentrated (10,000 MWCO, Millipore). Cold 40% (v/v) glycerol was added to the concentrated protein to dilute the dialyzed protein 2-fold before flash freezing with liquid nitrogen and long-term storage at –80° C. All preps were quantified by comparison to a BSA standard curve after running SDS-PAGE and visualizing with Coomassie Blue.

Figure 6A:
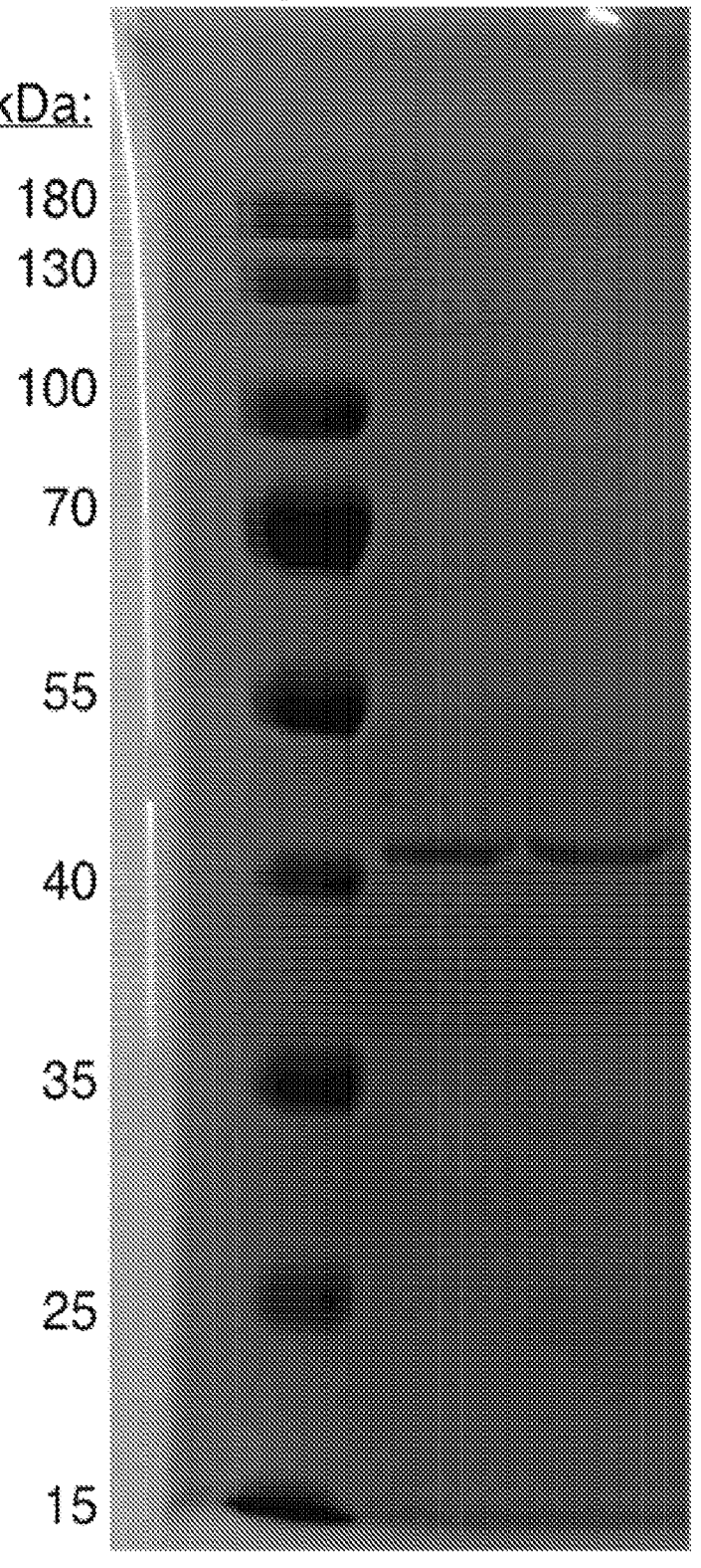
FIGS. 6A-6B. Purity of in vitro reagents: WT M.MpeI, M.MpeI N374K, and CxSAM.
Figure 6B:
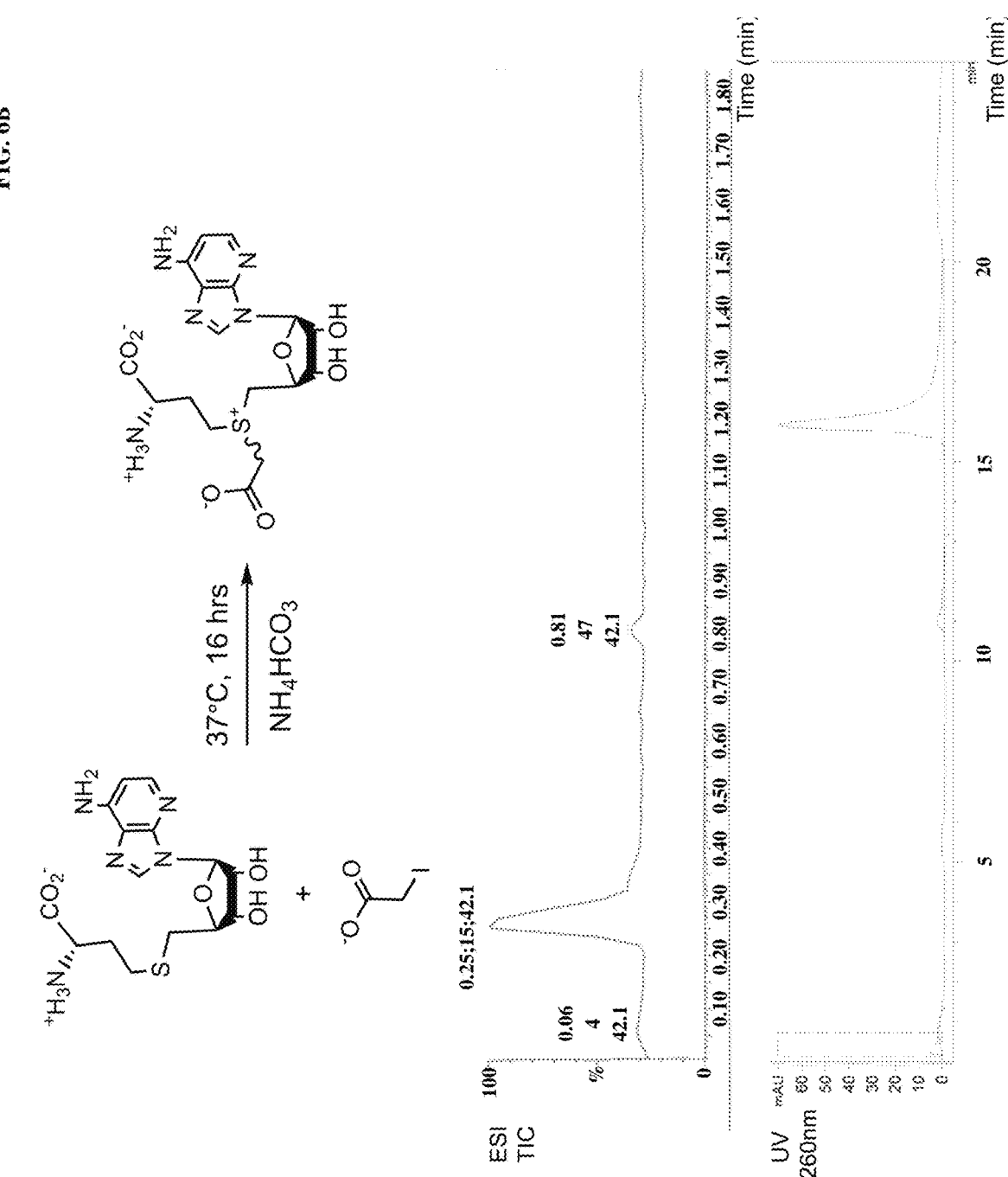

CxSAM Synthesis:

Reactions were performed as described previously. (15) Briefly, 50 mg of SAH (Sigma) was reacted with 1.67 g of Iodoacetic Acid (Sigma) and 8.3 mL of 150 mM Ammonium Bicarbonate at 37° C. for 24 hrs. Reactions were quenched with 80 mL methanol and placed at 4° C. overnight. Samples were spun down at 2,000 g at 4° C. for 30 minutes. The pellet was washed 2× with ice cold methanol and air dried. Samples were dissolved in 400 µL Nuclease Free Water (Ambion). HPLC separations were attempted as previously described, 18 but the UV absorbance trace showed that no further purifications were necessary (FIG. 6). CxSAM was quantified using the adenine chromophore at 260 nm (15,400 L mol-1 cm-1, 4.3% yield). High resolution mass spectrometry (HRMS) was obtained to 443.1360 (mDa=–0.2, PPM=–0.5, Theoretical Mass: 443.1343).

Restriction Digest Based Assays:

All restriction digestions were performed at 37° C. for 1 hr in 1×NEB CutSmart Buffer in the specified volume (50 mM Potassium Acetate, 20 mM Tris-acetate, 10 mM Magnesium Acetate, 100 µg/ml BSA, pH 7.9 at 25° C.).

Puc19 Assay:

3-fold serial dilutions of M.MpeI (0.78 µM–3.2 nM) were incubated with 160 µM SAM or CxSAM substrate and pUC19 plasmid DNA (100 ng) for 4 hrs at 37° C. in M.MpeI reaction buffer (10 mM Tris Cl, 50 mM NaCl, 1 mM DTT, 1 mM EDTA, pH 7.9 at 25° C.) in a 5 µL volume. 2.5 µL of DNA was then incubated with the appropriate restriction enzyme to assess modification status of cytosines in two CpG contexts, and the plasmid DNA was simultaneously linearized with HindIII-HF (NEB) in a final digestion volume of 25 µL. HpaII (NEB) recognizes C<u>C</u>GGs (13 sites) and HhaI (NEB) recognizes G<u>C</u>GCs (17 sites). Samples were briefly treated with 1 µL Proteinase K at 37° C. for 10 min. Substrates were separated on 1% TAE Agarose gel and visualized with SYBR Safe DNA Gel Stain (Thermo-Fisher).

Oligonucleotide Assay:

Assays were performed with minor modifications relative to a previously described protocol. (19) A fluorescein (FAM) labelled oligonucleotide with single unmethylated C<u>C</u>GG and unlabeled complementary bottom strand with methylated C<u>C</u>GG were obtained from IDT (Table 1). 1.4× excess of bottom strand was duplexed to top strand by heating to 95° C. for 5 minutes and slow cooling down to 25° C. 200 nM of the duplexed, hemimethylated oligo was reacted with serial dilutions of M.MpeI and 40 µM SAM or CxSAM substrate at 37° C. in M.MpeI reaction buffer and a final volume of 5 µL for 30 minutes before heat inactivation at 95° C. for 5 min. 25× unmethylated bottom strand was then added before the duplexing thermocycler protocol was repeated. A 50 µL HpaII digestion was then used to report on the modification status (methylation or carboxymethylation) of the top strand. Samples were mixed with 2× formamide loading buffer, heat-denatured at 95° C. for 5 minute, and 50 µL was loaded for 20% TBE-Acrylamide denaturing PAGE. The gels were imaged for FAM fluorescence using a Typhoon imager (excitation at 488 nm, emission at 520 nm). Bands were quantified using ImageJ and fit to a sigmoidal dose response curve using Prism 8. In vitro carboxymethylation was also confirmed by purifying the reaction mixture before the strand exchange step with an Oligo Clean & Concentrator column (Zymo) and analyzed by oligonucleotide ESI-MS (Novatia, FIG. 8).

Protein Structures:

The structure of M.MpeI bound to SAH and a 5-fluorocytosine containing double-stranded DNA substrate was obtained (PDB 4DKJ). The mutant N374K residue was manually created in PyMOL. Subsequently, CxSAM (PDB 4QNV) was manually overlaid on top of SAH with no energy minimization calculations to determine bond angles.

TA Cloning Assay of 5-Modified Substrates:

Single stranded DNA with homogenously modified cytosines was obtained by LATE-PCR as previously described (Schutsky et al. Nucleic Acids Res 2017). Modified triphosphates were obtained from TriLink unless otherwise noted here (mC: NEB, peC/pC: synthesized in house, purified by ion-pair chromatography, Ghanty et al. JACS 2018). 1 ng of purified single stranded DNA was incubated with 8 µM A3A at 37° C. for two hours. This 202 base pair amplicon was PCR amplified and TA cloned. Single clones were sent for Sanger Sequencing. After alignment to the parent 202mer substrate (Table 1), C to T conversions were quantified as a percentage of total Cs.

NGS Assays for DM-Seq Validity

Pre-CpG methylated λ-phage DNA and pUC19 DNA were separately sheared on a Covaris sonicator. 1 ng of each sheared DNA was placed in a reaction tube and reacted with 360 nM (final concentration) M.MpeI WT or N374K and 160 µM SAM or CxSAM at 37° C. for four hours before heat denaturation at 95° C. DNA was concentrated using an Oligo Clean and Concentrator Column (Zymo). DNA was subjected to bisulfite conversion (Diagenode) according to manufacturer protocols and library prep using an Adaptase strategy (Swift Accel NGS Methyl Seq). Libraries were sequenced on an Illumina MiSeq in house.

Alternatively, sheared and unmodified λ-phage DNA was ligated with forkhead adaptors resistant to either bisulfite or enzymatic deamination. After annealing a primer to the overhang region of the forkhead, the DNA strand was copied using Klenow (exo-) DNA Polymerase (NEB) with 5mCTP in lieu of dCTP. The strands were then treated with N374K M.MpeI and no SAM, SAM, or CxSAM as described above, followed by either bisulfite mediated deamination (as above) or deamination with A3A (using ACE-Seq conditions as described below). A PCR was performed (KAPA) to complete the library and subjected to next-generation sequencing on an Illumina MiSeq in house.

Amplicon sequencing assays were performed under similar conditions except before deamination reactions, samples were split into two to be reacted with 1) bisulfite (Diagenode) and 2) concentrated MBP-A3A-His under ACE-Seq conditions (described below). After deamination reactions and concentration, samples were directly amplified at a single locus within the X-phage with in-line barcoded primers devoid of Cs on the top strand (Table 1). Amplicons were deep sequenced at GeneWiz.

Bioinformatics:

Reads were quality and length trimmed with Trim Galore! Reads were aligned with Bismark and deduplicated with Picard. A custom, in house script was used to identify reads which contain completely modified CpGs. For amplicon experiments, inline barcodes were demultiplexed using CutAdapt.

Ideal DM-Seq Workflow:

gDNA isolated from cells is obtained and nanodrop is used to confirm purity with UV 260/230 and 260/280>1.8. DNA is quantified by Qubit fluorimetry. Up to 4 unsheared spike-in controls will be added to the DNA to quantify errors. In a first embodiment, T4-hmC phage DNA, a CpG methylated λ-phage DNA, linearized dcm⁻/dam⁻ pUC19 DNA, and an oligonucleotide spike-in control containing both Cs and mCs (Table 1) are all added to the gDNA at a concentration <0.25% w/w individually. In an optional embodiment of the methodology, λ-phage DNA premethylated by the methyltransferase M.AluI (AGCT sequence context) can be used in place of the CpG methylated λ-phage DNA and pUC19 DNA. A Covaris sonicator is used to randomly shear gDNA to mean size of ~350 bp for Illumina sequencing or longer for long-read sequencing or custom amplicons (e.g. PacBio or Nanopore).

In an optional embodiment of this method, the sheared DNA can be end-repaired, A-tailed, and forkhead full-length Illumina adapters can be installed with indices unique to each individual sample type (e.g. Illumina TruSeq DNA Library Prep LT or HT). While all workflow and reagents will remain the same for standard Illumina TruSeq library prep, custom solid-phase synthesized adapters, replacing all Cs with deamination-resistant cytosine analogs, such as 5pyCs, will be used in place of standard Illumina adapters. Although the workflow described can be used for Illumina libraries, adapters should be utilized to pre-adapt any sequencing adapters before A3A or bisulfite based sequencing approaches. In preferred embodiments, given the preference of the CxMTase for introducing 5cxmC at unmodified CpGs when the opposite strand contains a 5mCpG, this idealized substrate can be generated by a single copy step of the template strand using Klenow (exo-) polymerase or another displacing polymerases, along with 5mdCTP in lieu of dCTP in the dNTP mix.

Sheared DNA is re-quantified by Qubit and <20 ng (either preadapted or not) is reacted with >1 µM (final concentration) M.MpeI N374K and 160 µM CxSAM at 37° C. and denatured at 95° C. Proteinase K is briefly added to the reaction mixture at 37° C. Purification with SPRI beads (1.6× v/v, Beckman). A second round of carboxymethylation is performed with >1 µM M.MpeI N374K or M.MpeI second generation enzyme (Example III) and 160 µM CxSAM. After denaturation at 95° C., Proteinase K is briefly added to the reaction mixture at 37° C. and repurified with SPRI beads.

DNA is prepared as in ACE-Seq (Schutsky et al. Nature Biotechnology 2018). Briefly, DNA is glucosylated with T4-βGT and UDP-Glucose. DNA is then quickly snapfrozen to preserve single-stranded DNA. DMSO, concentrated (>2 µM final concentration) MBP-A3A-His or WT A3A, and A3A reaction buffer (35 mM SPG pH 5.5, 0.1% Tween-20, final concentration) is added to the reaction mixture. DNA is then concentrated with an Oligo Clean and Concentrator column (Zymo). In the standard embodiment of this method (without preadapted DNA), post A3A treated DNA is then prepared with any post-bisulfite adapter ligation strategy such as the Accel NGS Methyl-Seq kit (Swift). Optionally, locus-specific analysis can be performed with direct amplification of either post A3A treated DNA or library prepped DNA at loci of choice using bisulfite primers. Reads can be sequenced on any sequencing platform and can be additionally aligned using any bisulfite-sequencing based bioinformatic strategy.

The following examples are provided to illustrate certain embodiments of the invention. They are not intended to limit the invention in any way.

Example I

Discovery and Characterization of a Neomorphic M.MpeI CpG DNA Carboxymethyltransferase Epigenetic modification of nucleic acids at CpG regions is effective to control gene expression. Described herein is a variant of an MTase, M.MpeI, whose structure bound to DNA, has been solved thus offering a means for semirational exploration of active site determinants of reactivity. We first focused on Asn374 of M.MpeI to assimilate two competing observations from the literature. The Asn sidechain, which is heavily conserved across cytosine MTases, has been proposed to act as part of a network of H-bonds with active site water molecules that could help drive elimination (FIG. 2A). (10, 11) Despite this model, however, mutation of this Asn to Ala is tolerated in homologous MTases, and these mutants permit transfer of bulky SAM analogs in vitro. (12) We thus pursued saturation mutagenesis of N374 as an unbiased way to understand its core role in MTase catalysis.

Figure 3A:
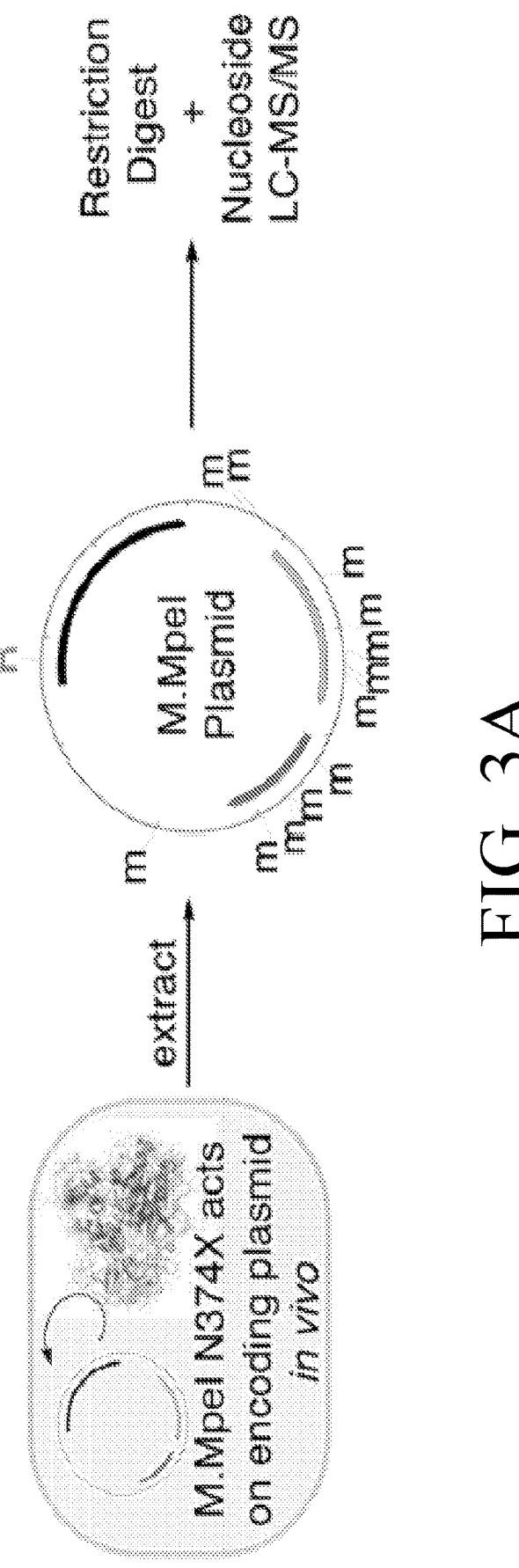
FIGS. 3A-3D. M.MpeI mutants create 5-carboxymethylcytosine (5cxmC).

We performed an in vivo activity screen that relies upon the linkage of the M.MpeI mutant genotype with a cytosine methylating phenotype. We separately transformed each of the twenty N374X variants, along with a C135S catalytic mutant, into _E. coli_. After inducing expression, the plasmids were recovered and analyzed by restriction digestion to assess the ability of each MTase to modify its own encoding plasmid in vivo (FIG. 3A). The extracted plasmids were then digested with one of two C<u>C</u> GG recognizing restriction enzymes, HpaII and MspI. HpaII is methylation-sensitive and blocked by any covalent modification at the 5-position of the underlined cytosine. The isoschizomer MspI is methylation-insensitive and was intended to serve as a positive control for methylation (FIG. 2B).

In our in vivo screen, for the majority of our variants, both HpaII and MspI digestion patterns were similar to WT M.MpeI, suggesting that quantitative conversion to C<u>5mC</u> GG was achieved. Partial protection, suggesting impaired catalysis, was observed with hydrophobic (3-branched (Ile/Val), constrained (Pro), or bulky aromatic (Phe/Tyr/Trp) mutations at position N374. Surprisingly, in both positively-charged variants, N374K and N374R, there emerged a faint ~2 kB band resistant to MspI digestion, inconsistent with cytosine methylation (FIG. 2B, red arrows). Upon reexamination of the plasmid map, we found that a C<u>C</u> GG protection event at position 895 could account for a 2057 bp band, leading us to consider the possibility that this position was modified by something other than methylation (FIG. 2C, red).

Figure 3B:
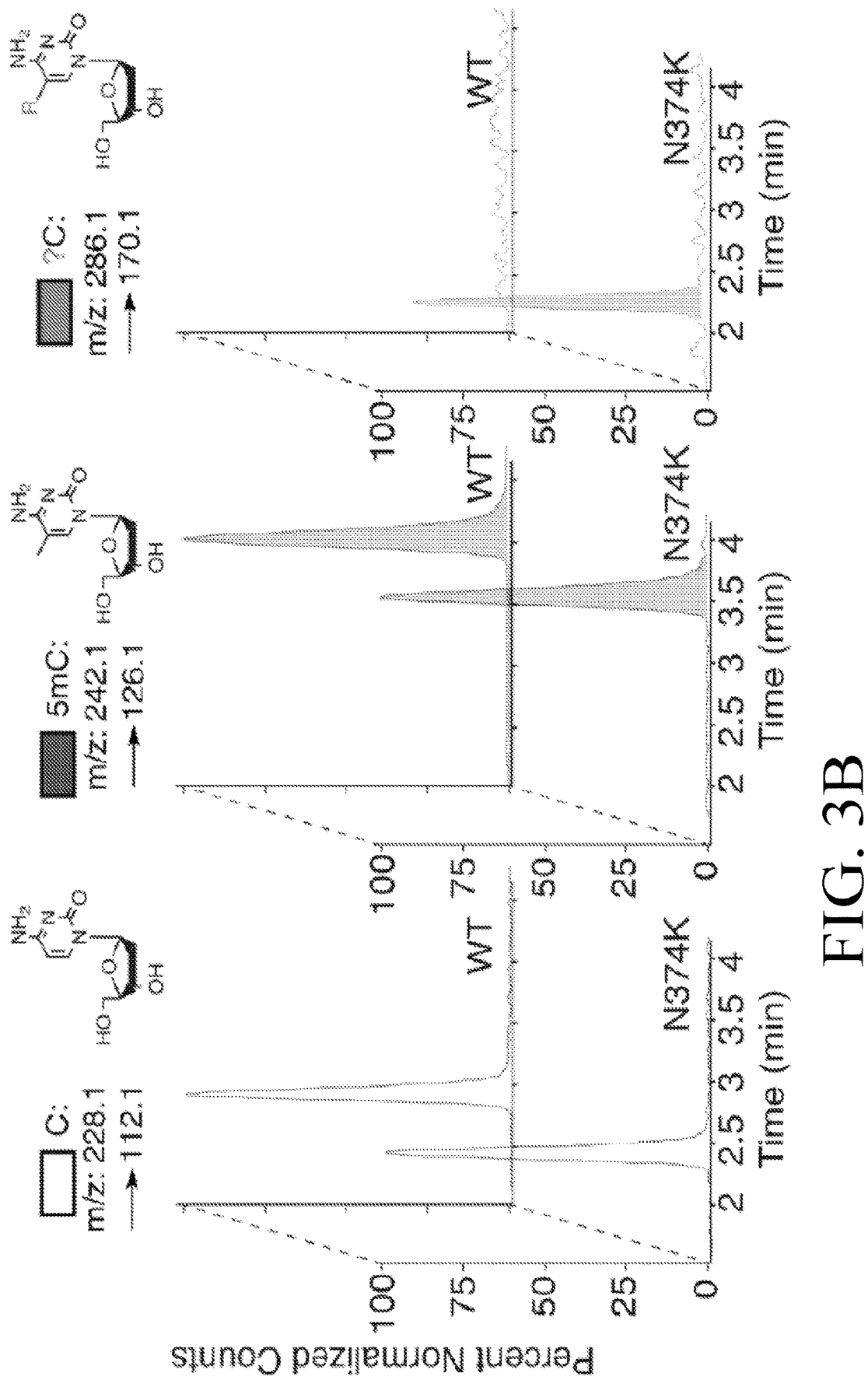
Figure 4:
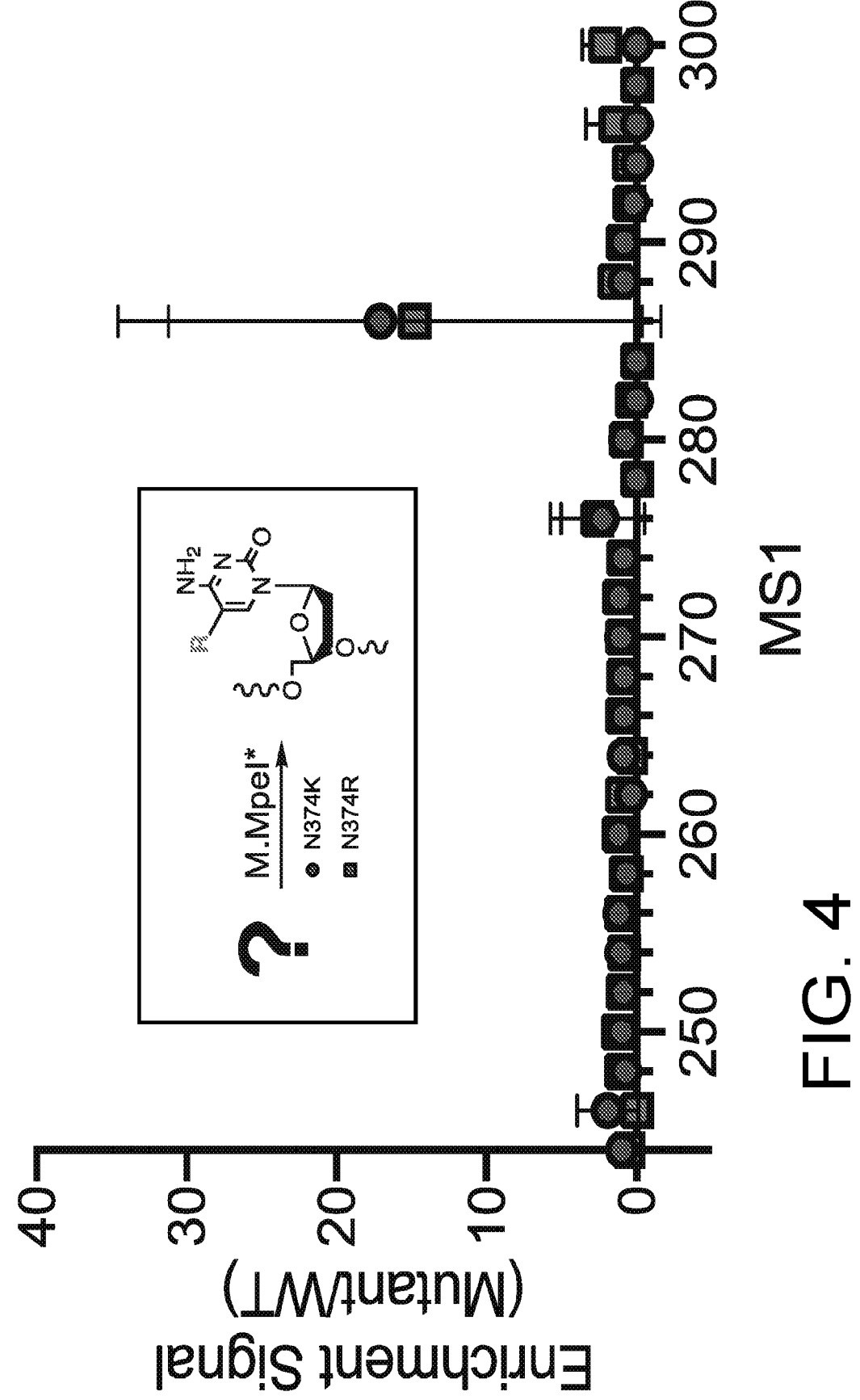
FIG. 4. LC-MS/MS scan identifies a candidate mass (m/z=286.1) for a new modification made by M.MpeI N374K and N374R mutants. Plasmids after overexpression of N374K, N374R, and WT M.MpeI variants were individually degraded to their component nucleosides. The samples were analyzed by LC-MS/MS using Multiple Reaction Monitoring (MRM) mode to simultaneously collect peaks corresponding to mass transitions larger than 5mC (m/z=242.1). The enrichment signal is the ratio of the total signal at a given mass transition for the mutant over that of the WT M.MpeI. Signals were normalized for relative comparisons across conditions, but this strategy does not allow for absolute quantification. Error bars represent propagated s.e. (n=2 biological replicates, same cultures as FIG. 2).

While MspI cleaves 5mC, it is blocked by bulkier modifications such as the naturally-occurring oxidized 5mCs. (13) To explore the possibility that we were detecting a new DNA modification, we degraded each plasmid to its individual nucleosides and performed LC-MS/MS for nucleosides larger than 5mC (m/z: 242.1→126.1 (FIG. 4). In N374K and N374R mutants but not WT or C135S, we identified a peak with unique retention time of 2.2 min and m/z: 286.1→170.1 (FIG. 3B).

Figure 3C:
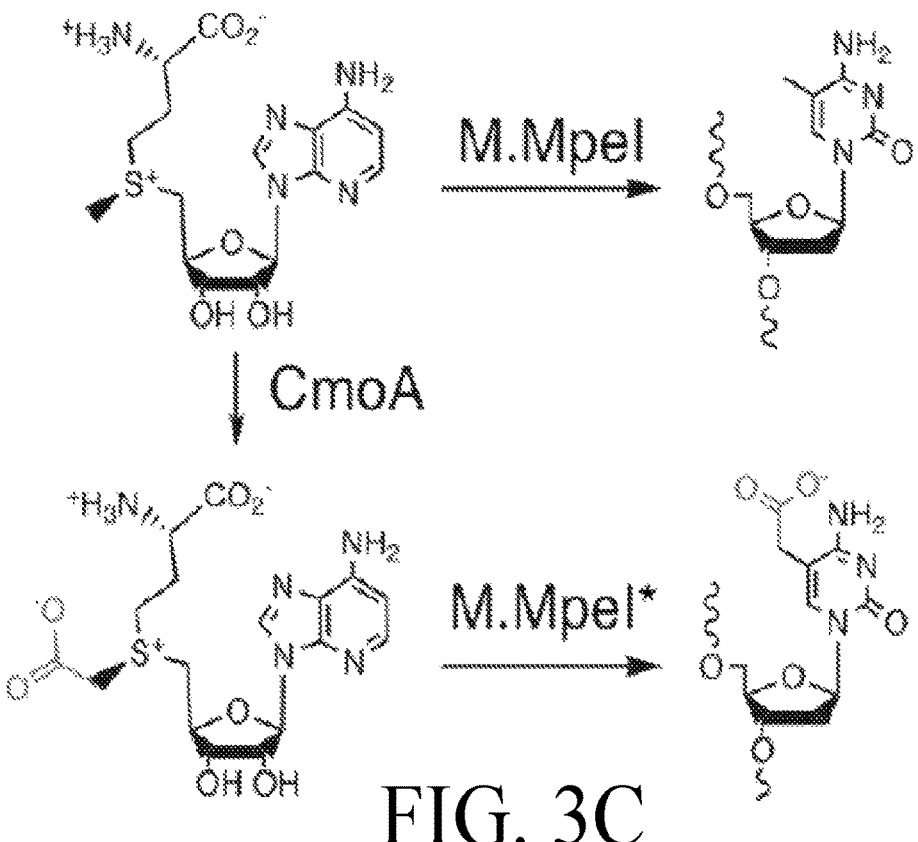
Figure 3D:
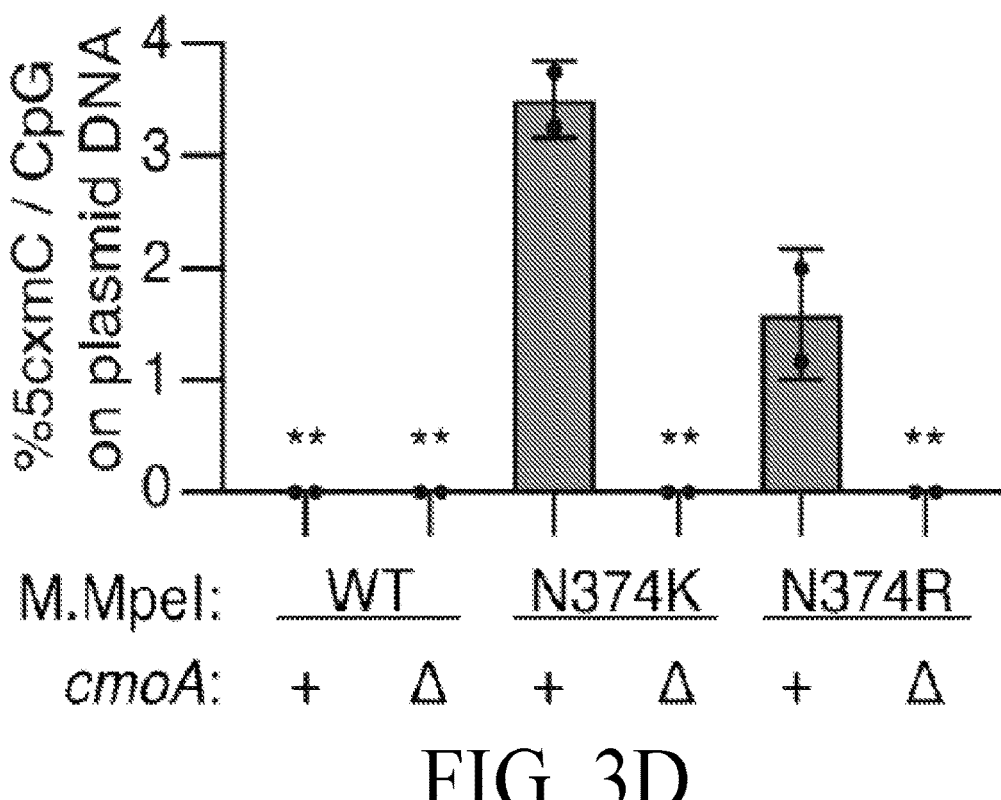

We next identified carboxy-S-adenosyl-L-methionine (CxSAM) as a candidate metabolite that could be involved in creating both the restriction digestion pattern and LC-MS/MS signal. CxSAM is a sparse metabolite in _E. coli_ generated from SAM and prephenate by the non-essential enzyme CxSAM synthase (CmoA) and has recently been shown to be involved in tRNA modifications of uridine in _E. coli_. (14) Although CxSAM is 400-fold less prevalent than SAM in vivo (~0.5 µM vs. 200 we noted that the reaction of CxSAM with a target cytosine would yield 5-carboxymethylcytosine (5cxmC), a modification consistent with the observed m/z: 286.1170.1 (FIG. 3C). To rigorously assess if CxSAM was in fact the substrate for our mutant MTase in vivo, we generated a cmoA knockout strain. While in vivo plasmid carboxymethylation by both M.MpeI N374K and N374R can be detected in the cmoA _E. coli_ strain by LC-MS/MS, these signals are lost in the ΔcmoA strain (FIG. 3D). Thus, this novel modification is 5cxmC and is solely derived from the activity of mutant M.MpeI using endogenous CxSAM.

Figures 5A, 5B:
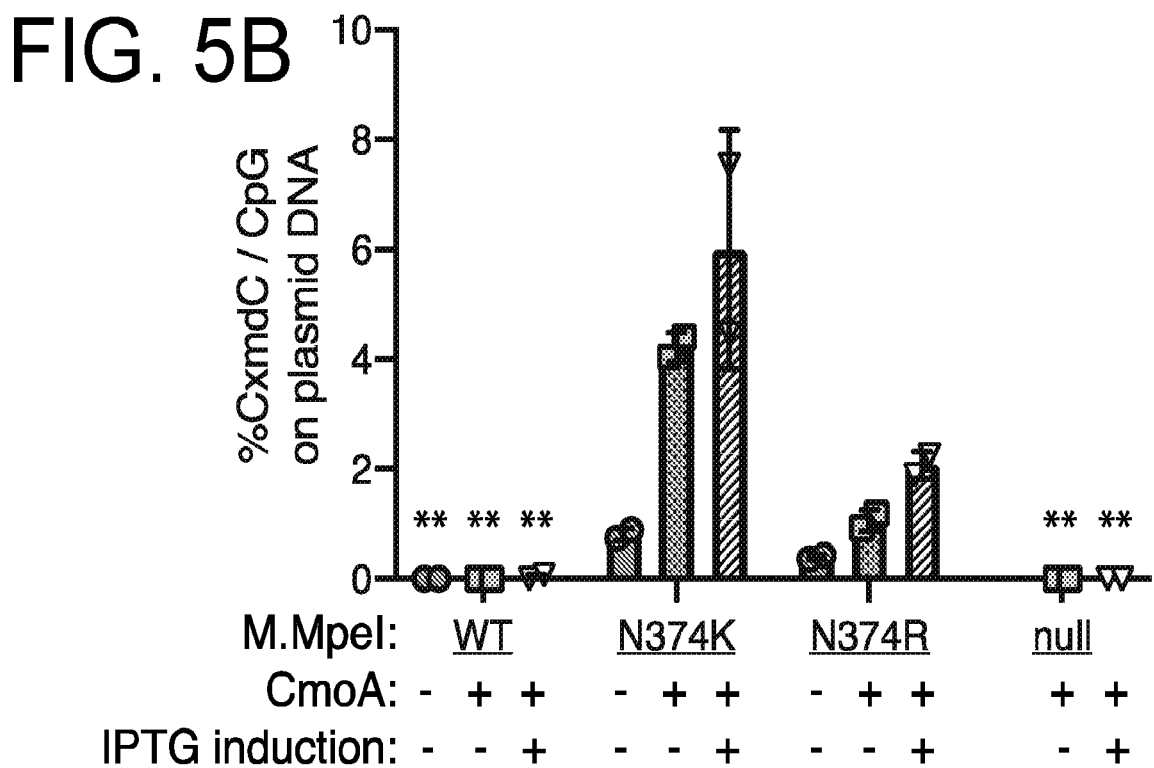
FIG. 5. Overexpression of CmoA increases levels of 5cxmC in M.MpeI mutants. a) In vivo synthesis of 5cxmC can be enhanced by CmoA overexpression (thick arrows) with IPTG inducible ASKA collection plasmid. b) Plasmid DNA was degraded to its component nucleosides and 5cxmC, reported as a percent of total CpG sites, was detected by LC-MS/MS. Graphs show mean±s.d. (n=2 biological replicates). **limit of detection=0.33 fmol.

To complement our findings with the ΔcmoA strain, we introduced a plasmid that could inducibly overexpress CmoA. By LC-MS/MS, both N374K and N374R but not WT M.MpeI showed an increase in 5cxmC signal in the added presence of the CmoA plasmid (FIG. 5). Of the mutants assessed, M.MpeI N374K showed the greatest level of 5cxmC modification across overexpression conditions while WT M.MpeI showed no detectable 5cxmC under any condition.

Figure 7A:
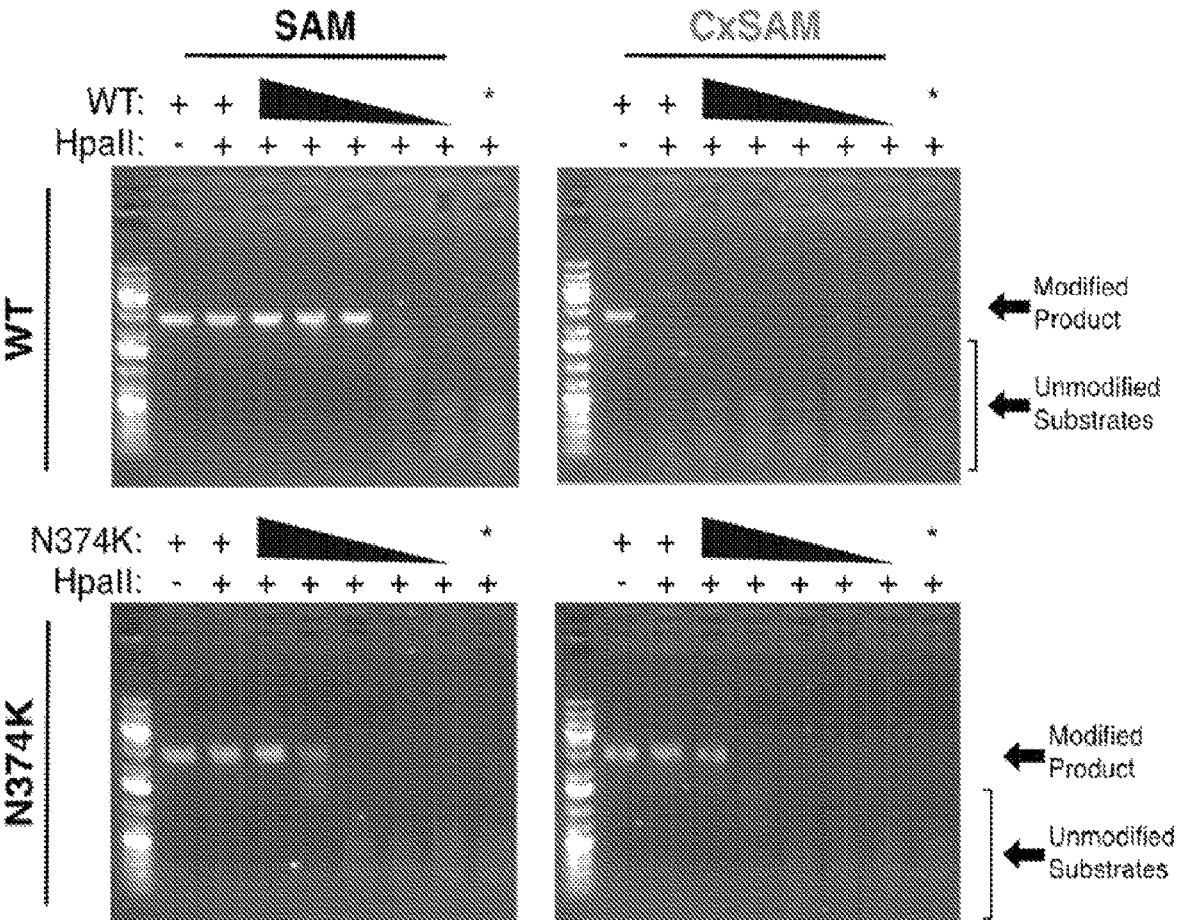

Having established the identity and in vivo origin of the new base 5cxmC, we aimed to reproduce this activity in vitro. We expressed and purified both the WT and N374K M.MpeI variants and synthesized CxSAM as a diastereomeric mixture (FIG. 6). We then incubated enzyme with a pUC19 plasmid DNA substrate and either SAM or CxSAM. After this reaction, the plasmids were assessed for modification with HpaII (C<u>C</u> GG, 13 sites), a modification-sensitive restriction enzyme (FIG. 7). These substrates were additionally incubated with HhaI (G<u>C</u> GC, 17 sites) to control for activity in two different CpG contexts. Consistent with our in vivo analysis, WT M.MpeI is capable of completely protecting the pUC19 plasmid with SAM, but no protection was noted upon reaction with CxSAM. N374K, by contrast, transfers SAM less efficiently than the WT enzyme but newly gains the ability to transfer CxSAM.

Figures 7B, 7C:
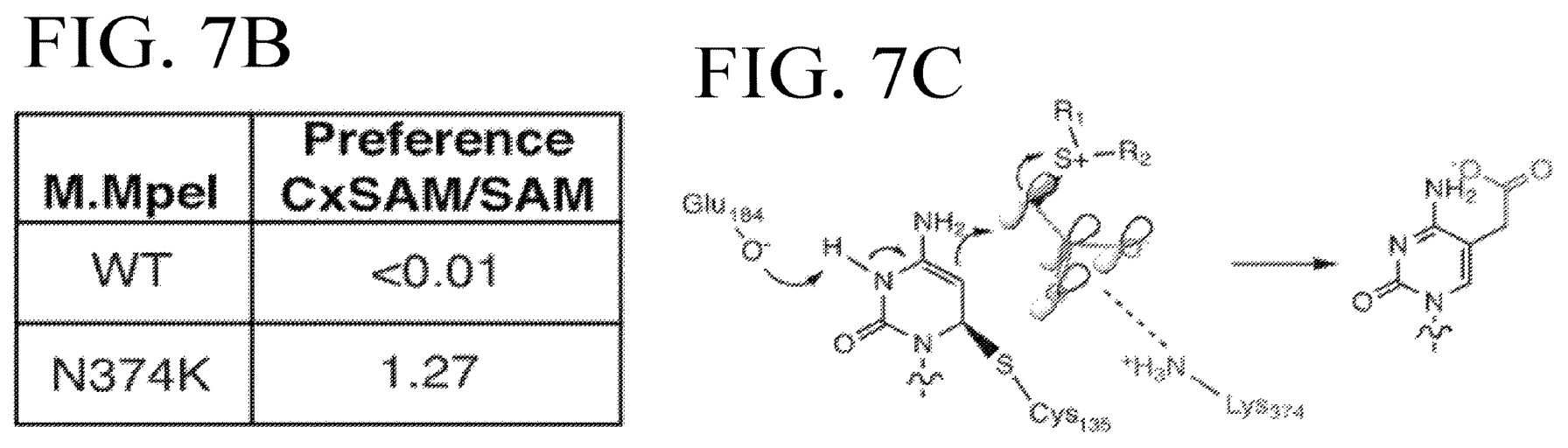
Figure 8A:
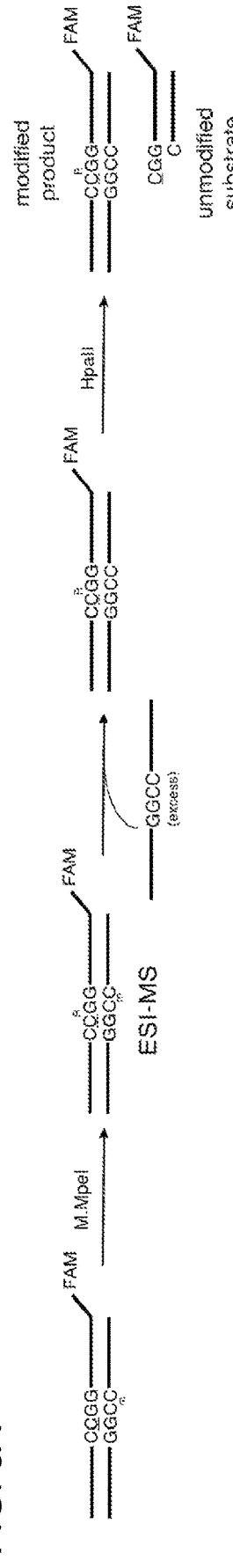
FIGS. 8A-8C. Quantitative oligonucleotide assay. Assay design was previously validated with homologous methyltransferases.
Figure 8B:
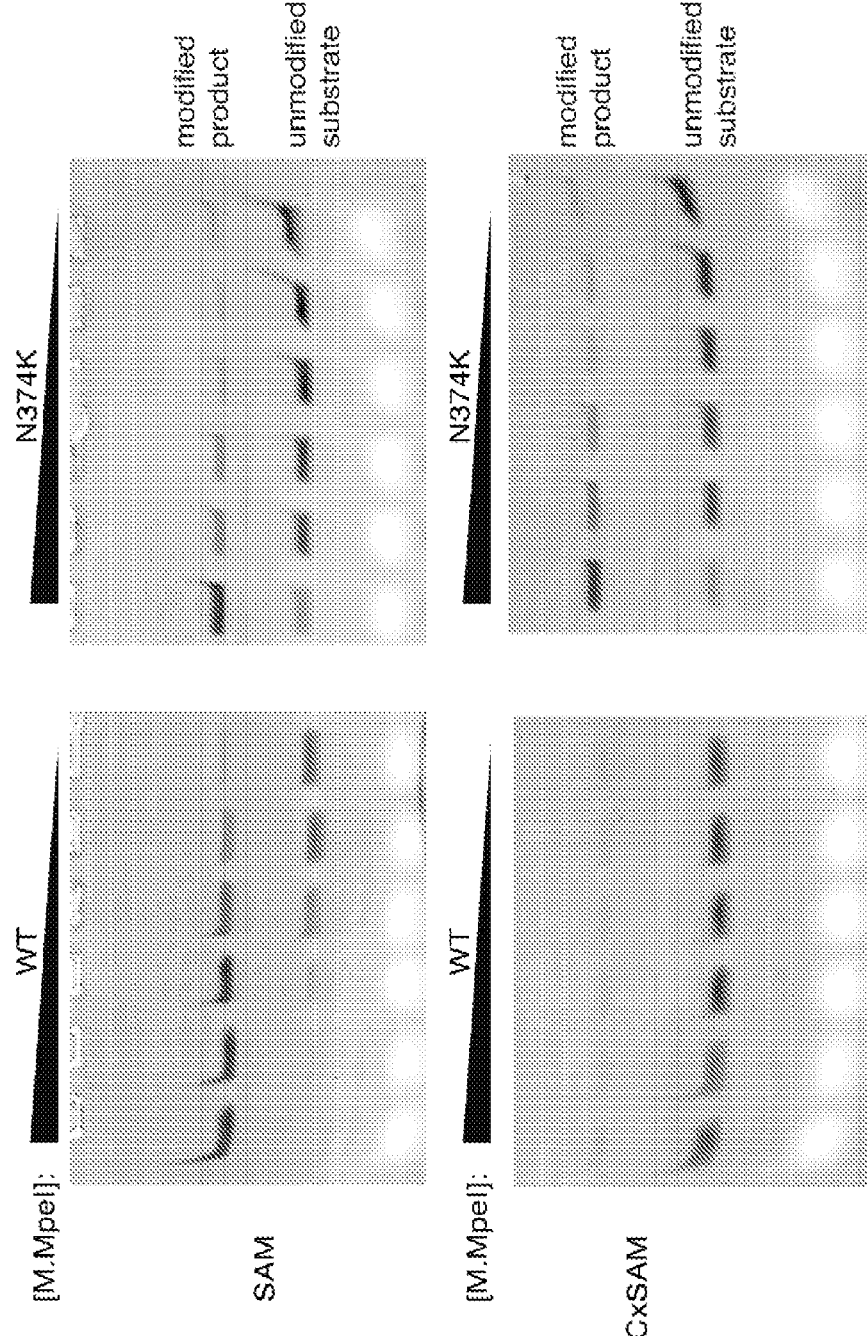
Figure 8C:
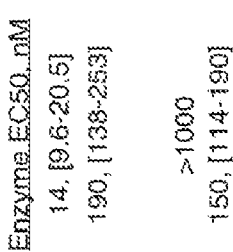
Figure 8C:
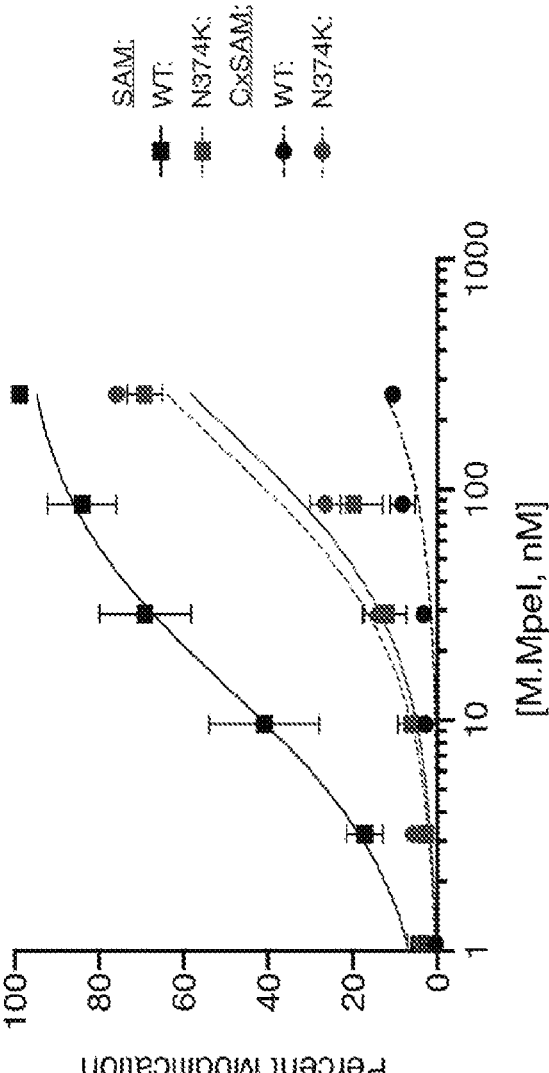

For a more quantitative comparison of in vitro activity, we devised an oligonucleotide-based assay, whereby modification of a CpG on a fluorophore labeled strand can be tracked by monitoring its resistance to HpaII digestion (FIG. 8A). (19) Consistent with the prior pUC19-based assay, we found that for WT M.MpeI, only SAM and not CxSAM was a substrate. For the N374K variant, CxSAM was 1.3-fold preferred over SAM (FIG. 7B, FIG. 8B, 8C). While our in vitro studies show a modest preference for CxSAM over SAM in our neomorphic enzyme, our in vivo experiments suggest that the oligonucleotide assay may underestimate the extent of this preference, possibly due to our inability to separate CxSAM diastereomers or other factors that enhance in vivo CxSAM selectivity.

Figure 7D:
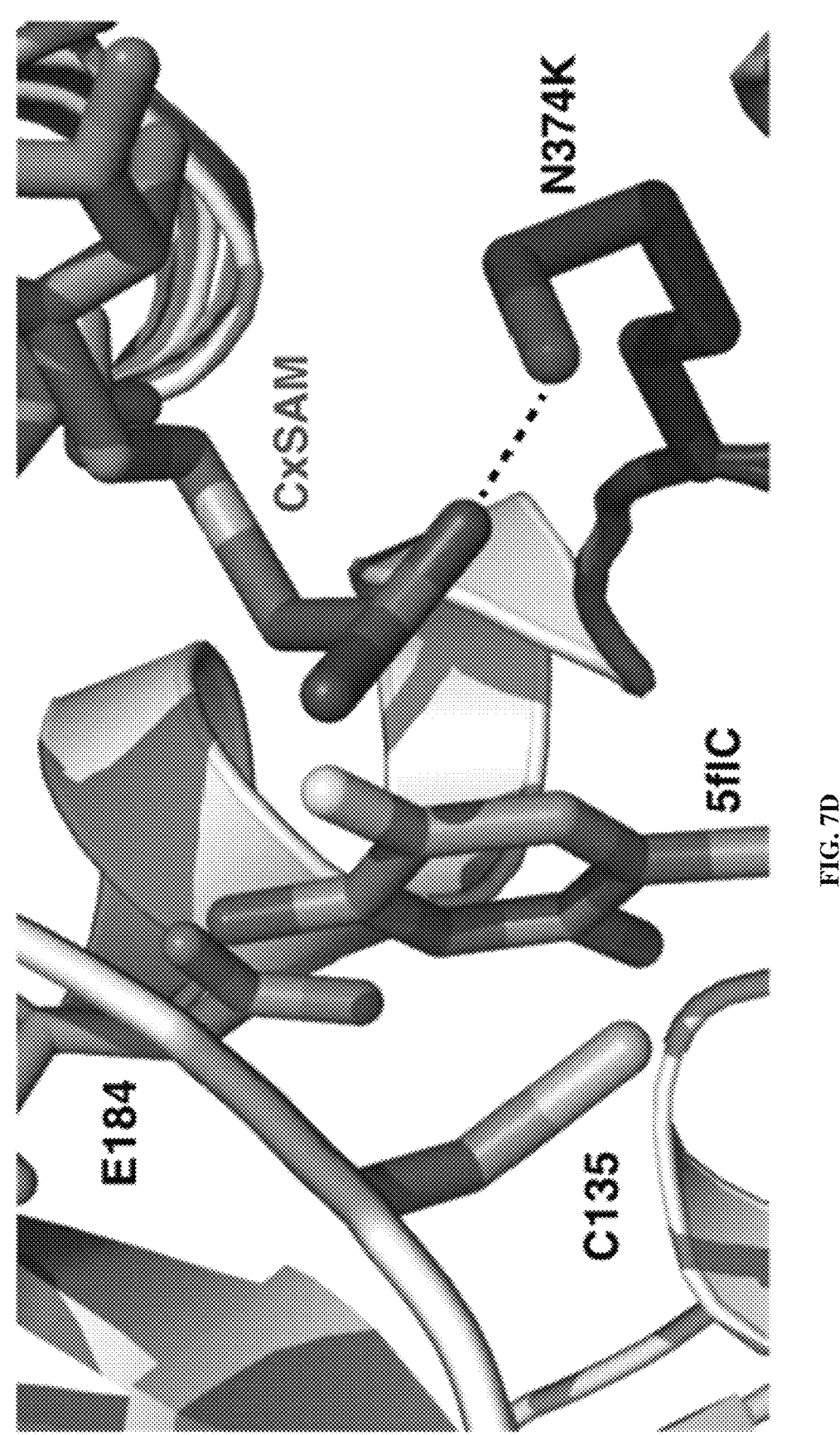

Prior work with synthetic SAM analogs has suggested that transfer can be promoted by the presence of a conjugated π-system at the β-carbon relative to the electrophilic carbon (FIG. 7C). (20) This mechanism alone, however, would be unlikely to fully explain our observed selectivity. To better understand the molecular basis for mutant-specific reactivity, we turned to the crystal structure of M.MpeI with S-adenosyl-L-homocysteine (SAH) bound and manually overlaid CxSAM in place of SAH (FIG. 7D). Here, we observed that a mutant Lys374 could form a putative salt bridge with the carboxylate anion of CxSAM, offering a likely explanation for this enzyme's ability to accept this substrate. Thus, this variant is distinctive from any prior mutagenesis done on related DNA MTases, where mutations were made to increase the size of the active site pocket. Such mutation in the DNA MTase M.SssI have been used to transfer bulky substituents, but do not take advantage of the salt bridge interactions in our engineered system that allow for the generation of this new DNA base, 5cxmC.

Example II

Figure 9:
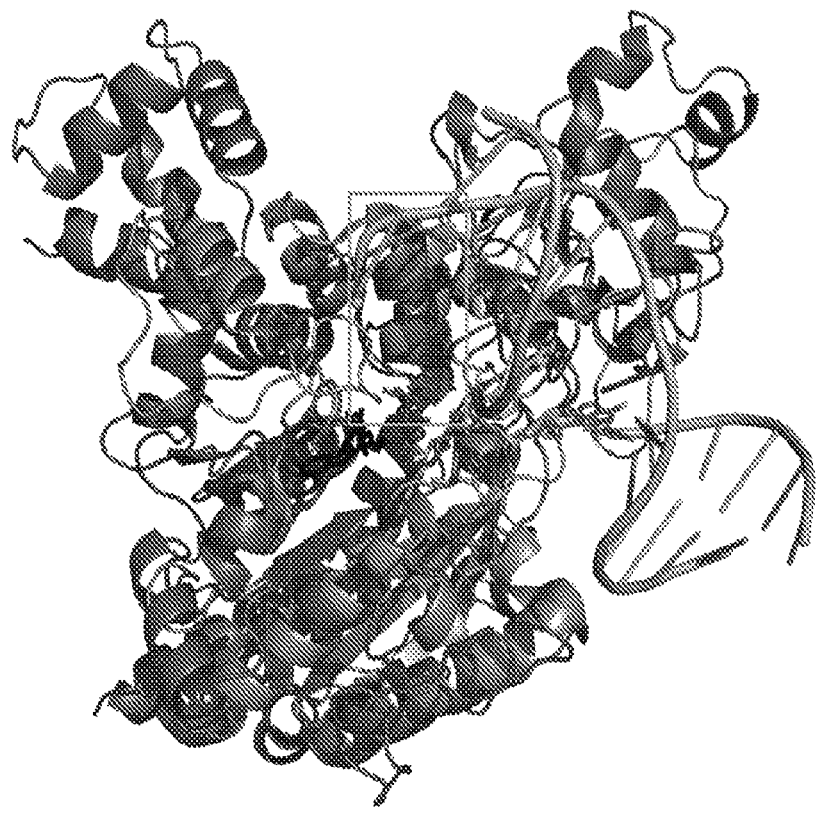
FIG. 9. PyMOL structural alignment of M.MpeI and Dcm. M.MpeI (gray, PDB: 4DKJ) (SEQ ID NO: 12) with predicted model of Dcm (purple, Swiss-Model: POAED9)(SEQ ID NO: 11). The residues shown correspond to the beginning of Motif X in cytosine family MTases. The boxed green portion labels an aligning alpha-helix within the enzyme active site which contains the blue Asn436 (N) residue that sits adjacent to carbon 5 of the target cytosine, in an analogous position to Asn374 of M.MpeI.
Figures 10A, 10B, 10C:
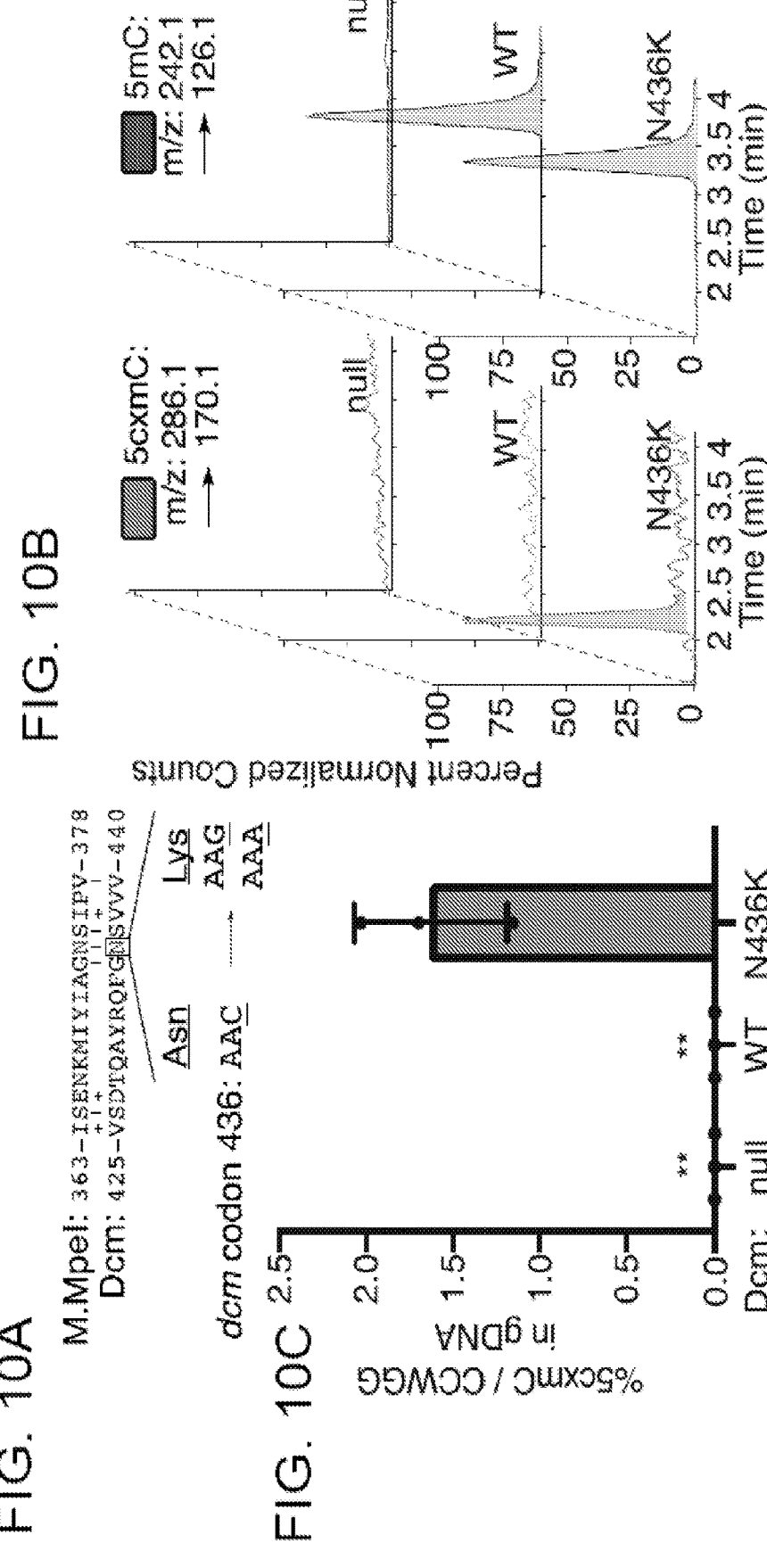
FIGS. 10A-10C. Mutation of E. coli's endogenous methyltransferase Dcm shows gain-of-function (neomorphic) ability to carboxymethylate genomic DNA in vivo.

Generalizability of Neomorphic DNA CxMTase Activity to a Homologous MTase and Generation of an _E. coli_ Strain with Genomic 5cxmC Given this structural model for cytosine carboxymethylation, we wondered if this new activity was also accessible for homologous MTases. We specifically chose to focus on _E. coli_'s naturally occurring DNA Cytosine Methyltransferase (Dcm) because this enzyme provides insight into the question of whether a native strain with available CxSAM can be partnered with a mutant version of its native DNA MTase in order to populate the genome with a novel unnatural DNA base. While M.MpeI is native to *Myco-plasma penetrans* and generates 5mC in the CpG context, Dcm generates 5mC in CCWGG (W=A or G) contexts. When comparing these enzymes, structural alignment showed that despite differences in sequence recognition loops, there is significant active site overlap, with Dcm Asn436 and M.MpeI Asn374 similarly positioned adjacent to carbon-5 of the target cytosine (FIG. 9). We further noted that only a modest single nucleotide change in the wobble position of codon 436 in dcm could create an N436K mutation (FIG. 10A).

Encouraged by our elucidation of the mechanism of M.MpeI-mediated DNA carboxymethylation and employing this newly identified structural alignment, we moved to dam⁻/dcm⁻ *E. coli* and introduced either WT Dcm or the N436K variant on a plasmid. After induction of MTase expression, we extracted the genomic DNA (gDNA) and performed nucleoside LC-MS/MS to evaluate for DNA modification in vivo (FIG. 10B). In this setting, both the WT and N436K enzymes could methylate cytosine, as determined by detection of 5mC. However, the N436K mutant enzyme and not WT enzyme could catalyze the formation of 5cxmC in the native *E. coli* genome. Quantification of 5cxmC showed that >1.5% of the CCWGG sites were carboxymethylated (FIG. 10C). Given the extensive conservation of the active site Asn in homologous MTases, these findings indicate that this residue may have neomorphic potential across the cytosine MTase family. Furthermore, our results highlight that a single point mutation in the native dcm coding sequence is sufficient to result in the creation of an unnatural DNA modification in *E. coli*.

Given the extensive conservation of the active site Asn in homologous MTases, these findings additionally indicate that this residue may have neomorphic potential across the cytosine MTase family (FIG. 11B, arrow). Specifically, while Dcm and M.MpeI are only 22% identical by BLAST alignment, they share a similar fold which contains the conserved Motif X shown in FIG. 11B. This motif most commonly contains a GNS tripeptide where the position aligning to the conserved N in Dcm was mutated to create a neomorphic carboxymethyltransferase. This process of turning a MTase into a CxMTase could be repeated for any MTase, known or unknown, and involves a BLAST alignment of the MTase to known MTase, such as Dcm or M.MpeI, and targeting of the residue aligning with the Asn for mutation to a Lys or Arg.

To our knowledge, these experiments represent the first report of a novel DNA base derived exclusively from the native metabolome. The realization that our findings occupy a distinct space relative to similar, yet methodologically divergent synthetic biology efforts has afforded us unique insights into the chemical determinants of genomic composition and evolution and addition technology development (Example 3).

Figure 11A:
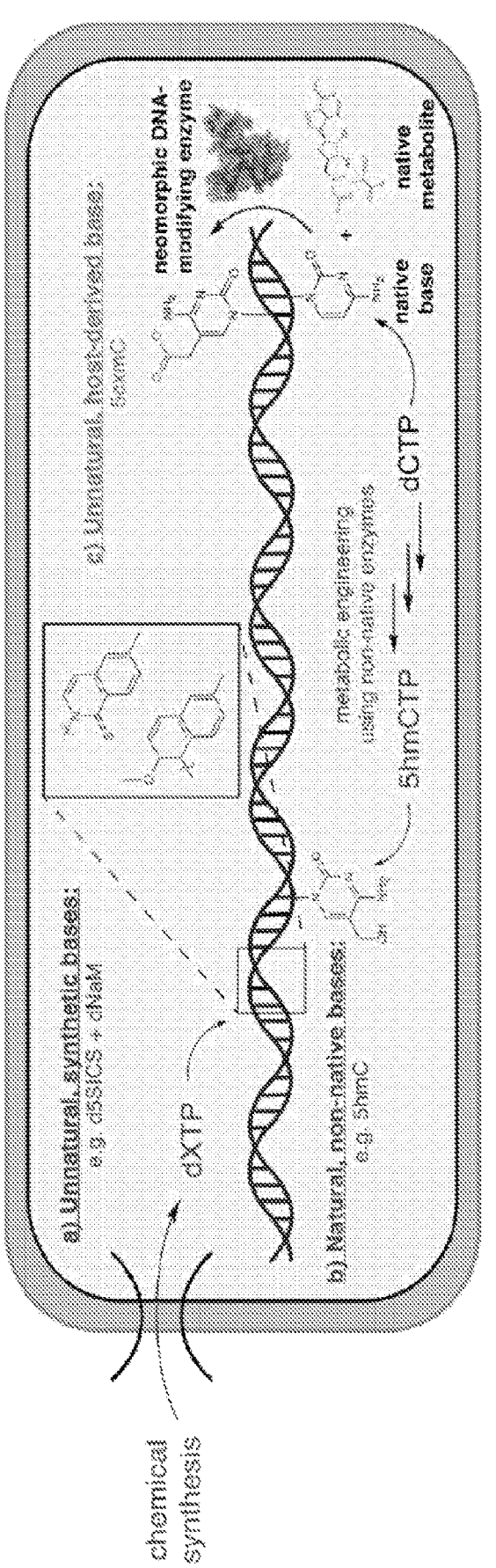
Figure 11B:
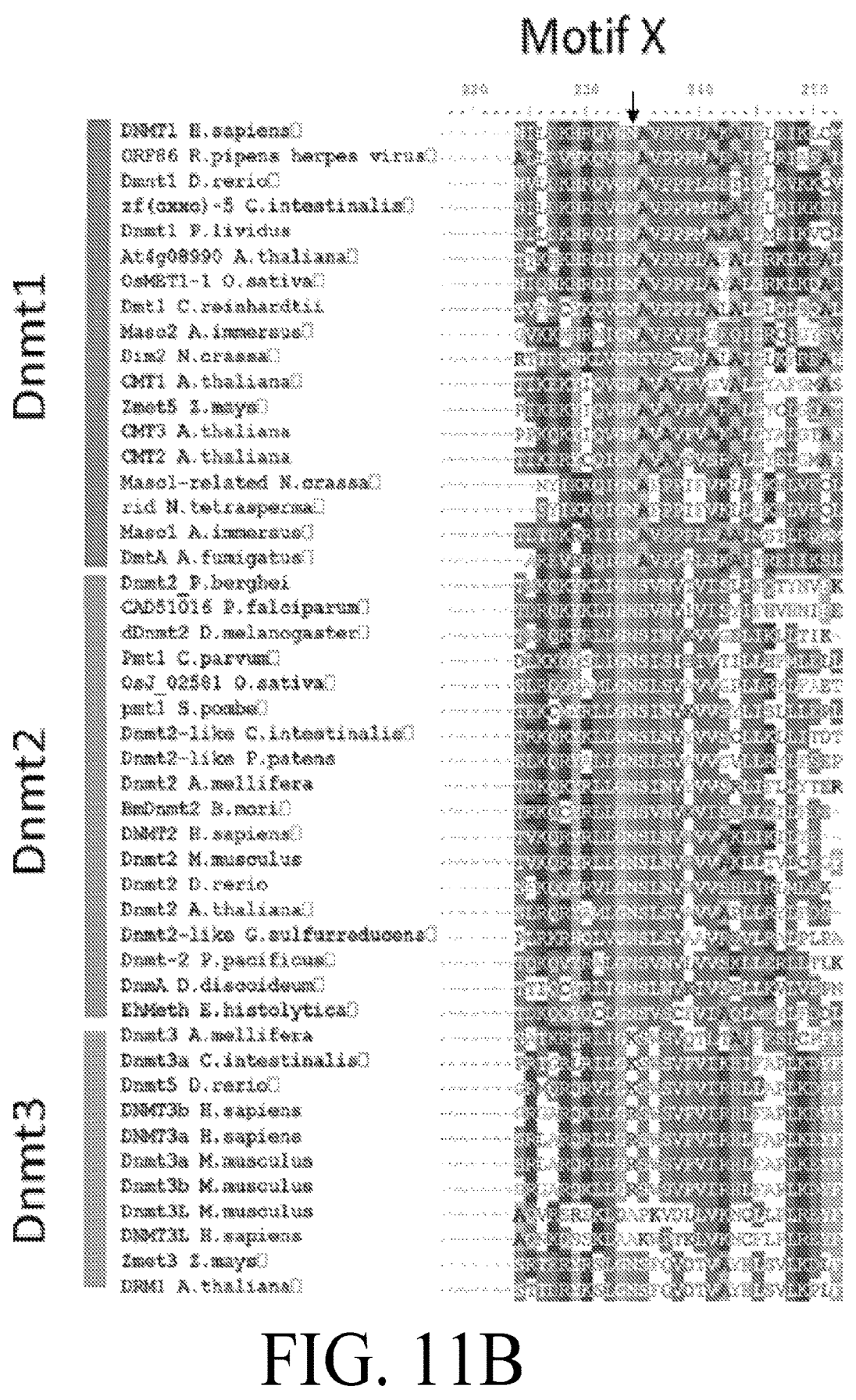

Non-canonical nucleobases can originate from a variety of sources (FIG. 11A). While prior efforts have shown that synthetic and non-native sources of dNTPs can be used to create new bases in vivo, this study identifies the extended metabolome as an underappreciated source of genomic diversification.

Although metabolites have been well documented to potentiate or inhibit the production of naturally occurring modified nucleobases, very rarely are they considered as substrates which can directly be used to modify genomic DNA. An interesting exception is provided by ascorbic acid (vitamin C), which was recently shown to be an unexpected co-substrate for generating the natural, modified base 5-glycerylmethylcytosine in the algae *Chlamydomonas reinhardtii*. In the case of CxSAM, while no role in DNA modification was previously known, the metabolite has been previously shown to act as a direct substrate for uridine modification in tRNA and small molecule cofactor modifications. These important precedents helped us to uncover that CxSAM can also be used to modify genomic DNA in concert with neomorphic, mutant DNA MTases.

Notably, M.MpeI CmoA overexpression resulted in higher levels of 5cxmC, suggesting that metabolic manipulations can be used to widen selectivity windows (FIG. 5). From the standpoint of technology development, this is an important observation because the synthetic SAM analog field continues to expand to include creative applications that currently are predominantly limited to in vitro settings. Given this study and others, it is now more feasible to consider whether SAM analogs with useful chemical handles can be employed to covalently modify gDNA in vivo, despite their inevitable competition with native SAM. Our engineered *E. coli* stain can therefore likely be further modified to increase the prevalence or stability of the 5cxmC base in the genome.

Figure 11B:
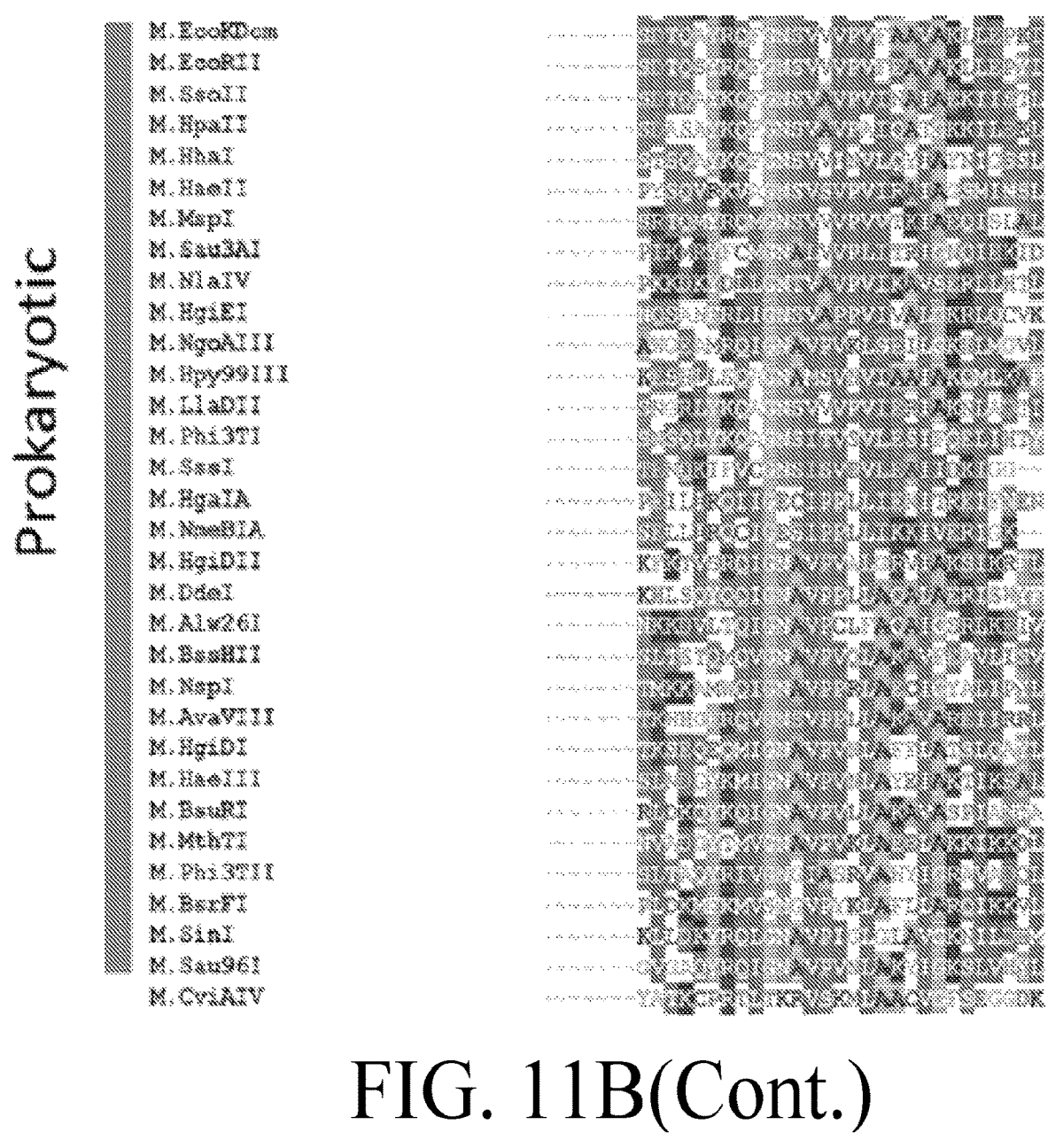

Our findings address how to generate an organism with a new, modified nucleobase from redirection of natural metabolites to make a bacteria that harbors a new DNA base 5cxmC. It is also notable that the new modification 5cxmC, but not 5mC, showed a gain-of-function ability to resist digestion by the modification-sensitive endonuclease MspI. Given the growing body of evidence that suggests that restriction-modification systems have the capacity to coevolve, it is feasible that selection focused on 5cxmC could be harnessed to improve the stability and abundance of 5cxmC modifications in vivo and simultaneously provide a selection platform for other new neomorphic carboxymethyltransferases (See FIG. 11 for candidates and criteria).

References for Example I & II

1. Krueger, A. T. & Kool, E. T. Chemistry & Biology 16, 242-248 (2009).
2. Malyshev, D. A. et al. Nature 509, 385-388 (2014).
3. Mehta, A. P. et al. Journal of the American Chemical Society 138, 14230-14233 (2016).
4. Mehta, A. P. et al. Journal of the American Chemical Society 138, 7272-7275 (2016).
5. Nabel, C. S., Manning, S. A. & Kohli, R. M. ACS Chem. Biol. 7, 20-30 (2012).
6. Wilson, G. G. & Murray, N. E. Annual Review Genetics 25, 585-627 (1991).
7. Sanchez-Romero, M. A. & Casadesús, J. Nature Reviews Microbiology 18, 7-20 (2020).
8. Iyer, L. M., Abhiman, S. & Aravind, L. Prog. Mol. Biol. Transl. Sci. 101, 25-104 (2011).
9. Wojciechowski, M., Czapinska, H. & Bochtler, M. Proceedings of the National Academy of Sciences 110, 105-110 (2013).
10. Zhang, X. & Bruice, T. C. Proceedings of the National Academy of Sciences 103, 6148-6153 (2006).
11. Jurkowski, T. P. & Jeltsch, A. PLOS ONE 6, e28104 (2011).
12. Lukinavicius, G., Lapinaite, A., Urbanaviciute, G., Gerasimaite, R. & Klimasauskas, S. Nucleic Acids Res. 40, 11594-11602 (2012).
13. Liu, M. Y., DeNizio, J. E. & Kohli, R. M. Methods Enzymol. 573, 365-385 (2016).

25

14. Kim, J. et al. Nature 498, 123-126 (2013).

15. Kim, J. et al. Nucleic Acids Res. 43, 4602-4613 (2015).

16. Baba, T. et al. Mol. Syst. Biol. 2, 2006.0008 (2006).

17. Kitagawa, M. et al. DNA Res. 12, 291-299 (2005).

18. Serebryakova, M. et al. Journal of the American Chemical Society 138, 15690-15698 (2016).

19. Nabel, C. S., Denizio, J. E., Carroll, M. & Kohli, R. M. Biochemistry 56, 2166-2169 (2017).

20. Dalhoff, C., Lukinavicius, G., Klimasauskas, S. & Weinhold, E. Nat. Chem. Biol. 2, 31-32 (2006).

21. Xue, J. H. et al. Nature 569, 581-585 (2019).

22. Zhang, Y. et al. Proceedings of the National Academy of Sciences 114, 1317-1322 (2017).

23. Zhang, Y. et al. Nature 551, 644-647 (2017).

24. Chin, J. W. Annual Review of Biochemistry 83, 379-408 (2014).

25. Schutsky, E. K. et al. Nat. Biotech. 36, 1083-1090 (2018).

26. Miller, J. H. (Cold Spring Harbor Laboratory Press, Plainview, N.Y., 1992).

27. Kubiak, J. M. et al. ACS Synth. Biol. 6, 2067-2076 (2017).

28. Engler, C., Kandzia, R. & Marillonnet, S. PLOS ONE 3, e3647 (2008).

29. DeNizio, J. E., Liu, M. Y., Leddin, E. M., Cisneros, G. A. & Kohli, R. M. Biochemistry 58, 411-421 (2019).

30. Kim J, et al (2013) Nature 498(7452): 123-126.

31. Kim J, et al (2015) Nucleic Acids Research 43(9): 4602-4613.

32. Dang L, et al (2009) Nature 462(7274): 739-744.

33. Xu Q, et al (2016) PLoS One 11(8): e0161261.

Example III

Development and Application of Direct Methylation-Sequencing (DM-Seq) for Characterization of Epigenetic Methylation Modifications in Target DNA In mammalian genomes, modification of cytosines, typically in cytosine-guanine dinucleotides (CpGs), plays a significant role in shaping cellular identity. The best characterized modification is 5-methylcytosine (5mC), an important epigenetic regulator of gene expression involved in determining cell fate, silencing mobile genetic elements, and controlling genomic imprinting (1-5) (FIG. 12). The identification of several oxidized forms of 5mC (ox-mCs) arising through the action of the ten-eleven translocation (TET) family enzymes greatly expanded the complexity of the epigenome (6-9). Ox-mCs serve as intermediates in active DNA demethylation, whereby repressive 5mC markers are erased, and ox-mCs also likely have independent epigenetic functions (10). 5-hydroxymethylcytosine (5hmC) is by far the most abundant ox-mC, reaching levels as high as 40% of the levels of 5mC in certain cell types such as neurons (11). The highly oxidized bases 5-formylcytosine (5fC) and 5-carboxylcytosine (5caC) are far less common: when quantified in parallel with 5hmC in neurons, 5fC was maximally detected at levels more than 3 orders of magnitude less (11), while 5caC was undetectable (7,12).

As we have noted above, the most common methods for localizing cytosine modifications rely upon their differential chemical reactivity with bisulfite (BS) (13-15). With heat and under acidic conditions, unmodified cytosine bases in single-stranded DNA (ssDNA) are sulfonated, hydrolytically deaminated, and desulfonated under basic conditions

26

Figures 12A, 12B:
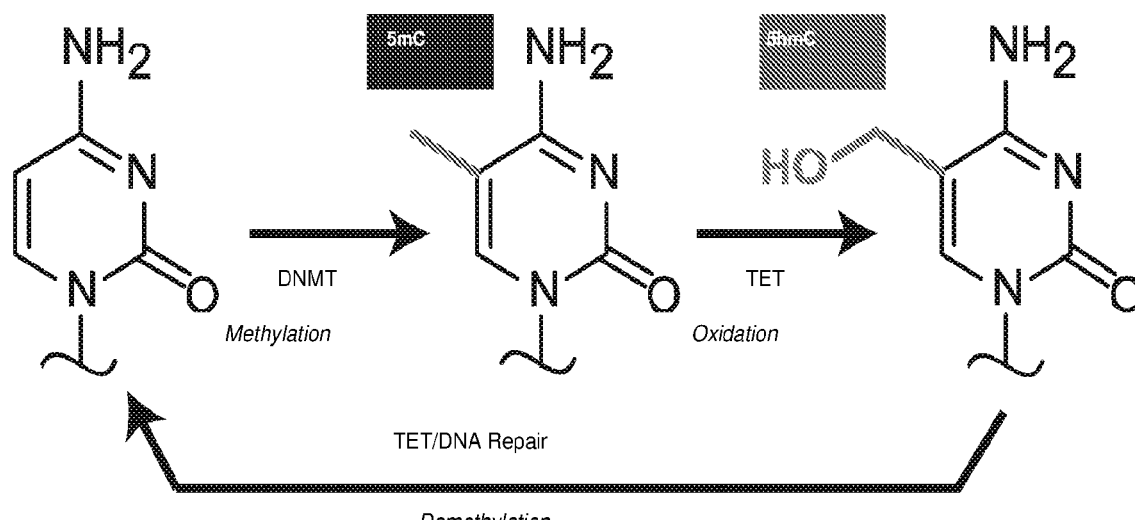
FIGS. 12A-12B. DNA cytosine modifications and their localization.

(16). 5mC is largely unreactive under these conditions offering a 'binary' readout in sequencing that discriminates C from 5mC. The historical reliance on BS-based methods is a key reason why 5hmC was overlooked for decades: in BS-Seq, 5hmC forms a bulky adduct that is slow to deaminate, rendering 5hmC indistinguishable from 5mC (17). To address this issue, novel methods have been developed to specifically detect 5hmC at single-base resolution. TAB-Seq involves protection of 5hmC by glucosylation with T4 β-glucosyltransferase (βGT) to generate 5-glucosylhydroxymethylcytosine (5ghmC). 5mC is then oxidized to 5caC with TET enzymes in vitro (18,19). The samples are then deaminated with bisulfite. As both C and 5caC deaminate, 5ghmC is left as the only base that reads as C in this 'binary' code (FIG. 12B). Another method, oxidative bisulfite sequencing (20), relies on indirect inference to localize 5hmC by comparison of BS-Seq before and after chemical oxidation with $KRuO_4$.

The major methodologies for localizing 5mC and 5hmC at base-resolution thus rely upon bisulfite. While these methods have offered great insights, they pose major barriers to the next era of epigenetics research—an era which will include a focus on low-input samples, down to single cells, and resolving cis-regulatory relationships across long-range genomic loci. Chemical deamination is destructive, introducing abasic sites into DNA due in part to the extremes of pH and temperature required. Quantitative PCR (qPCR) had validated that 96-99.9% of DNA is typically degraded (21,22) and only short contiguous sequences (<400 bp) can be typically amplified from the damaged DNA (23,24). While multiple solutions have been explored, each poses different challenges. BS-Seq has been accomplished down to single cell level, but the average coverage is sparse due to bisulfite-mediated degradation (25,26).

While BS continues to be used and is of use in establishing the accuracy of our method described below, DNA deaminases from the AID/APOBEC family offer a compelling alternative to bisulfite. These enzymes canonically function in deamination of unmodified cytosine in DNA to uracil and mediate critical adaptive and innate immune functions. Employing biochemical approaches, we established that one highly active family member, APOBEC3A (A3A), can proficiently deaminate C and 5mC, but discriminates against all ox-mCs (35,36), a mechanism corroborated by recent structures (Shi et al. Nature Structural and Molecular Biology 24, 131-139 (2017). Building on this insight, we devised ACE-Seq, a bisulfite-free method for sequencing 5hmC at base resolution that employs enzymatic, rather than chemical, deamination. ACE-Seq yielded base resolution 5hmC profiles in neurons with higher statistical confidence than TAB-Seq. Maps generated with 2 ng of input genomic DNA (gDNA) correlated with whole cortex TAB-Seq maps that required 3 μg of gDNA, a >1000-fold difference in input (39). Thus, ACE-Seq is non-destructive (FIG. 13), as enzymatic deamination, unlike chemical deamination with BS-Seq, does not lead to the introduction of abasic sites in DNA.

While ACE-Seq permits the non-destructive single base pair resolution mapping of 5hmC, both C and 5mC are converted by the DNA deaminase enzyme and are therefore not separable. Given the importance of mapping 5mC to understanding cellular identity or gene regulation, we have devised a new method, DM-Seq which includes use of an engineered methyltransferase, M.Mpel N374K to allow for 5mC to be directly and specifically localized for the first time. See FIG. 14.

In the method described herein, we have established an all-enzymatic sequencing approach to localization of 5mC. The non-destructive nature of our approaches provides superiority to bisulfite in low input applications, such as analysis of single-cells and in long-read epigenetic analysis, applications which are discussed downstream. This approach can also potentially allow for a 'ternary' code to be directly read to resolve C, 5mC and 5hmC.

Our biochemical analysis of A3A revealed that these enzymes use a steric mechanism to discriminate between modified cytosine bases, largely explaining the potent discrimination between C/5mC which are deaminated and ox-mCs which resist deamination. Following our biochemical work, the elucidation the first DNA-bound structure of A3A (37,64) provided a molecular rationale for our observation with a 'steric gate' residue abutting the C5/C6 face of the cytosine base (FIG. 15).

To determine more exact parameters that define the discrimination as a function of sterics at the C5 position, we synthesized or obtained dxCTP analogs, with variable (x) 5-position substituents, and used established approaches to generate long ssDNA substrates with homogeneous C modifications (36). These substrates were reacted with A3A, reamplified and analyzed for deamination by restriction digestion at a specific site. While C and 5mC are readily deaminated and could feasibly fit into the >4 Å between the 5-position of C and the gating tyrosine residue, we find that the addition of a 3-4 atom substituent is sufficient to protect the bases from A3A-mediated deamination, a finding further confirmed with sequencing DNA with 5-propynyl-C(5pyC) (FIG. 15B). Notably, we find that 5-carboxylcytosine (5caC) is additionally similarly resistant to A3A deamination, an important comparison to 5cxmC due to its similar, densely charged nature which may repel the gating tyrosine residue.

Figure 14:
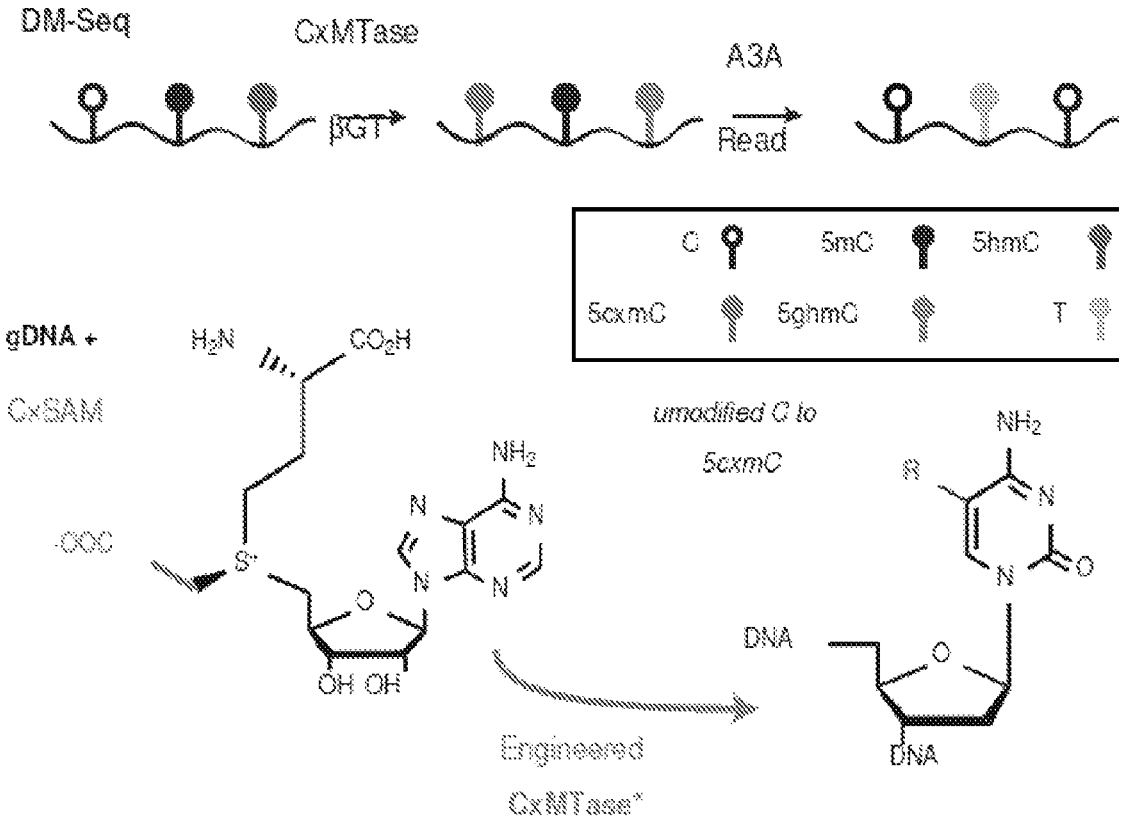
FIG. 14. DM-Seq permits direct detection of 5mC. DM-Seq is an all enzymatic protocol for localization of 5mC alone. As in traditional ACE-Seq, the 5hmC bases are protected from deamination by glucosylation using βGT. DM-Seq leverages the neomorphic CpG MTase enzyme and CxSAM to protect unmodified CpG bases from deamination via their conversion to 5cxmC. The subsequent treatment with the DNA deaminase therefore only leaves 5mC subject to deamination, resulting in a C to T transition in sequencing for bases that were originally 5mCpG.

These mechanistic findings additionally allowed us to conceive of DM-Seq as a new approach for bisulfite-free 5mC detection. In this approach, which we term Direct Methylation sequencing (DM-Seq), unmodified cytosine, but not 5mC or other modified cytosine bases, can be quantitatively reacted with our DNA carboxymethyltransferase (CxMTase) to generate 5cxmC (FIG. 14). The resulting modification would protect the bases from A3A-mediated deamination, rendering 5mC as the only substrate for deamination. We also describe non-deaminase based sequencing approaches where 5cxmC can be used below.

The rationale for this novel and potentially powerful approach is well-supported by the following experiments which show that (1) unmodified C can be protected from deamination by conversion to 5cxmC using the neomorphic DNA CxMTases and CxSAM and (2) this approach being efficient enough for exploitation in direct in sequencing.

First, to establish (1), the M.MpeI N374K variant was reacted with either SAM or CxSAM and unmethylated phage gDNA substrate. Subsequently, this DNA was either deaminated with bisulfite or A3A. The deaminated DNA was subsequently PCR amplified and deep sequenced (FIG. 15C). In this experiment, bisulfite quantifies the extent of modified cytosine transfer while A3A quantifies the extent of enzyme mediated deamination, relative to transfer. First, both negative control lanes with no SAM/CxSAM substrate showed that there were only a small number of total cytosine reads in the CpG context, suggesting efficient deamination by either bisulfite or A3A. When M.MpeI N374K and SAM were incubated together, BS showed that ~60% of the DNA was newly modified to be 5mC. However, A3A was able to deaminate the majority of these 5mC bases, comparable to negative control lanes, reproducing our finding that a small methyl group at the 5-position is still a good substrate for the A3A enzyme. Finally, when M.MpeI N374K and CxSAM were incubated together, BS showed that ~50% of the DNA stayed modified as 5cxmC. Similarly, ~50% of the DNA was newly resistant to A3A deamination, in contrast to the 5mC control. Because both bisulfite and A3A deamination yield comparable levels of modified cytosines, of the ~50% bases that were modified to become 5cxmC, a comparable number percentage was also resistant to A3A transfer, a finding that is consistent with our model that sterically large and polar compounds resist A3A deamination and are thus amenable for DM-Seq.

Figure 16A:
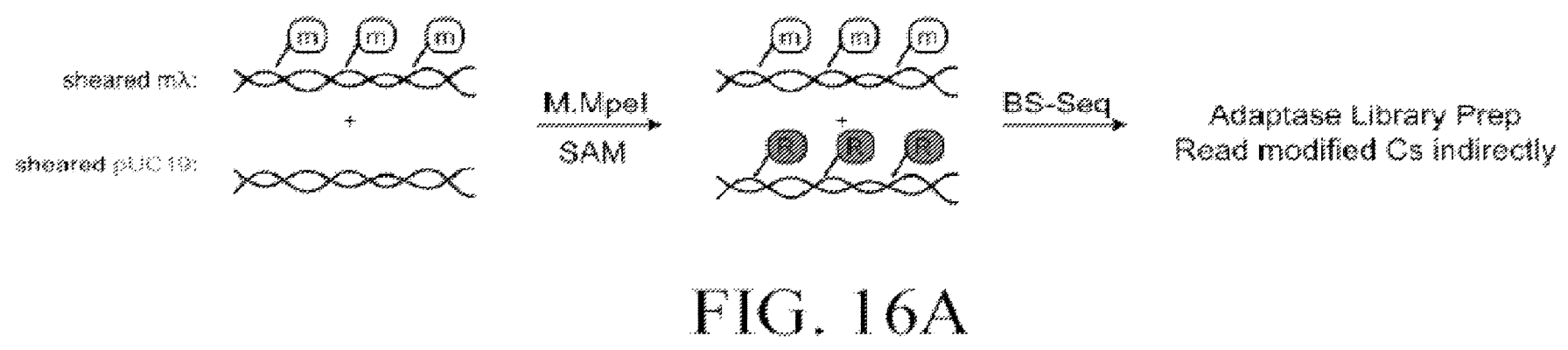
Figure 16B:
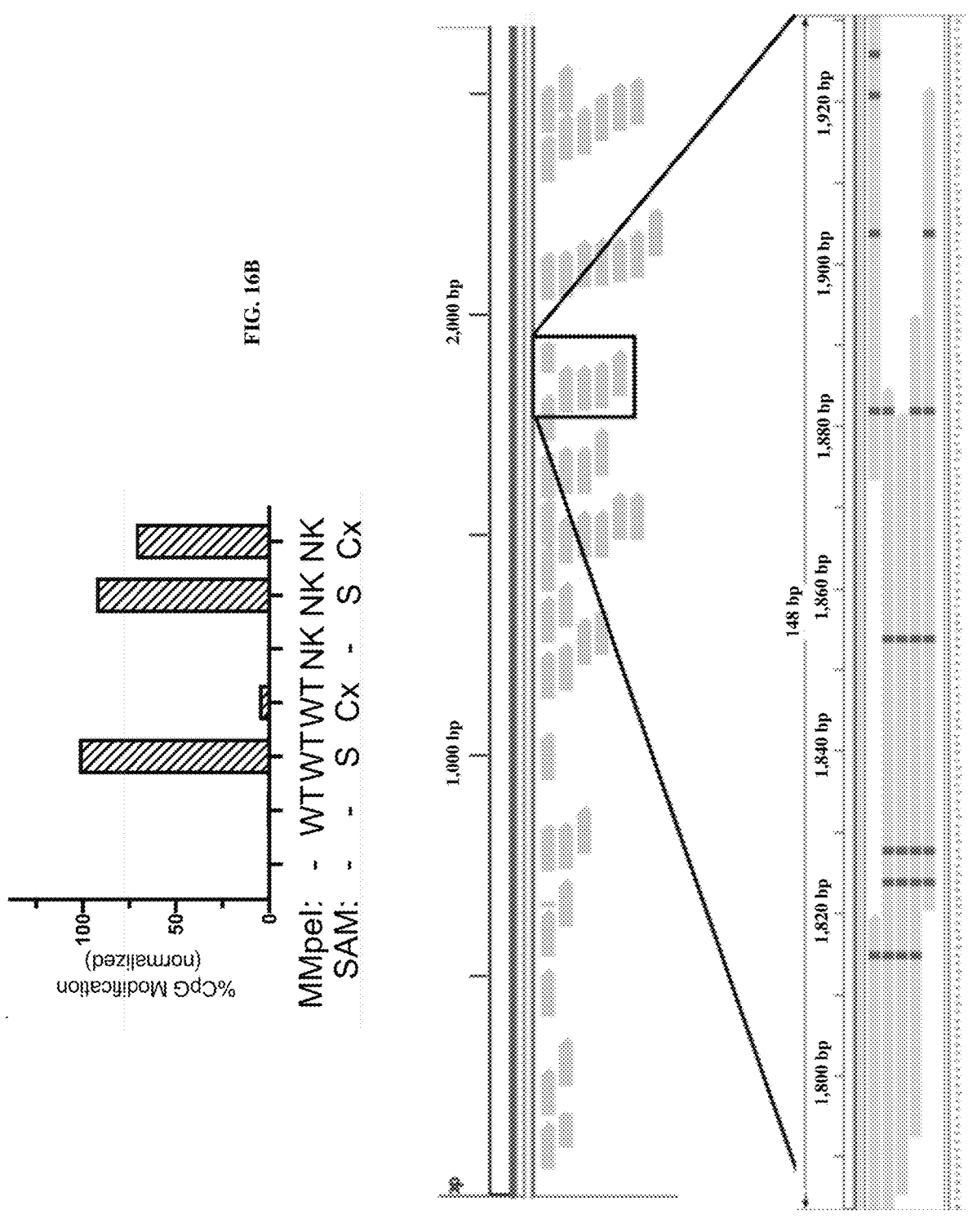

Having established that the 5cxmC side chain is resistant to A3A, to demonstrate (2), we further optimized the efficiency of the carboxymethylation reaction. We incubated M.MpeI WT or N374K with either SAM or CxSAM and a pre-CpG methylated λ phage gDNA substrate and unmethylated pUC19 substrate. After bisulfite treatment, which measures SAM or CxSAM mediated transfer, we performed post deamination library preparation. We quantified SAM or CxSAM transfer based on efficiency relative to the pre-CpG methylated λ phage. First, we showed that in all negative control lanes without SAM or CxSAM substrate, DNA was deaminated and sequenced as T (not C). For the WT M.MpeI, —100% of CpGs were modified to be 5mC with SAM, but they could not be modified to become 5cxmC with CxSAM. However, for our neomorphic M.MpeI N374K, we showed that >70% of CpGs were estimated to be modified as either 5mC with SAM or 5cxmC with CxSAM (FIG. 16A). Individual reads show entire strands of DNA that are fully carboxymethylated at each CpG site (red) across the majority of the pUC19 substrate (FIG. 16B). Collectively, these results showing that full CpG carboxymethylation of DNA with a neomorphic carboxymethyltransferase and CxSAM can be achieved, combined with our data showing that 5cxmC is mechanistically poised to resist direct A3A deamination, indicate that DM-Seq is a viable methodology for localizing 5mC at single base resolution.

Figures 17A, 17B:
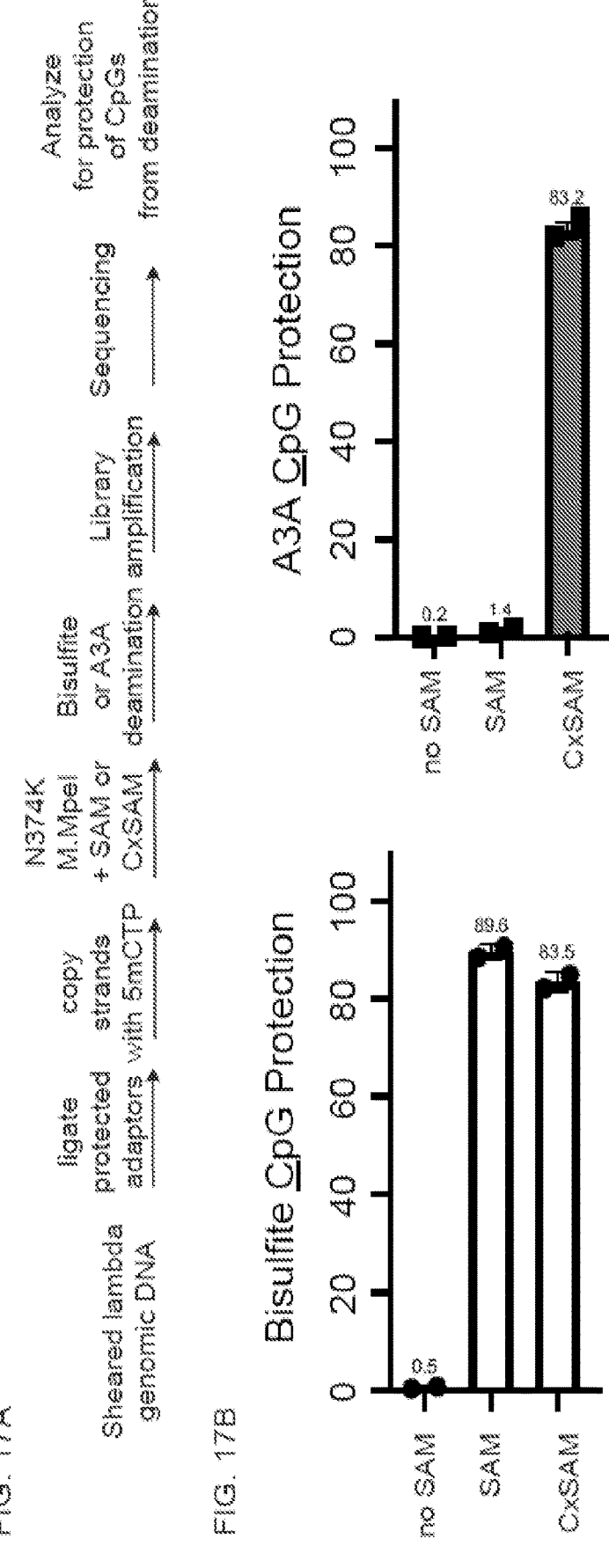
FIGS. 17A-17B. DM-Seq pipeline specifically identifies 5mC.

As further evidence of the ability DM-Seq to directly localize 5mC, we also subjected unmodified lambda genomic DNA to an alternative DM-Seq pipeline. In this approach, the sheared DNA was ligated with forkhead adaptors. The template strands were then copied using Klenow (exo-) polymerase, a primer annealing to the adaptor, and d5mCTP in lieu of dCTP in the dNTP mix. This strand copying introduces 5mCpG sites opposite the unmodified CpGs, as such substrates appear to be ideal for CxMTase activity. The genomic DNA sample was then treated with N374K M.MpeI and either no SAM, normal SAM, or CxSAM. The samples were either chemically deaminated with bisulfite or enzymatically deaminated with A3A and sequenced after library construction. Critically, in the sequencing pipeline with CxSAM and the CxMTase, we observe that the CpGs are protected from deamination by A3A, while deamination readily occurs when CxSAM is replaced by SAM (FIG. 17). These results demonstrate that the inclusion of adaptor, template copying step, and CxMTase step in DM-Seq permits protection of unmodified CpGs, while 5mCpGs can be readily deaminated.

Although our data showing perfect reads is consistent with the model that M.MpeI N374K alone will be sufficient for DM-Seq, additional structure-guided rationalization suggests that some residues may be additionally mutagenized for more efficient transfer with a "second-generation" carboxymethyltransferases. These residues primarily focus on M.MpeI N374K spots which are more difficult to carboxymethylate than others. Specifically, residues T300 and E305 can be additionally mutated to smaller residues such as S, A, G, Q, D, or N to accommodate a modified 5cxmC on the opposite strand of a CpG dyad. We have already shown that G mutants at both of these positions create an enzyme that is still capable of transferring both SAM and CxSAM in vitro. All other mutants have been screened to transfer SAM in vivo, showing the generality of this approach. In addition to residues E305 and T300, residues A323, N306, and Y299 may additionally be mutated to positively charged residues (K/R/H) which could feasibly stabilize an opposite strand 5cxmC. S323 may similarly be mutated to a smaller residue (A/G) or charged (K/R/H) to accommodate multiple modifications in cis. In summary, M.MpeI N374K alone may be applied as the only novel carboxymethyltransferase necessary for DM-Seq, but second generation structurally-rationalized mutations in M.MpeI N374K may enhance the accuracy of DM-Seq.

In one embodiment of this DM-Seq sequencing pipeline, when moving from fixed DNA samples to whole genome analysis, it may also be desirable to use workflows with adaptors that are resistant to deamination by both bisulfite and DNA deaminases. As demonstrated in the analysis above (FIG. 15B), such adaptors could contain modified cytosines themselves, such a 5-propynyl-dC (5pyC) or 5-pyrrolo-dC (5pyrC).

Figures 13A, 13B:
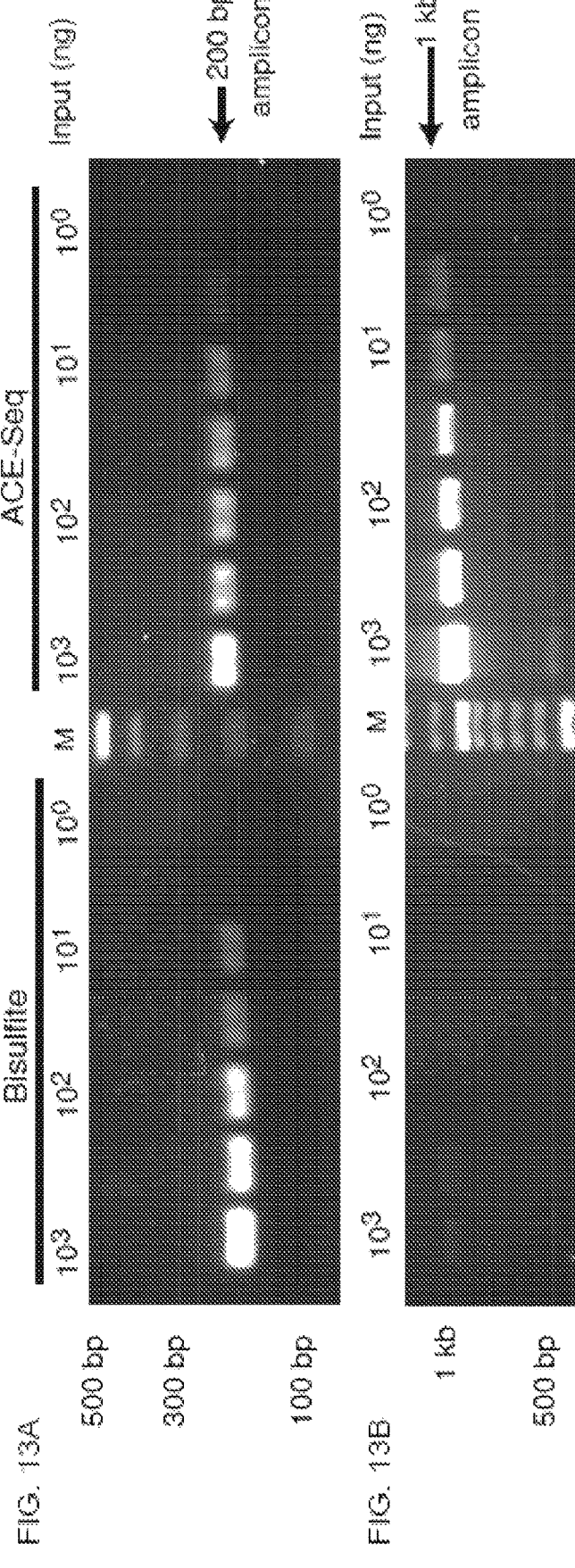
FIG. 13. Enzymatic sequencing with ACE-Seq is non-destructive. Initial input levels of gDNA from mouse embryonic stem cells (ESCs) were titrated from 1 μg to 1 ng, and the samples were treated with either BS-Seq or ACE-Seq protocols. Primers were designed to amplify either (a) a 200-bp amplicon or (b) a 1-kb amplicon from the Tbx5 genomic locus, using 35 cycles of PCR. Resulting amplicons were run on 1.5% agarose gels and stained with SybrSafe. Marker (M) is in the middle lane with bold bands at 1 kb and 500 bp. Bisulfite experiment was performed twice with similar results, and used to inform conditions for the ACE-Seq experiment.

An important advantage of CxMTases including their use in methods such as DM-Seq, is that unlike bisulfite-based methods, enzymatic methods are anticipated to be non-destructive to the DNA samples. As BS-induced abasic sites block PCR amplification, sequencing is typically restricted to <400 bp amplicons (23,24). This latter limitation is of particular importance as biology moves towards a more nuanced understanding of the importance of heterogeneity in cell populations. As noted above, we have previously demonstrated that DNA deaminase-based sequencing is non-destructive (FIG. 13). This feature can also be leveraged in order to perform long-read analysis to resolve heterogeneity at loci with significant biological implications.

Third-generation sequencing relies upon detection of DNA modifications using the time it takes for a polymerase copy opposite an unmodified versus a modified base. Using single molecule real time sequencing (SMRT technology), 5hmC can be distinguished by enzymatic modification. Diglucosylation of 5hmC with T4-βGT followed by T6 phage β-glucosyl-α-glucosyltransferase (T6-βGaGT) produced a bulky modification (hereafter called 5hmC*) that provides a distinctive kinetic signature (Chavez, PNAS, 2014). As the polymerase takes longer to replicate 5hmC* than other cytosine bases, a longer 'intrapulse duration' (IPD) ratio can be measured. While this approach permitted 5hmC detection in a complex eukaryote, the signature for 5mC in SMRT sequencing is comparably weak, with only subtle kinetic alterations several nucleotides downstream of the 5mC. In nanopore-based sequencing, another third generation sequencing approach, ion-current can be made to discriminate between different modification states when a single modified base is present in an oligonucleotide, although sequence context significantly impacts error rate. Thus, the challenge of increasing the window of discrimination between C, 5mC and 5hmC remains the major barrier to resolving the ternary code in single-molecule, long read, sequencing.

DNA deaminases and MTase* can be combined in approaches to perform long-read locus specific sequencing of 5mC and/or 5hmC using a 'binary' readout, with cutting-edge extension to 'ternary code' reads. Three such binary readouts can include distinguishing 5mC (DM-Seq) or potentially via CxMTase treatment alone, which can mark unmodified CpGs with a long IPD if 5cxmC is copied slowly as anticipated.

Viable applications of such a method include efforts to look at key neuronal enhancers from excitatory neuronal cells (Schutsky et al, Nat Biotech, 2018) or T cells where Foxp3 stability is critical to the maintenance of regulatory T-cell (Treg) identity and TET-mediated 5hmC modification and DNA demethylation of two conserved noncoding sequences (CNS1 and CNS2) in the first intron of Foxp3 are required for stable expression.

Figure 18:
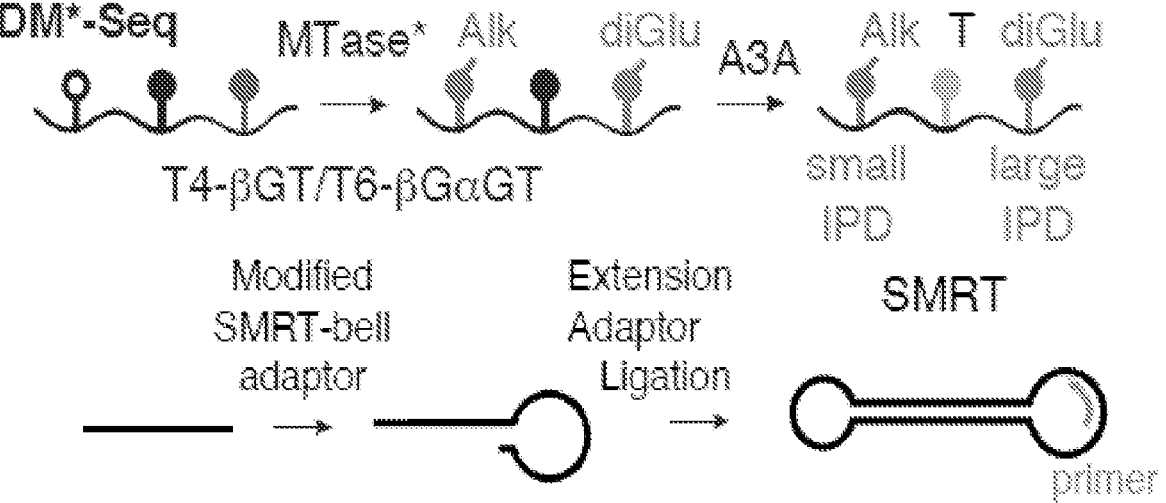
FIG. 18. SMRT technologies for ternary code analysis. The CxMTase also offers a natural approach for sequencing using third generation sequencing approaches (nanopore or SMRT). Shown is a schematic involving DM*-Seq that uses CxMTase for 5mC along with diglucosylation of 5hmC, and deamination, which should offer distinct signatures in SMRT sequencing for C, 5mC and 5hmC. Alternative approaches could be considered without the DNA deaminase, without glucosyltransferases or in concert with TET enzymes.

In our modified work flows using a CxMTase, after treatment of genomic DNA, long amplicons can be generated and subjected to third-generation sequencing, using the PacBio platform which is well suited to these fragment lengths. The DNA can be optionally treated with glucosyltransferases to 5hmC and optimally treated with a deaminase to separate 5mC via deamination. Blunt ended PCR products will be ligated to hairpin adapters, which permit annealing of the sequencing primer and binding of the sequencing polymerase to the universal SMRTbell template. Circular consensus sequencing will be performed, and the output sequence will be aligned to the consensus, focusing on CpGs analysis (FIG. 18). This method can involve amplification of the DNA to detect modifications or potentially direct readout to separate C, 5mC and 5hmC in a "ternary" read.

The generation of long amplicons enables several different approaches to sequencing. We favor SMRT technologies because of the feasibility of extending to 'ternary code' analysis as described above, however, these reads are equally amenable to nanopore sequencing approaches. With ACE-Seq, we demonstrated its proficiency on whole, unsheared phage genomes (39). If necessary, we have data indicating that co-incubation of helicases with A3A results in robust deamination of dsDNA. Using these methods it will be possible to localize 5mC, 5hmC or 5hmC+5hmC localization in single reads from long amplicons.

Epigenetics is fundamentally about understanding how one cell with the same genome differs from the next; in this regard, the necessity to study modifications at a population level, due to short reads, has been limiting, particularly at enhancers or complex loci (such as Foxp3). Notably, long reads also make it possible to overcome methylome phasing challenges, thereby allowing for complete reconstruction of whole chromosome epigenetic maps.

In another application of the sequencing method, rather than analyzing genomic DNA, these methods can be applied to the analysis of circulating cell-free DNA (cfDNA). cfDNA has the genetic and epigenetic hallmarks of the underlying tissues from which the DNA is released, offering a potential means to non-invasively detect and track cancer, for example. cfDNA isolated from the blood of pregnant women may also reveal certain genetic traits. While conventional sequencing can be used to identify pro-oncogenic mutations or chromosome copy number variations, analysis of epigenetic DNA modifications remains a significant challenge. These DNA modifications, which are largely confined to cytosine-guanine dinucleotides (CpGs) in the genome, provide distinctive profiles for different cell types. As cancers have been shown to shed DNA into the circulation, the epigenetic landscape of cfDNA can reveal the tissue-of-origin for various cancers. Assigning the tissue-of-origin can be particularly powerful when partnered with approaches that allow for the early detection of oncogenic mutations in cfDNA. Indeed, as many cancers derived from different tissues share the same driver mutations, determining the tissue-of-origin can focus further clinical investigations and/or streamline therapeutic choices.

As discussed, we have developed a first-in-class, bisulfite-free approach to epigenetic sequencing of sparse DNA samples in ACE-Seq. This work was extended to include use of the novel methyltransferase described above. DM-Seq or related approaches using a CxMTase now permit base-resolution sequencing of both 5mC and 5hmC, offering a non-destructive means to parse C, 5mC and 5hmC on low-input cfDNA.

To demonstrate the usefulness of this technology, pancreatic ductal adenocarcinoma (PDAC) and non-small cell lung carcinoma (NSCLC) cancers which can harbor the same KRAS driver mutations can be analyzed. BS-free whole genome profiling of healthy and cancerous tissues, can be performed using DM-Seq to generate base-resolution profiles of C, 5mC and 5hmC from matched healthy and cancerous tissue from patients in each cohort. These profiles can be used to advantage to demonstrate how the inclusion of 5hmC, by defining differentially-modified regions, permits more rigorous characterization of tissues than BS-Seq based methods which conflate 5mC/5hmC signals.

References for Example III

1. Bestor, T. H., and Bourc'his, D. (2004) Transposon silencing and imprint establishment in mammalian germ cells. Cold Spring Harb. Symp. Quant. Biol. 69, 381-387.
2. Jaenisch, R., and Bird, A. (2003) Epigenetic regulation of gene expression: How the genome integrates intrinsic and environmental signals. Nat. Genet. 33 Suppl, 245-254.
3. Klose, R. J., and Bird, A. P. (2006) Genomic DNA methylation: The mark and its mediators. Trends Biochem. Sci. 31, 89-97.
4. Schubeler, D. (2015) Function and information content of DNA methylation. Nature. 517, 321-326.
5. Varley, K. E., Gertz, J., Bowling, K. M., Parker, S. L., Reddy, T. E., Pauli-Behn, F., Cross, M. K., Williams, B. A., Stamatoyannopoulos, J. A., Crawford, G. E., Absher, D. M., Wold, B. J., and Myers, R. M. (2013) Dynamic DNA methylation across diverse human cell lines and tissues. Genome Res. 23, 555-567.
6. Tahiliani, M., Koh, K. P., Shen, Y., Pastor, W. A., Bandukwala, H., Brudno, Y., Agarwal, S., Iyer, L. M., Liu, D. R., Aravind, L., and Rao, A. (2009) Conversion of 5-methylcytosine to 5-hydroxymethylcytosine in mammalian DNA by MLL partner TET1. Science. 324, 930-935.
7. Ito, S., Shen, L., Dai, Q., Wu, S. C., Collins, L. B., Swenberg, J. A., He, C., and Zhang, Y. (2011) Tet proteins can convert 5-methylcytosine to 5-formylcytosine and 5-carboxylcytosine. Science. 333, 1300-1303.
8. He, Y. F., Li, B. Z., Li, Z., Liu, P., Wang, Y., Tang, Q., Ding, J., Jia, Y., Chen, Z., Li, L., Sun, Y., Li, X., Dai, Q., Song, C. X., Zhang, K., He, C., and Xu, G. L. (2011) Tet-mediated formation of 5-carboxylcytosine and its excision by TDG in mammalian DNA. Science. 333, 1303-1307.
9. Pfaffeneder, T., Hackner, B., Truss, M., Munzel, M., Muller, M., Deiml, C. A., Hagemeier, C., and Carell, T. (2011) The discovery of 5-formylcytosine in embryonic stem cell DNA. Angew. Chem. Int. Ed Engl. 50, 7008-7012.
10. Kohli, R. M., and Zhang, Y. (2013) TET enzymes, TDG and the dynamics of DNA demethylation. Nature. 502, 472-479.
11. Wagner, M., Steinbacher, J., Kraus, T. F., Michalakis, S., Hackner, B., Pfaffeneder, T., Perera, A., Muller, M., Giese, A., Kretzschmar, H. A., and Carell, T. (2015) Age-dependent levels of 5-methyl-, 5-hydroxymethyl-, and 5-formylcytosine in human and mouse brain tissues. Angew. Chem. Int. Ed Engl. 54, 12511-12514.
12. Bachman, M., Uribe-Lewis, S., Yang, X., Burgess, H. E., Iurlaro, M., Reik, W., Murrell, A., and Balasubramanian, S. (2015) 5-formylcytosine can be a stable DNA modification in mammals. Nat. Chem. Biol. 11, 555-557.
13. Booth, M. J., Raiber, E. A., and Balasubramanian, S. (2015) Chemical methods for decoding cytosine modifications in DNA. Chem. Rev. 115, 2240-2254.
14. Song, C. X., Yi, C., and He, C. (2012) Mapping recently identified nucleotide variants in the genome and transcriptome. Nat. Biotechnol. 30, 1107-1116.
15. Wu, H., and Zhang, Y. (2015) Charting oxidized methylcytosines at base resolution. Nat. Struct. Mol. Biol. 22, 656-661.
16. Darst, R. P., Pardo, C. E., Ai, L., Brown, K. D., and Kladde, M. P. (2010) Bisulfite sequencing of DNA. Curr. Protoc. Mol. Biol. Chapter 7, Unit 7.9.1-17.
17. Huang, Y., Pastor, W. A., Shen, Y., Tahiliani, M., Liu, D. R., and Rao, A. (2010) The behaviour of 5-hydroxymethylcytosine in bisulfite sequencing. PLoS One. 5, e8888.
18. Yu, M., Hon, G. C., Szulwach, K. E., Song, C. X., Zhang, L., Kim, A., Li, X., Dai, Q., Shen, Y., Park, B., Min, J. H., Jin, P., Ren, B., and He, C. (2012) Base-resolution analysis of 5-hydroxymethylcytosine in the mammalian genome. Cell. 149, 1368-1380.
19. Yu, M., Hon, G. C., Szulwach, K. E., Song, C. X., Jin, P., Ren, B., and He, C. (2012) Tet-assisted bisulfite sequencing of 5-hydroxymethylcytosine. Nat. Protoc. 7, 2159-2170.
20. Booth, M. J., Branco, M. R., Ficz, G., Oxley, D., Krueger, F., Reik, W., and Balasubramanian, S. (2012) Quantitative sequencing of 5-methylcytosine and 5-hydroxymethylcytosine at single-base resolution. Science. 336, 934-937.
21. Tanaka, K., and Okamoto, A. (2007) Degradation of DNA by bisulfite treatment. Bioorg. Med. Chem. Lett. 17, 1912-1915.
22. Grunau, C., Clark, S. J., and Rosenthal, A. (2001) Bisulfite genomic sequencing: Systematic investigation of critical experimental parameters. Nucleic Acids Res. 29, E65-5.
23. Patterson, K., Molloy, L., Qu, W., and Clark, S. (2011) DNA methylation: Bisulphite modification and analysis. J. Vis. Exp. (56). pii: 3170. doi, 10.3791/3170.
24. Warnecke, P. M., Stirzaker, C., Song, J., Grunau, C., Melki, J. R., and Clark, S. J. (2002) Identification and resolution of artifacts in bisulfite sequencing. Methods. 27, 101-107.
25. Meissner, A., Gnirke, A., Bell, G., Ramsahoye, B., Lander, E., and Jaenisch, R. (2005) Reduced representation bisulfite sequencing for comparative high-resolution DNA methylation analysis. Nucleic Acids Res. 33, 5868-5877.
26. Gu, H., Smith, Z. D., Bock, C., Boyle, P., Gnirke, A., and Meissner, A. (2011) Preparation of reduced representation bisulfite sequencing libraries for genome-scale DNA methylation profiling. Nat. Protoc. 6, 468-481.

27. Wescoe, Z. L., Schreiber, J., and Akeson, M. (2014) Nanopores discriminate among five C5-cytosine variants in DNA. J. Am. Chem. Soc. 136, 16582-16587.

28. Li, W. W., Gong, L., and Bayley, H. (2013) Single-molecule detection of 5-hydroxymethylcytosine in DNA through chemical modification and nanopore analysis. Angew. Chem. Int. Ed Engl. 52, 4350-4355.

29. Wanunu, M., Cohen-Karni, D., Johnson, R. R., Fields, L., Benner, J., Peterman, N., Zheng, Y., Klein, M. L., and Drndic, M. (2011) Discrimination of methylcytosine from hydroxymethylcytosine in DNA molecules. J. Am. Chem. Soc. 133, 486-492.

30. Wallace, E. V., Stoddart, D., Heron, A. J., Mikhailova, E., Maglia, G., Donohoe, T. J., and Bayley, H. (2010) Identification of epigenetic DNA modifications with a protein nanopore. Chem. Commun. (Camb). 46, 8195-8197.

31. Laszlo, A. H., Derrington, I. M., Brinkerhoff, H., Langford, K. W., Nova, I. C., Samson, J. M., Bartlett, J. J., Pavlenok, M., and Gundlach, J. H. (2013) Detection and mapping of 5-methylcytosine and 5-hydroxymethylcytosine with nanopore MspA. Proc. Natl. Acad. Sci. U.S.A. 110, 18904-18909.

32. Chavez, L., Huang, Y., Luong, K., Agarwal, S., Iyer, L. M., Pastor, W. A., Hench, V. K., Frazier-Bowers, S. A., Korol, E., Liu, S., Tahiliani, M., Wang, Y., Clark, T. A., Korlach, J., Pukkila, P. J., Aravind, L., and Rao, A. (2014) Simultaneous sequencing of oxidized methylcytosines produced by TET/JBP dioxygenases in *coprinopsis cinerea*. Proc. Natl. Acad. Sci. U.S.A 111, E5149-58.

33. Flusberg, B. A., Webster, D. R., Lee, J. H., Travers, K. J., Olivares, E. C., Clark, T. A., Korlach, J., and Turner, S. W. (2010) Direct detection of DNA methylation during single-molecule, real-time sequencing. Nat. Methods. 7, 461-465.

34. Nabel, C. S., Manning, S. A., and Kohli, R. M. (2012) The curious chemical biology of cytosine: Deamination, methylation, and oxidation as modulators of genomic potential. ACS Chem. Biol. 7, 20-30.

35. Nabel, C. S., Jia, H., Ye, Y., Shen, L., Goldschmidt, H. L., Stivers, J. T., Zhang, Y., and Kohli, R. M. (2012) AID/APOBEC deaminases disfavor modified cytosines implicated in DNA demethylation. Nat. Chem. Biol. 8, 751-758.

36. Schutsky, E. K., Nabel, C. S., Davis, A. K. F., DeNizio, J. E., and Kohli, R. M. (2017) APOBEC3A efficiently deaminates methylated, but not TET-oxidized, cytosine bases in DNA. Nucleic Acids Res. 45, 7655-7665.

37. Shi, K., Carpenter, M. A., Banerjee, S., Shaban, N. M., Kurahashi, K., Salamango, D. J., McCann, J. L., Starrett, G. J., Duffy, J. V., Demir, O., Amaro, R. E., Harki, D. A., Harris, R. S., and Aihara, H. (2017) Structural basis for targeted DNA cytosine deamination and mutagenesis by APOBEC3A and APOBEC3B. Nat. Struct. Mol. Biol. 24, 131-139.

38. Kouno, T., Silvas, T. V., Hilbert, B. J., Shandilya, S. M. D., Bohn, M. F., Kelch, B. A., Royer, W. E., Somasundaran, M., Kurt Yilmaz, N., Matsuo, H., and Schiffer, C. A. (2017) Crystal structure of APOBEC3A bound to single-stranded DNA reveals structural basis for cytidine deamination and specificity. Nat. Commun. 8, 15024.

39. Schutsky, E. K., DeNizio, J. E., Hu, P., Liu, M. Y., Nabel, C. S., Fabyanic, E. B., Hwang, Y., Bushman, F. D., Wu, H., and Kohli, R. M. (2018) Nondestructive, base-resolution sequencing of 5-hydroxymethylcytosine using a DNA deaminase. Nat. Biotech. e-pub ahead of print, doi: 10.1038/nbt.4204.

40. Siriwardena, S. U., Chen, K., and Bhagwat, A. S. (2016) Functions and malfunctions of mammalian DNA-cytosine deaminases. Chem. Rev. 116, 12688-12710.

41. Beale, R. C., Petersen-Mahrt, S. K., Watt, I. N., Harris, R. S., Rada, C., and Neuberger, M. S. (2004) Comparison of the differential context-dependence of DNA deamination by APOBEC enzymes: Correlation with mutation spectra in vivo. J. Mol. Biol. 337, 585-596.

42. Liu, M. Y., Torabifard, H., Crawford, D. J., DeNizio, J. E., Cao, X. J., Garcia, B. A., Cisneros, G. A., and Kohli, R. M. (2017) Mutations along a TET2 active site scaffold stall oxidation at 5-hydroxymethylcytosine. Nat. Chem. Biol. 13, 181-187.

43. Liu, M. Y., DeNizio, J. E., and Kohli, R. M. (2016) Quantification of oxidized 5-methylcytosine bases and TET enzyme activity. Methods Enzymol. 573, 365-385.

44. Crawford, D. J., Liu, M. Y., Nabel, C. S., Cao, X. J., Garcia, B. A., and Kohli, R. M. (2016) Tet2 catalyzes stepwise 5-methylcytosine oxidation by an iterative and de novo mechanism. J. Am. Chem. Soc. 138, 730-733.

45. Bryson, A. L., Hwang, Y., Sherrill-Mix, S., Wu, G. D., Lewis, J. D., Black, L., Clark, T. A., and Bushman, F. D. (2015) Covalent modification of bacteriophage T4 DNA inhibits CRISPR-Cas9. MBio. 6, e00648-15.

46. Kizaki, S., and Sugiyama, H. (2014) CGmCGCG is a versatile substrate with which to evaluate tet protein activity. Org. Biomol. Chem. 12, 104-107.

47. Fu, L., Guerrero, C. R., Zhong, N., Amato, N. J., Liu, Y., Liu, S., Cai, Q., Ji, D., Jin, S. G., Niedernhofer, L. J., Pfeifer, G. P., Xu, G. L., and Wang, Y. (2014) Tet-mediated formation of 5-hydroxymethylcytosine in RNA. J. Am. Chem. Soc. 136, 11582-11585.

48. Wang, H., Yang, H., Shivalila, C. S., Dawlaty, M. M., Cheng, A. W., Zhang, F., and Jaenisch, R. (2013) One-step generation of mice carrying mutations in multiple genes by CRISPR/cas-mediated genome engineering. Cell. 153, 910-918.

49. Lu, F., Liu, Y., Jiang, L., Yamaguchi, S., and Zhang, Y. (2014) Role of tet proteins in enhancer activity and telomere elongation. Genes Dev. 28, 2103-2119.

50. Wu, H., Wu, X., Shen, L., and Zhang, Y. (2014) Single-base resolution analysis of active DNA demethylation using methylase-assisted bisulfite sequencing. Nat. Biotechnol. 32, 1231-1240.

51. Smallwood, S. A., Lee, H. J., Angermueller, C., Krueger, F., Saadeh, H., Peat, J., Andrews, S. R., Stegle, O., Reik, W., and Kelsey, G. (2014) Single-cell genome-wide bisulfite sequencing for assessing epigenetic heterogeneity. Nat. Methods. 11, 817-820.

52. Luo, C., Keown, C. L., Kurihara, L., Zhou, J., He, Y., Li, J., Castanon, R., Lucero, J., Nery, J. R., Sandoval, J. P., Bui, B., Sejnowski, T. J., Harkins, T. T., Mukamel, E. A., Behrens, M. M., and Ecker, J. R. (2017) Single-cell methylomes identify neuronal subtypes and regulatory elements in mammalian cortex. Science. 357, 600-604.

53. Mulqueen, R. M., Pokholok, D., Norberg, S. J., Torkenczy, K. A., Fields, A. J., Sun, D., Sinnamon, J. R., Shendure, J., Trapnell, C., O'Roak, B. J., Xia, Z., Steemers, F. J., and Adey, A. C. (2018) Highly scalable generation of DNA methylation profiles in single cells. Nat. Biotechnol. 36, 428-431.

54. Kelsey, G., Stegle, O., and Reik, W. (2017) Single-cell epigenomics: Recording the past and predicting the future. Science. 358, 69-75.

55. Gawad, C., Koh, W., and Quake, S. R. (2016) Single-cell genome sequencing: Current state of the science. Nat. Rev. Genet. 17, 175-188.

56. Lister, R., Mukamel, E. A., Nery, J. R., Urich, M., Puddifoot, C. A., Johnson, N. D., Lucero, J., Huang, Y., Dwork, A. J., Schultz, M. D., Yu, M., Tonti-Filippini, J., Heyn, H., Hu, S., Wu, J. C., Rao, A., Esteller, M., He, C., Haghighi, F. G., Sejnowski, T. J., Behrens, M. M., and Ecker, J. R. (2013) Global epigenomic reconfiguration during mammalian brain development. Science. 341, 1237905.

57. Kriaucionis, S., and Heintz, N. (2009) The nuclear DNA base 5-hydroxymethylcytosine is present in purkinje neurons and the brain. Science. 324, 929-930.

58. Angermueller, C., Clark, S. J., Lee, H. J., Macaulay, I. C., Teng, M. J., Hu, T. X., Krueger, F., Smallwood, S., Ponting, C. P., Voet, T., Kelsey, G., Stegle, O., and Reik, W. (2016) Parallel single-cell sequencing links transcriptional and epigenetic heterogeneity. Nat. Methods. 13, 229-232.

59. Cholewa-Waclaw, J., Bird, A., von Schimmelmann, M., Schaefer, A., Yu, H., Song, H., Madabhushi, R., and Tsai, L. H. (2016) The role of epigenetic mechanisms in the regulation of gene expression in the nervous system. J. Neurosci. 36, 11427-11434.

60. Hu, P., Fabyanic, E., Kwon, D. Y., Tang, S., Zhou, Z., and Wu, H. (2017) Dissecting cell-type composition and activity-dependent transcriptional state in mammalian brains by massively parallel single-nucleus RNA-seq. Mol. Cell. 68, 1006-1015.e7.

61. Fisher, S., Barry, A., Abreu, J., Minie, B., Nolan, J., Delorey, T. M., Young, G., Fennell, T. J., Allen, A., Ambrogio, L., Berlin, A. M., Blumenstiel, B., Cibulskis, K., Friedrich, D., Johnson, R., Juhn, F., Reilly, B., Shammas, R., Stalker, J., Sykes, S. M., Thompson, J., Walsh, J., Zimmer, A., Zwirko, Z., Gabriel, S., Nicol, R., and Nusbaum, C. (2011) A scalable, fully automated process for construction of sequence-ready human exome targeted capture libraries. Genome Biol. 12, R1-2011-12-1-r1. Epub Jan. 4, 2011.

62. Dunham, J. P., and Friesen, M. L. (2013) A cost-effective method for high-throughput construction of illumina sequencing libraries. Cold Spring Harb Protoc. 2013, 820-834.

63. Picelli, S., Bjorklund, A. K., Faridani, O. R., Sagasser, S., Winberg, G., and Sandberg, R. (2013) Smart-seq2 for sensitive full-length transcriptome profiling in single cells. Nat. Methods. 10, 1096-1098.

64. Schutsky, E. K., Hostetler, Z. M., and Kohli, R. M. (2017) Mechanisms for targeted, purposeful mutation revealed in an APOBEC-DNA complex. Nat. Struct. Mol. Biol. 24, 97-98.

65. Wu, H., Wu, X., and Zhang, Y. (2016) Base-resolution profiling of active DNA demethylation using MAB-seq and caMAB-seq. Nat. Protoc. 11, 1081-1100.

66. Kriukiene, E., Labrie, V., Khare, T., Urbanaviciute, G., Lapinaite, A., Koncevicius, K., Li, D., Wang, T., Pai, S., Ptak, C., Gordevicius, J., Wang, S. C., Petronis, A., and Klimasauskas, S. (2013) DNA unmethylome profiling by covalent capture of CpG sites. Nat. Commun. 4, 2190.

67. Lukinavicius, G., Lapinaite, A., Urbanaviciute, G., Gerasimaite, R., and Klimasauskas, S. (2012) Engineering the DNA cytosine-5 methyltransferase reaction for sequence-specific labeling of DNA. Nucleic Acids Res. 40, 11594-11602.

68. Liutkeviciute, Z., Kriukiene, E., Grigaityte, I., Masevicius, V., and Klimasauskas, S. (2011) Methyltransferase-directed derivatization of 5-hydroxymethylcytosine in DNA. Angew. Chem. Int. Ed Engl. 50, 2090-2093.

69. Dalhoff, C., Lukinavicius, G., Klimasauskas, S., and Weinhold, E. (2006) Direct transfer of extended groups from synthetic cofactors by DNA methyltransferases. Nat. Chem. Biol. 2, 31-32.

70. Dalhoff, C., Lukinavicius, G., Klimasauskas, S., and Weinhold, E. (2006) Synthesis of S-adenosyl-L-methionine analogs and their use for sequence-specific transalkylation of DNA by methyltransferases. Nat. Protoc. 1, 1879-1886.

71. Wojciechowski, M., Czapinska, H., and Bochtler, M. (2013) CpG underrepresentation and the bacterial CpG-specific DNA methyltransferase M.MpeI. Proc. Natl. Acad. Sci. U.S.A 110, 105-110.

72. Kohli, R. M., Abrams, S. R., Gajula, K. S., Maul, R. W., Gearhart, P. J., and Stivers, J. T. (2009) A portable hotspot recognition loop transfers sequence preferences from APOBEC family members to activation-induced cytidine deaminase. J. Biol. Chem. 284, 22898-22904.

73. Gajula, K. S., Huwe, P. J., Mo, C. Y., Crawford, D. J., Stivers, J. T., Radhakrishnan, R., and Kohli, R. M. (2014) High-throughput mutagenesis reveals functional determinants for DNA targeting by activation-induced deaminase. Nucleic Acids Res. 42, 9964-9975.

74. Masevicius, V., Nainyte, M., and Klimasauskas, S. (2016) Synthesis of S-adenosyl-L-methionine analogs with extended transferable groups for methyltransferase-directed labeling of DNA and RNA. Curr. Protoc. Nucleic Acid Chem. 64, 1.36.1-13.

75. Beaulaurier, J., Zhang, X. S., Zhu, S., Sebra, R., Rosenbluh, C., Deikus, G., Shen, N., Munera, D., Waldor, M. K., Chess, A., Blaser, M. J., Schadt, E. E., and Fang, G. (2015) Single molecule-level detection and long read-based phasing of epigenetic variations in bacterial methylomes. Nat. Commun. 6, 7438.

76. Eckhardt, F., Lewin, J., Cortese, R., Rakyan, V. K., Attwood, J., Burger, M., Burton, J., Cox, T. V., Davies, R., Down, T. A., Haefliger, C., Horton, R., Howe, K., Jackson, D. K., Kunde, J., Koenig, C., Liddle, J., Niblett, D., Otto, T., Pettett, R., Seemann, S., Thompson, C., West, T., Rogers, J., Olek, A., Berlin, K., and Beck, S. (2006) DNA methylation profiling of human chromosomes 6, 20 and 22. Nat. Genet. 38, 1378-1385.

77. Shoemaker, R., Deng, J., Wang, W., and Zhang, K. (2010) Allele-specific methylation is prevalent and is contributed by CpG-SNPs in the human genome. Genome Res. 20, 883-889.

78. Yue, X., Trifari, S., Aijo, T., Tsagaratou, A., Pastor, W. A., Zepeda-Martinez, J. A., Lio, C. W., Li, X., Huang, Y., Vijayanand, P., Landesmaki, H., and Rao, A. (2016) Control of Foxp3 stability through modulation of TET activity. J. Exp. Med. 213, 377-397.

79. Schreiber, J., Wescoe, Z. L., Abu-Shumays, R., Vivian, J. T., Baatar, B., Karplus, K., and Akeson, M. (2013) Error rates for nanopore discrimination among cytosine, methylcytosine, and hydroxymethylcytosine along individual DNA strands. Proc. Natl. Acad. Sci. U.S.A 110, 18910-18915.

80. Simpson, J. T., Workman, R. E., Zuzarte, P. C., David, M., Dursi, L. J., and Timp, W. (2017) Detecting DNA cytosine methylation using nanopore sequencing. Nat. Methods. 14, 407-410.

81. Hoijer, I., Tsai, Y. C., Clark, T. A., Kotturi, P., Dahl, N., Stattin, E. L., Bondeson, M. L., Feuk, L., Gyllensten, U., and Ameur, A. (2018) Detailed analysis of HTT repeat elements in human blood using targeted amplification-free long-read sequencing. Hum. Mutat. 39, 1262-1272.

82. Tsai, Y., Greenberg, D., Powell, J., Hoijer, I., Ameur, A., Strahl, M., Ellis, E., Jonasson, I., Mouro Pinto, R., Wheeler, V., Smith, M. L., Gyllensten, U., Sebra, R., Korlach, J., and Clark, T. A. (2017) Amplification-free, CRISPR-Cas9 targeted enrichment and SMRT sequencing of repeat-expansion disease causative genomic regions. BioRx. 203919; doi: https://doi.org/10.1101/203919.

83. Samorodnitsky, E., Datta, J., Jewell, B. M., Hagopian, R., Miya, J., Wing, M. R., Damodaran, S., Lippus, J. M., Reeser, J. W., Bhatt, D., Timmers, C. D., and Roychowdhury, S. (2015) Comparison of custom capture for targeted next-generation DNA sequencing. J. Mol. Diagn. 17, 64-75.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated genetically modified methyltransferase enzyme having carboxymethyltransferase activity, which catalyzes formation of 5-carboxymethylcytosine employing carboxy-S-adenosyl-L-methionine (CxSAM) as a substrate, said enzyme having an active site motif naturally comprising a polar amino acid residue that is situated adjacent to carbon 5 of a target cytosine present in a nucleic acid of interest, wherein said polar amino acid is substituted with a positively charged amino acid, wherein said enzyme comprises an amino acid sequence having at least 90% sequence identity to SEQ ID NO: 1, and wherein position N374 of SEQ ID NO: 1 can be either K or R.

2. The methyltransferase enzyme of claim 1, wherein said enzyme comprises the amino acid sequence as set forth in SEQ ID NO: 1.

3. The methyltransferase enzyme of claim 1, wherein said enzyme further comprises one or more amino acid substitutions selected from:

a) substitution of one or both residues at T300 and E305 with S, A, G, Q, D, or N;
   b) substitution of one or more residues A323, N306, and Y299 with a positively charged amino acid selected from K, R or H; and
   c) substitution of S323 with A, G, K, R or H.

4. A method for resolving unmethylated cytosine (C), 5-methylcytosine (5mC) and 5-hydroxymethylcytosine (5hmC) in a polynucleotide sample, comprising:

(a) reacting a polynucleotide containing C, 5mC, and/or 5hmC with the methyltransferase enzyme of claim 1, in the presence of carboxy-S-adenosyl-L-methionine (Cx-SAM) substrate, thereby labeling any unmodified C in said polynucleotide and rendering it resistant to deaminase action; wherein said 5hmC is also optionally glucosylated;

(b) contacting the polynucleotide of step (a) with a deaminase which deaminates 5mC and/or 5hmC; and
   (c) analyzing said polynucleotide sample, to identify each of unmodified C, 5mC, and 5hmC present in said polynucleotide.

5. The method of claim 4, wherein said polynucleotide in said sample is fragmented or sheared prior to step (a), and sequence adapters containing modified cytosine bases resistant to deamination, are operably linked to said sheared or fragmented polynucleotide, and wherein said analyzing step of (c) is performed by sequencing.

6. The method of claim 5, wherein the sample of step (b) is amplified prior to the sequencing of step (c).

7. The method of claim 4, wherein said methyltransferase enzyme comprises the amino acid sequence as set forth in SEQ ID NO: 1, and said deaminase enzyme is APOBEC3A, and modified cytosine base is 5pyC.

8. The method of claim 4, wherein said polynucleotide is genomic DNA.

9. The method of claim 4, further comprising inclusion of methylated control polynucleotides.

10. The method of claim 4, wherein said polynucleotide is present in cell free DNA.

11. The method of claim 4, wherein said polynucleotide sample is obtained from cancer cells.

12. The method of claim 4, wherein said polynucleotide sample is isolated from the blood of a pregnant woman.

13. The method of claim 4, further comprising comparing with results obtained using bisulfite dependent 5mC+5hmC localization and ACE-seq 5hmC localization.

14. A nucleic acid vector encoding the methyltransferase enzyme of claim 1.

15. A host cell with naturally occurring CxSAM and said host cell comprising the nucleic acid vector of claim 14.

16. The host cell of claim 15, wherein said host cell is an *E. coli* cell.

17. A kit comprising the methyltransferase enzyme of claim 1, and CxSAM.

18. The kit of claim 17, wherein said kit further comprises a cytosine deaminase enzyme.

19. The kit of claim 18, wherein said cytosine deaminase enzyme is APOBEC3A.

20. The kit of claim 19, wherein said kit further comprises reagents and enzymes for cleaving or shearing DNA and optionally reagents for amplification of DNA.

21. A method for identifying S-adenosyl-methionine (SAM) analogs which render cytosine residues present in a polynucleotide resistant to deaminase action, comprising;

a) reacting a polynucleotide containing C, 5mC, and/or 5hmC with the methyltransferase enzyme of claim 1 in the presence of substrates comprising SAM analogs;

b) isolating polynucleotides comprising modified C residues which are resistant to deaminase action, thereby identifying said SAM analog.

22. The method of claim 21, wherein said methylase enzyme comprises the amino acid sequence as set forth in SEQ ID NO: 1.

\* \* \* \* \*